(12) United States Patent
Mallikaratchy

(10) Patent No.: US 11,634,704 B2
(45) Date of Patent: Apr. 25, 2023

(54) LIGAND-GUIDED-SELECTION METHOD FOR SCREENING ANTIGEN-SPECIFIC LIGANDS

(71) Applicant: Research Foundation of the City University of New York, New York, NY (US)

(72) Inventor: Prabodhika Mallikaratchy, New York, NY (US)

(73) Assignee: Research Foundation of the City University of New York, New York, NY (US)

( * ) Notice: Subject to any disclaimer, the term of this patent is extended or adjusted under 35 U.S.C. 154(b) by 1073 days.

(21) Appl. No.: 16/283,156

(22) Filed: Feb. 22, 2019

(65) Prior Publication Data

US 2019/0177716 A1 Jun. 13, 2019

Related U.S. Application Data

(63) Continuation-in-part of application No. 15/097,845, filed on Apr. 13, 2016, now Pat. No. 10,253,314.

(60) Provisional application No. 62/320,793, filed on Apr. 11, 2016, provisional application No. 62/253,963, filed on Nov. 11, 2015, provisional application No. 62/146,472, filed on Apr. 13, 2015.

(51) Int. Cl.
| | |
|---|---|
| *C12N 15/10* | (2006.01) |
| *G16B 30/10* | (2019.01) |
| *C40B 30/04* | (2006.01) |
| *G01N 33/53* | (2006.01) |

(52) U.S. Cl.
CPC ..... *C12N 15/1048* (2013.01); *G01N 33/5308* (2013.01); *G16B 30/10* (2019.02); *C40B 30/04* (2013.01); *G01N 2500/04* (2013.01); *G01N 2500/10* (2013.01)

(58) Field of Classification Search
CPC ........... C12N 15/1048; C40B 30/04; G01N 33/5308; G01N 2500/04; G01N 2500/10; G16B 30/10
See application file for complete search history.

(56) References Cited

U.S. PATENT DOCUMENTS

| | | | |
|---|---|---|---|
| 5,567,588 A | 10/1996 | Gold et al. | |
| 5,861,254 A | 1/1999 | Schneider et al. | |
| 6,127,119 A | 10/2000 | Stephens et al. | |
| 6,376,190 B1 | 4/2002 | Gold et al. | |

(Continued)

OTHER PUBLICATIONS

Janeway et al., Immunobiology: The Immune System in Health and Disease. 5th edition. New York: Garland Science; 2001. The structure of a typical antibody molecule (Year: 2001).*

(Continued)

*Primary Examiner* — Jeremy C Flinders
(74) *Attorney, Agent, or Firm* — Peter J. Mikesell; Schmeiser, Olsen & Watts, LLP

(57) ABSTRACT

A Ligand-guided-Selection (LIGS) method for identifying highly specific aptamers against a predetermined antigen of a target is provided. LIGS uses a stronger and highly specific bivalent binder (e.g. an antibody) interacting with its cognate antigen to displace specific aptamers from an enriched SELEX pool. Elution of the displaced aptamers provides aptamers that are specific to the predetermined antigen.

17 Claims, 29 Drawing Sheets

Specification includes a Sequence Listing.

(56) References Cited

U.S. PATENT DOCUMENTS

2016/0003835 A1    1/2016  Halbert et al.

OTHER PUBLICATIONS

Tang et al.; Selection of Aptamers for Molecular Recognition and Characterization of Cancer Cells; Analytical Chemistry; Jul. 1, 2007; pp. 4900-4907; vol. 79, No. 13; Americam Chemical Society.
Ye et al.; Generating Aptamers by Cell-SELEX for Applications in Molecular Medicine; International Journal of Molecular Sciences; Mar. 12, 2012; pp. 3341-3353; ISSN 1422-0067.
Mallikaratchy et al.; Aptamer Directly Evolved from Live Cells Recognizes Membrane Bound Immunoglobin Heavy Mu Chain in Burkitt's Lymphoma Cells; Molecular & Cellular Proteomics; Sep. 17, 2007; pp. 2230-2238; The American Society for Biochemistry and Molecular Biology, Inc.; US.
Sefah et al.; Development of DNA aptamers using Cell-SELEX; Nature Protocols; Jun. 3, 2010; pp. 1169-1185; vol. 5 No. 6; Nature Publishing Group; US.
Wilner et al.; An RNA Alternative to Human Transferrin: A New Tool for Targeting Human Cells; Molecular Therapy—Nucleic Acids; May 15, 2012; pp. 1-14; American Society of Gene & Cell Therapy; US.
Ellington, A et al.; In Vitro selection of RNA molecules that bind specific ligands; nature; Aug. 30, 1990; pp. 818-822 vol. 346; Nature Publishing Group.
Burke, D. et al.; RNA aptamers to the adenosine moiety of S-adenosyl methionine: structural inferences from variations on a theme and the reproducibility of SELEX; Nucleic Acids Research; May 5, 1997; pp. 2020-2024; vol. 25, No. 10; Oxford University Press.

Shangguan, D. et al; Aptamers evolved from live cells as effective molecular probes for cancer study; PNAS Aug. 8, 2006; pp. 11838-11843; vol. 103, No. 32; PMAS.
Theil, K. et al; Delivery of chemo-sensitizing siRNAs to HER2+- breast cancer cells using RNA aptamers; Nucleic Acids Research; Mar. 30, 2012; pp. 1-19.
Mayer, G. et al; Fluorescence-activated cell sorting for aptamer SELEX with cell mixtures; Nature Protocols; Dec. 2, 2010; pp. 1993-2004; vol. 5, No. 12; Nature America Inc.
Raddatz, M.L et al; Enrichment of Cell-Targeting and Population-Specific Aptamers by Fluorescence-Activated Cell Sorting; Angew. Chem. Int. Ed.; Jun. 3, 2008; pp. 5190-5193; vol. 47; Wiley-VCH Verlag GmbH & Co. KGaA.
Ulrich, H. et al.; In Vitro Selection of RNA Aptamers That Bind to Cell Adhesion Receptors of Trypanosoma cruzi and Inhibit Cell Invasion; The Journal of Biological Chemistry; Mar. 27, 2002; pp. 20756-20762; vol. 277, No. 23.
Kim, J. et al.; Identification of DNA Aptamers toward Epithelial Cell Adhesion Molecule Cell-SELEX; Mo. Cells; Sep. 29, 2014; pp. 742-746; 37 (10).
Tapp, M. et al.; Competition-Enhanced Ligand Selection to Identify DNA Aptamers; ACS Comb. Sci. Sep. 6, 2018; pp. 585-593; DOI: 10.1021/acscombsci.8b00048.
Mallikaratchy, P.; Evolution of Complex Target SELEX to Identify Aptamers against Mammalian Cell-Surface Antigens; molecules; Jan. 30, 2017; 12 pages; vol. 215.
Zumrut. H., et al; Ligand-Guided Selection of Target-Specific Aptamers: A Screening Technology for Identifying Specific Aptamers Against Cell-Surface Proteins; Nucleic Acid Therapeutics; 2016; pp. 190-198; vol. 26, No. 3.
Zumrut. H., et al; Ligand-guided selection of aptamers against T-cell Receptor-cluster of differentiation 3 (TCR-CD3) expressed on Jurkat. E6 cells; Analytical Biochemistry; Aug. 9, 2016; 7 pages; vol. 512.

* cited by examiner

FIG. 5

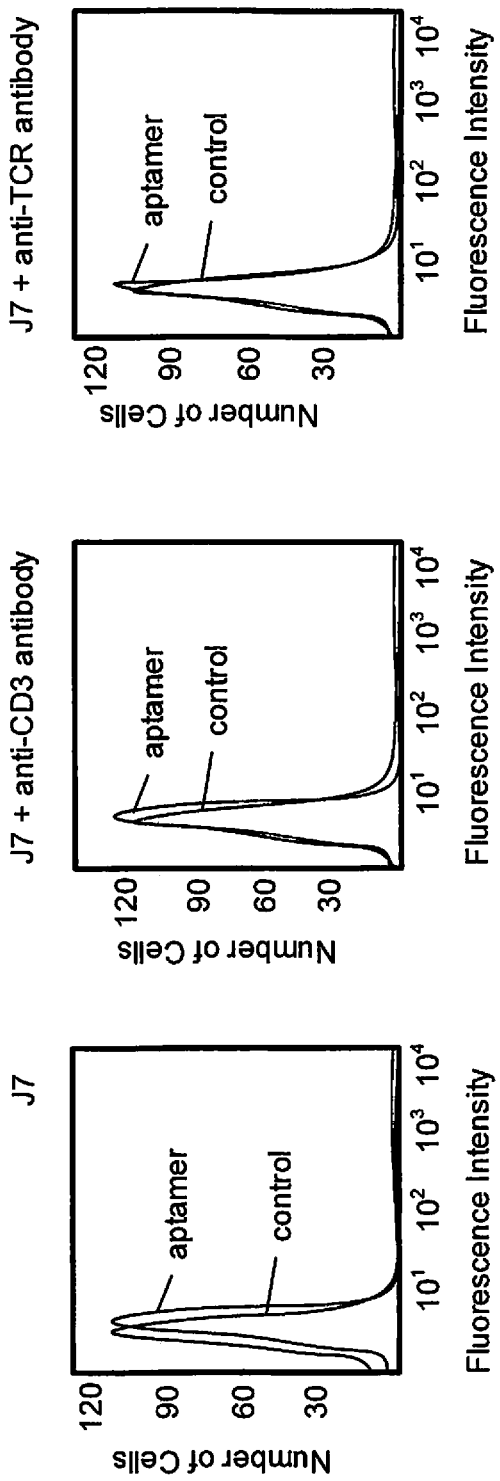

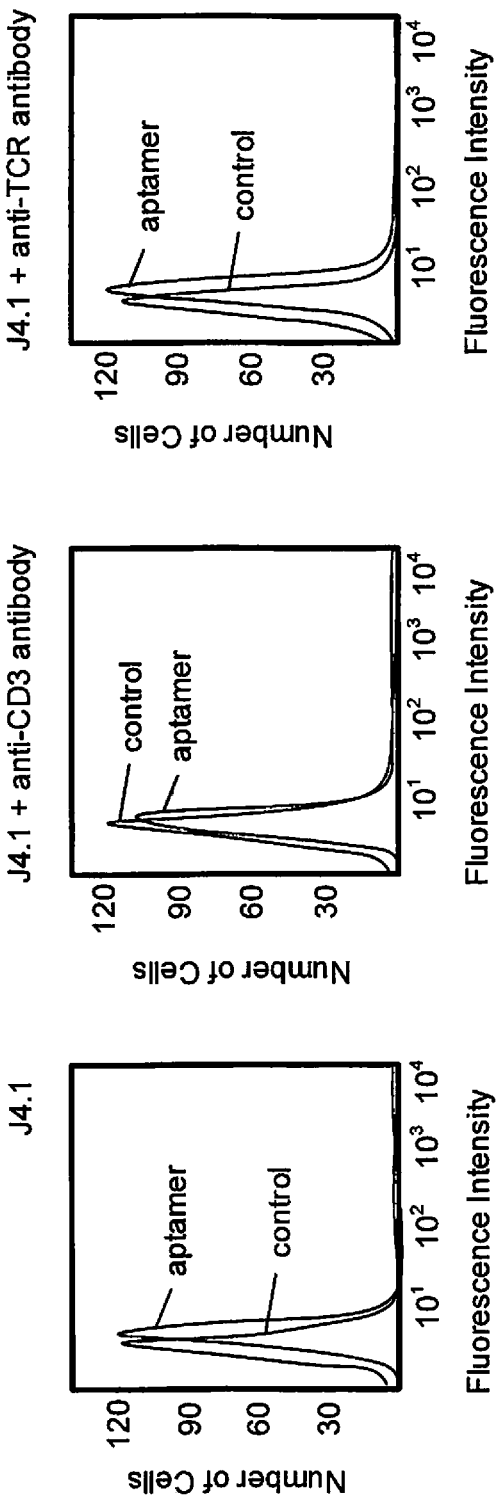

FIG. 7

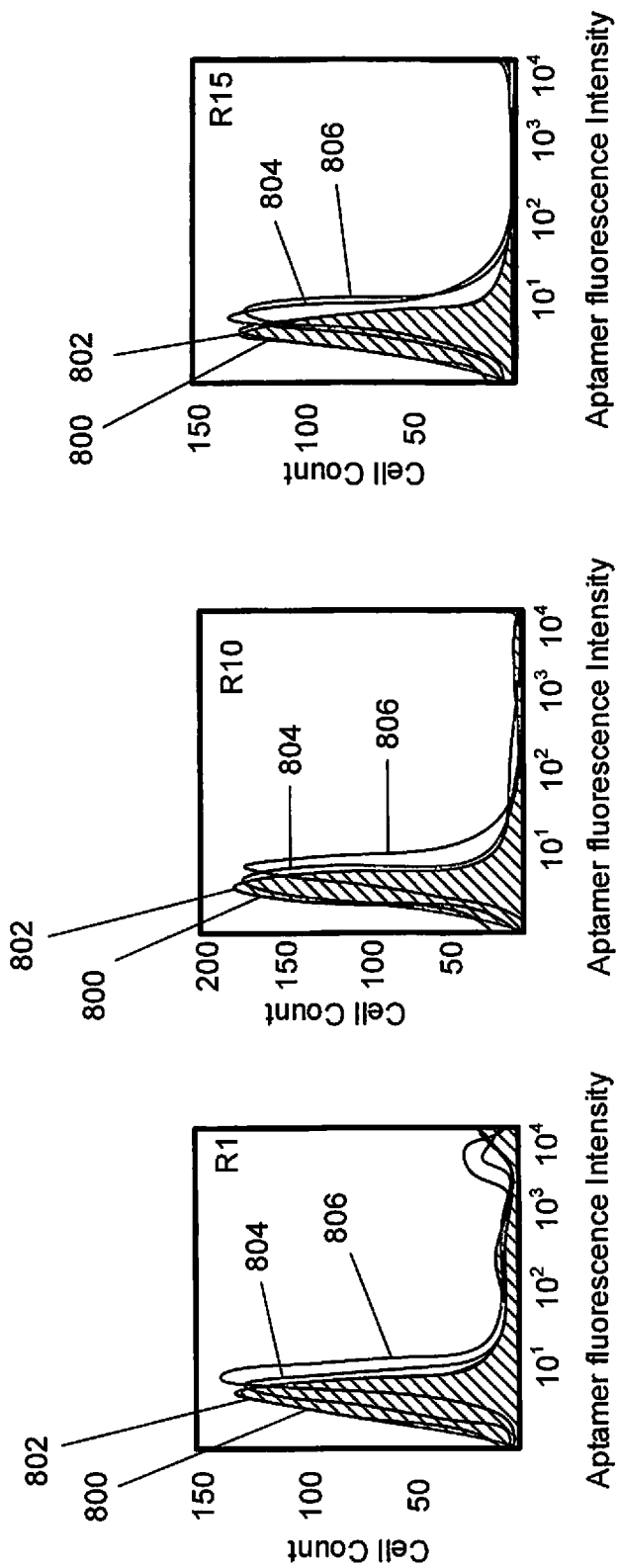

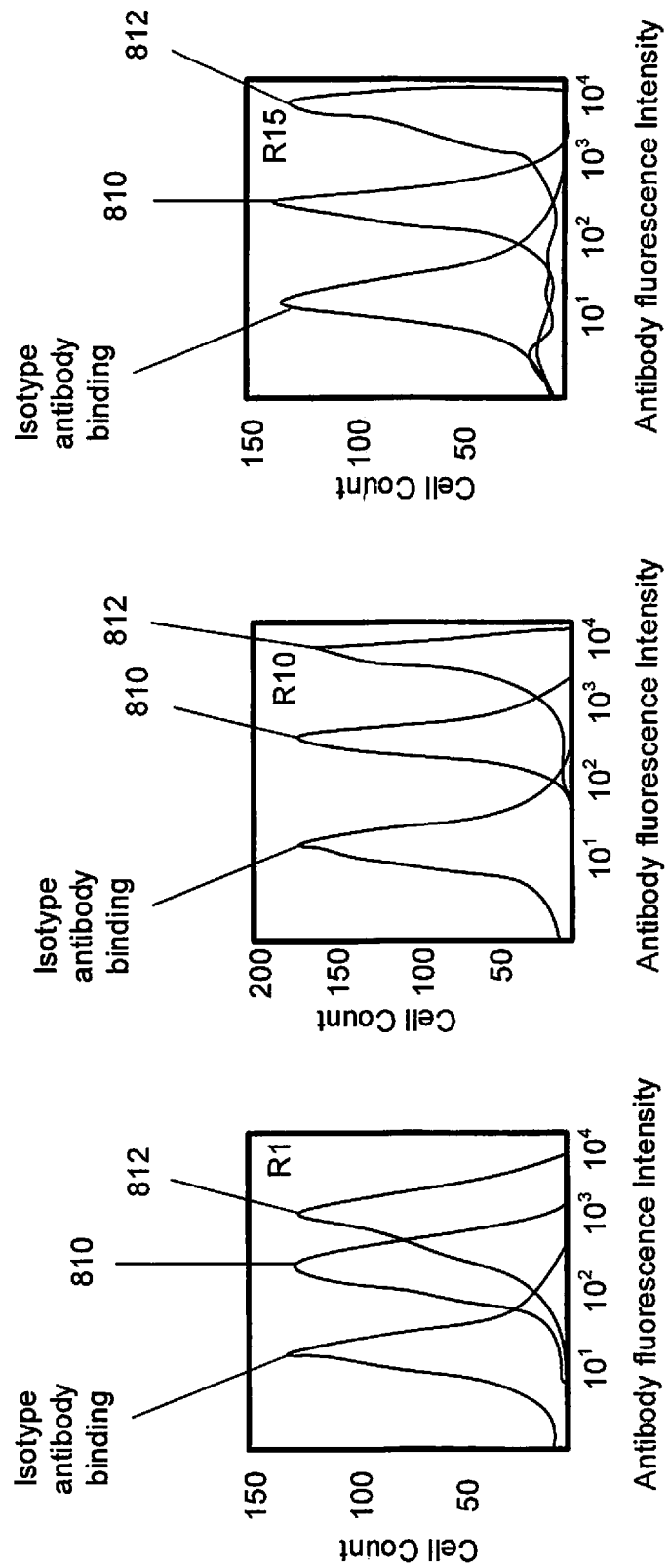

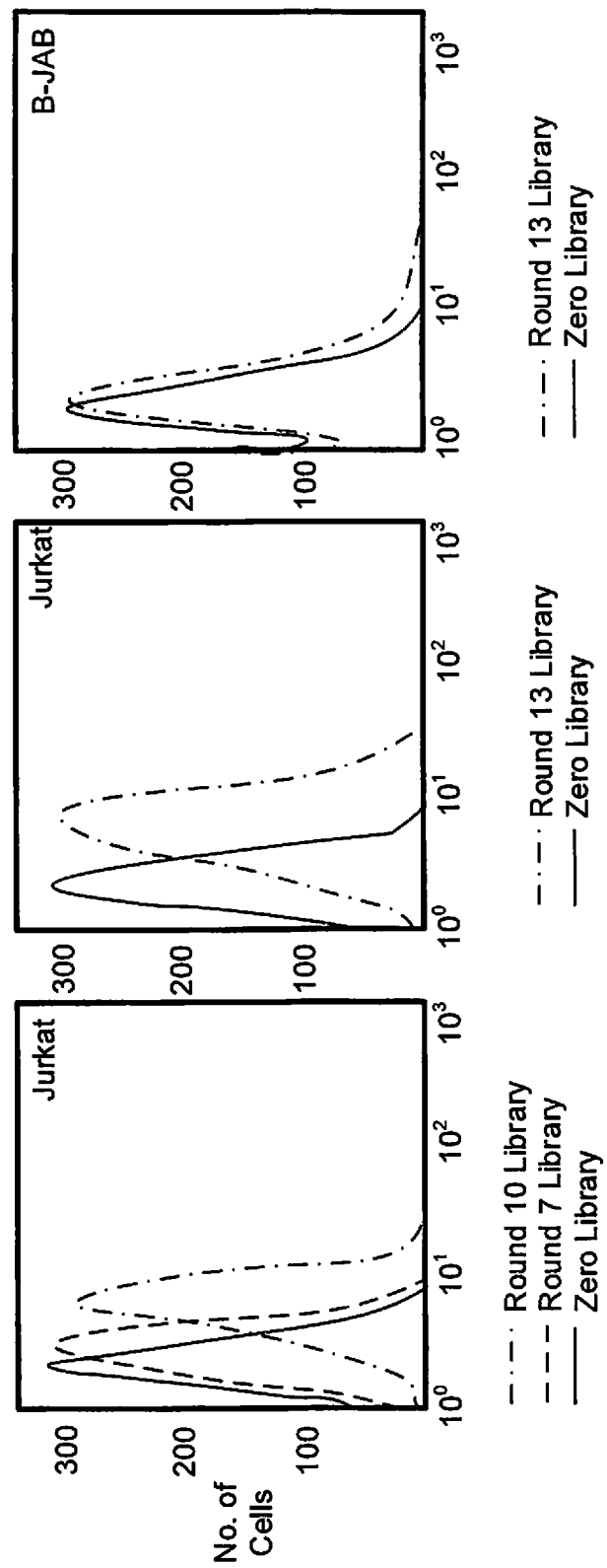

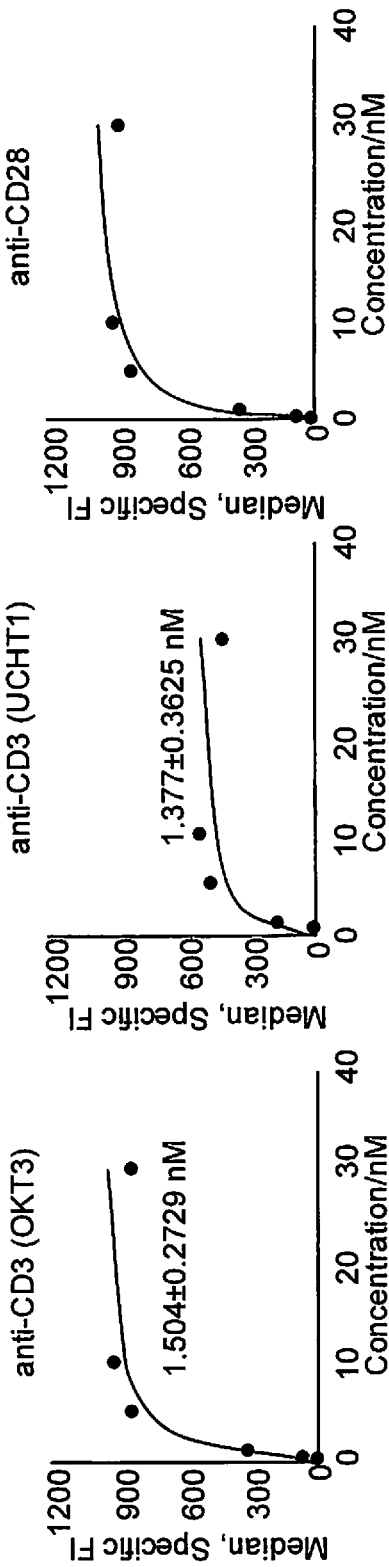

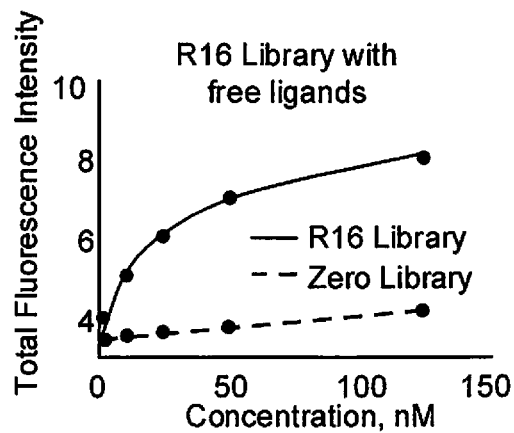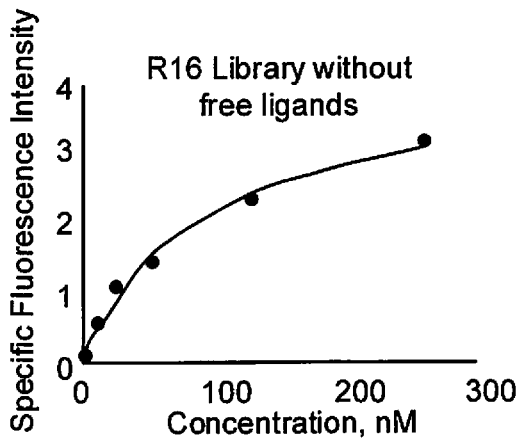
FIG. 11A  FIG. 11B
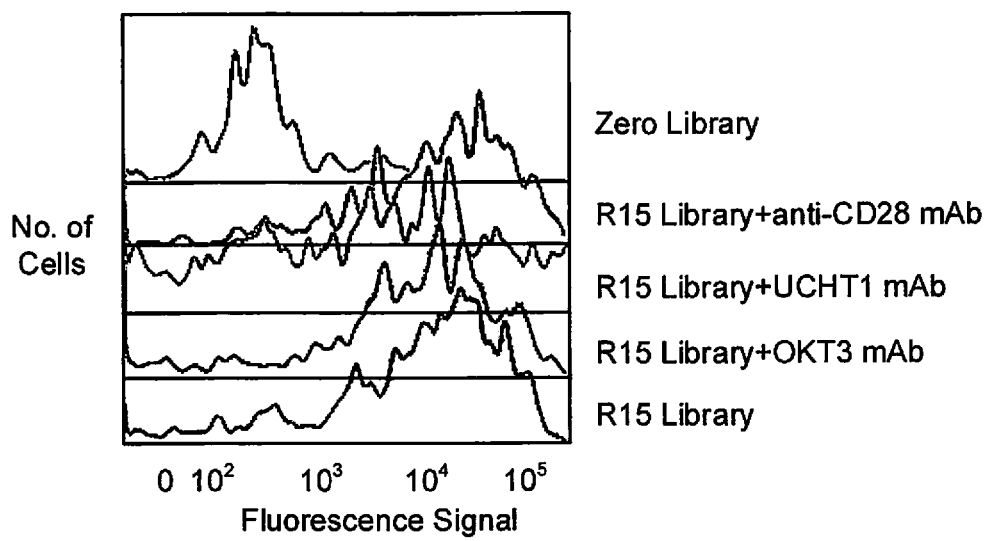
FIG. 11C

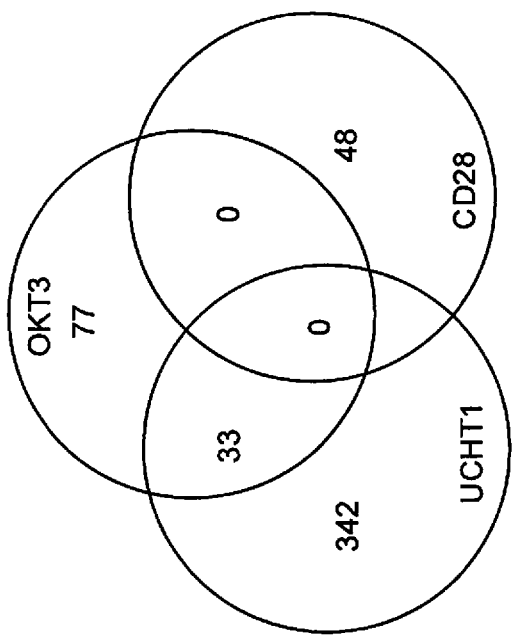

FIG. 12C

| | | | | | | | | | | | | | | | | | | | | | | | | | | | | |
|---|---|---|---|---|---|---|---|---|---|---|---|---|---|---|---|---|---|---|---|---|---|---|---|---|---|---|---|---|
| ZOKT-2 | C | C | T | T | G | G | G | T | G | G | G | T | C | T | A | G | T | G | T | T | T | C | G | G | G | G | C | T | G | 16.4±3.71 | SEQ ID NO:23 |
| ZOKT-6 | C | C | C | G | T | G | G | G | T | G | G | G | T | C | T | A | G | T | G | T | T | T | C | T | G | G | G | - | - | - | N.B. | SEQ ID NO:24 |
| ZOKT-3 | C | C | A | T | G | G | G | T | G | G | G | T | C | T | A | G | T | G | T | T | T | C | G | G | G | A | C | C | G | 27.5±5.86 | SEQ ID NO:25 |
| ZOKT-7 | C | C | C | G | T | G | G | G | T | G | G | G | T | C | T | A | G | T | G | T | T | T | C | G | T | T | G | - | - | - | N.B. | SEQ ID NO:26 |
| ZOKT-5 | C | C | G | T | G | G | G | T | G | G | G | T | C | T | A | G | T | G | T | T | T | C | G | G | G | A | C | G | G | 325±62.7 | SEQ ID NO:27 |
| ZOKT-4 | C | T | G | T | G | G | G | T | G | T | G | T | C | T | A | G | T | G | T | T | T | C | G | G | G | G | C | G | G | 52.51±11.6 | SEQ ID NO:28 |
| ZOKT-8 | C | C | C | G | G | G | G | T | G | G | G | T | C | T | A | G | T | G | T | A | T | T | T | C | G | G | G | G | C | G | G | N.B. | SEQ ID NO:29 |
| ZOKT-1 | C | C | G | C | G | G | G | T | G | G | G | T | C | T | A | G | T | G | T | T | T | A | G | G | G | G | C | G | G | 3.0±0.48 | SEQ ID NO:30 |

FIG. 12D

SEQUENCE LISTING

```
<160> NUMBER OF SEQ ID NOS: 30

<210> SEQ ID NO 1
<211> LENGTH: 45
<212> TYPE: DNA
<213> ORGANISM: Artificial Sequence
<220> FEATURE:
<223> OTHER INFORMATION: Completely synthetic sequence identified by
      LIGS from SELEX library.

<400> SEQUENCE: 1
tcggtctgtc tctatctatg ggaggtaaga actttgttcc tgatt              45

<210> SEQ ID NO 2
<211> LENGTH: 41
<212> TYPE: DNA
<213> ORGANISM: Artificial Sequence
<220> FEATURE:
<223> OTHER INFORMATION: Completely synthetic sequence from SELEX
      library.

<400> SEQUENCE: 2
gttagggtgt gtcgtcgtgg taaggagcag cgtggaggat a                  41
```

<210> SEQ ID NO 3
<211> LENGTH: 40
<212> TYPE: DNA
<213> ORGANISM: Artificial Sequence
<220> FEATURE:
<223> OTHER INFORMATION: Completely synthetic sequence from SELEX
      library.

<400> SEQUENCE: 3
ttagggtgtg tcgtcgtggt aaggagcagc gtggaggata                                40

<210> SEQ ID NO 4
<211> LENGTH: 80
<212> TYPE: DNA
<213> ORGANISM: Artificial Sequence
<220> FEATURE:
<223> OTHER INFORMATION: Completely synthetic sequence from SELEX
      library.

<400> SEQUENCE: 4
gtacactagt tatgtcccgg gtcgacatca ctgtagcggc gtcagttagg gtgtgtcgtc        60
gtggtactcg tggtgccgcc                                                    80

<210> SEQ ID NO 5
<211> LENGTH: 21
<212> TYPE: DNA
<213> ORGANISM: Artificial Sequence
<220> FEATURE:
<223> OTHER INFORMATION: Completely synthetic sequence identified by
      LIGS from SELEX library.

<400> SEQUENCE: 5
gttagggttt gtcgtcgtgg t                                                  21

<210> SEQ ID NO 6
<211> LENGTH: 38
<212> TYPE: DNA
<213> ORGANISM: Artificial Sequence
<220> FEATURE:
<223> OTHER INFORMATION: Completely synthetic sequence from SELEX
      library.

<400> SEQUENCE: 6
ttagggtgtg tcgtcgtggt aaggggtta atgaggtg                                 38

<210> SEQ ID NO 7
<211> LENGTH: 45
<212> TYPE: DNA
<213> ORGANISM: Artificial Sequence
<220> FEATURE:
<223> OTHER INFORMATION: Completely synthetic sequence identified by
      LIGS from SELEX library.

<400> SEQUENCE: 7
aaagttagct gtttcctcgt ggcagaagga acagaccacc gtact                        45

<210> SEQ ID NO 8
<211> LENGTH: 45
<212> TYPE: DNA
<213> ORGANISM: Artificial Sequence
<220> FEATURE:
<223> OTHER INFORMATION: Completely synthetic sequence from SELEX
      library.

<400> SEQUENCE: 8
tcggtaaggg tcggggatgc tacaactgtt taaacgaccc gtcca         45

<210> SEQ ID NO 9
<211> LENGTH: 45
<212> TYPE: DNA
<213> ORGANISM: Artificial Sequence
<220> FEATURE:
<223> OTHER INFORMATION: Completely synthetic sequence identified by
      LIGS from SELEX library.

<400> SEQUENCE: 9
atttaaaaca tgaggatacg aacccgtacc gctgagacgt gacca         45

<210> SEQ ID NO 10
<211> LENGTH: 27
<212> TYPE: DNA
<213> ORGANISM: Artificial Sequence
<220> FEATURE:
<223> OTHER INFORMATION: Completely synthetic sequence identified by
      LIGS from SELEX library.

<400> SEQUENCE: 10
cgaacccgta ccgctgagac gtgacca                              27

<210> SEQ ID NO 11
<211> LENGTH: 43
<212> TYPE: DNA
<213> ORGANISM: Artificial Sequence
<220> FEATURE:
<223> OTHER INFORMATION: Completely synthetic sequence from SELEX
      library.

<400> SEQUENCE: 11
cattatacca caaagtcgtg agttaagtta gtagcagacc tat            43

<210> SEQ ID NO 12
<211> LENGTH: 51
<212> TYPE: DNA
<213> ORGANISM: Artificial Sequence
<220> FEATURE:
<223> OTHER INFORMATION: Completely synthetic sequence from SELEX
      library.

<400> SEQUENCE: 12
tcccatggcc tctaacttcc aaacatacca catttaacat gaacccaact g   51

<210> SEQ ID NO 13
<211> LENGTH: 43
<212> TYPE: DNA
<213> ORGANISM: Artificial Sequence
<220> FEATURE:
<223> OTHER INFORMATION: Completely synthetic sequence identified by
      LIGS from SELEX library.

<400> SEQUENCE: 13
aacactgggt ggggttagcg ggcgatttag ggatcttgac tgg            43

<210> SEQ ID NO 14
<211> LENGTH: 42
<212> TYPE: DNA
<213> ORGANISM: Artificial Sequence
<220> FEATURE:
<223> OTHER INFORMATION: Completely synthetic sequence identified by
      LIGS from SELEX library.

<400> SEQUENCE: 14
cgccggtgtt gacgaaacgg gatggggagc gcggggaccg ga             42

-continued

<210> SEQ ID NO 15
<211> LENGTH: 43
<212> TYPE: DNA
<213> ORGANISM: Artificial Sequence
<220> FEATURE:
<223> OTHER INFORMATION: Completely synthetic sequence identified by
      LIGS from SELEX library.

<400> SEQUENCE: 15
gggtggagag gtggaggcgt ggagagaacg ggaaggctca gca                     43

<210> SEQ ID NO 16
<211> LENGTH: 10
<212> TYPE: DNA
<213> ORGANISM: Artificial Sequence
<220> FEATURE:
<223> OTHER INFORMATION: Completely synthetic sequence from SELEX
      library.

<400> SEQUENCE: 16
ggataggggg                                                          10

<210> SEQ ID NO 17
<211> LENGTH: 51
<212> TYPE: DNA
<213> ORGANISM: Artificial Sequence
<220> FEATURE:
<223> OTHER INFORMATION: Completely synthetic sequence identified by
      LIGS from SELEX library.

<400> SEQUENCE: 17
ctaaacagaa ggggtcggtc ggtctggcgc ggacctcgag tcatggtggg t            51

<210> SEQ ID NO 18
<211> LENGTH: 76
<212> TYPE: DNA
<213> ORGANISM: Artificial Sequence
<220> FEATURE:
<223> OTHER INFORMATION: synthetic SELEX libary flanked by two primers
<220> FEATURE:
<221> NAME/KEY: variation
<222> LOCATION: (22)..(58)
<223> OTHER INFORMATION: A, G, C or T
<220> FEATURE:
<221> NAME/KEY: misc_feature
<222> LOCATION: (22)..(58)
<223> OTHER INFORMATION: n is a, c, g, or t

<400> SEQUENCE: 18
atcgtctgct ccgtccaata annnnnnnnn nnnnnnnnnn nnnnnnnnn nnnnnnnntt    60 tggtgtgagg tcgtgc                                                   76

<210> SEQ ID NO 19
<211> LENGTH: 20
<212> TYPE: DNA
<213> ORGANISM: Artificial Sequence
<220> FEATURE:
<223> OTHER INFORMATION: Synthetic forward primer

<400> SEQUENCE: 19
atcgtctgct ccgtccaata                                               20

<210> SEQ ID NO 20
<211> LENGTH: 18
<212> TYPE: DNA
<213> ORGANISM: Artificial Sequence

```
<220> FEATURE:
<223> OTHER INFORMATION: synthetic reverse primer

<400> SEQUENCE: 20
gcacgacctc acaccaaa                                                    18

<210> SEQ ID NO 21
<211> LENGTH: 53
<212> TYPE: DNA
<213> ORGANISM: Artificial Sequence
<220> FEATURE:
<223> OTHER INFORMATION: synthetic forward amplicon

<400> SEQUENCE: 21
tcgtcggcag cgtcagatgt gtataagaga cagatcgtct gctccgtcca ata             53

<210> SEQ ID NO 22
<211> LENGTH: 52
<212> TYPE: DNA
<213> ORGANISM: Artificial Sequence
<220> FEATURE:
<223> OTHER INFORMATION: synthetic reverse amplicon

<400> SEQUENCE: 22
gtctcgtggg ctcggagatg tgtataagag acaggcacga cctcacacca aa              52

<210> SEQ ID NO 23
<211> LENGTH: 37
<212> TYPE: DNA
<213> ORGANISM: Artificial Sequence
<220> FEATURE:
<223> OTHER INFORMATION: Aptamer sequence

<400> SEQUENCE: 23
ccttggggtg ggtctagtgt ggatgtttcg ggggctg                               37

<210> SEQ ID NO 24
<211> LENGTH: 33
<212> TYPE: DNA
<213> ORGANISM: Artificial Sequence
<220> FEATURE:
<223> OTHER INFORMATION: Aptamer sequence

<400> SEQUENCE: 24
ccgtggggtg ggtctagtgt ggatgtttct ggg                                   33

<210> SEQ ID NO 25
<211> LENGTH: 37
<212> TYPE: DNA
<213> ORGANISM: Artificial Sequence
<220> FEATURE:
<223> OTHER INFORMATION: Aptamer sequence

<400> SEQUENCE: 25
ccatggggtg ggtctagtgt ggatgtttcg gggaccg                               37

<210> SEQ ID NO 26
<211> LENGTH: 33
<212> TYPE: DNA
<213> ORGANISM: Artificial Sequence
<220> FEATURE:
<223> OTHER INFORMATION: Aptamer sequence

<400> SEQUENCE: 26
ccgtggggtg ggtctagtgt ggatgtttcg ttg                                   33
```

```
<210> SEQ ID NO 27
<211> LENGTH: 37
<212> TYPE: DNA
<213> ORGANISM: Artificial Sequence
<220> FEATURE:
<223> OTHER INFORMATION: Aptamer sequence

<400> SEQUENCE: 27
ccgtcgggtg ggtctagtgt ggatgtttcg gggacgg                                37

<210> SEQ ID NO 28
<211> LENGTH: 37
<212> TYPE: DNA
<213> ORGANISM: Artificial Sequence
<220> FEATURE:
<223> OTHER INFORMATION: Aptamer sequence

<400> SEQUENCE: 28
ctgtggtgtg ggtctagtgt ggatgtttcg ggggcgg                                37

<210> SEQ ID NO 29
<211> LENGTH: 37
<212> TYPE: DNA
<213> ORGANISM: Artificial Sequence
<220> FEATURE:
<223> OTHER INFORMATION: Aptamer sequence

<400> SEQUENCE: 29
ccgtggtgtg ggtctagtgt gtatgtttcg ggggcgg                                37

<210> SEQ ID NO 30
<211> LENGTH: 37
<212> TYPE: DNA
<213> ORGANISM: Artificial Sequence
<220> FEATURE:
<223> OTHER INFORMATION: Aptamer sequence

<400> SEQUENCE: 30
ccgcggggtg ggtctagtgt ggatgtttag ggggcgg                                37
```

LIGAND-GUIDED-SELECTION METHOD FOR SCREENING ANTIGEN-SPECIFIC LIGANDS

CROSS-REFERENCE TO RELATED APPLICATIONS

This application claims priority to and is a continuation-in-part of U.S. patent application Ser. No. 15/097,845 (filed Apr. 13, 2016) which is a non-provisional of U.S. Patent Application 62/146,472 (filed Apr. 13, 2015); U.S. Patent Application 62/253,963 (filed Nov. 11, 2015) and U.S. Patent Application 62/320,793 (filed Apr. 11, 2016) the entirety of which are incorporated herein by reference.

STATEMENT OF FEDERALLY SPONSORED RESEARCH OR DEVELOPMENT

This invention was made with government support under contract number SC3GM105578 and SC1 GM122648 awarded by the National Institute of Health (NIH). The government has certain rights in the invention.

REFERENCE TO A SEQUENCE LISTING

This application refers to a "Sequence Listing" listed below, which is provided as an electronic document entitled "RESE17305RO_ST25.txt" (5 kb created on Apr. 12, 2016) which is incorporated herein by reference in its entirety.

BACKGROUND OF THE INVENTION

The subject matter disclosed herein relates to methods for screening for an aptamer. Aptamers are small synthetic nucleic acid strands that specifically bind to a target molecule with high affinity. One conventional method of aptamer selection is known as SELEX (Systematic Evolution of Ligands by Exponential enrichment). SELEX allows the screening of oligonucleotides against a variety of target ligands via an iterative and evolutionary process of continuous enrichment to identify target-specific binders. A typical SELEX library is vastly heterogeneous with a large number of distinct nucleic acid molecules (approximately $10^{13}$ molecules). Each molecule folds into a unique secondary structure, which leads to a distinct geometrical shape. Depending on shape complementarity and non-covalent electrostatic or hydrophobic interactions, a few DNA sequences can specifically bind to the desired target. Subsequently, bound sequences are separated and amplified using Polymerase Chain Reaction (PCR) to generate an evolved library. The process is repeated until high-affinity binders are enriched, resulting in a homogeneous library with high-affinity nucleic acid aptamers against the target of interest. SELEX has resulted in generating a significant number of aptamers against targets ranging from small molecules to whole cells; however, translational applications have been limited. To increase the clinical practicality of aptamer selection, development of methods to identify aptamers that could specifically recognize predetermined antigens in their endogenous state with no prior- or post SELEX sample manipulations on receptor proteins is desirable.

The discussion above is merely provided for general background information and is not intended to be used as an aid in determining the scope of the claimed subject matter.

BRIEF DESCRIPTION OF THE INVENTION

A "Ligand-guided-Selection" (LIGS) method for identifying highly specific aptamers against a predetermined antigen of a target is provided. LIGS uses a stronger and highly specific binder (e.g. an antibody) interacting with its cognate antigen to displace specific aptamers from a partially enriched SELEX pool. Elution of the displaced aptamers provides aptamers that are specific to the predetermined antigen. An advantage that may be realized in the practice of some disclosed embodiments of the method is that it enables identification of one or more aptamers that is specific to a predetermined antigen on a given cell line.

In a first embodiment, a Ligand-guided-Selection method for screening ligands that are specific to an antigen is provided. The method comprises sequential steps of forming a ligand-cell complex by exposing a culture of target cells to a library of ligands, wherein cells in the culture of target cells each have an antigen; treating the ligand-cell complex with a predetermined ligand that is specific to the antigen, the predetermined ligand displacing ligands that are bound to the antigen to form displace ligands; eluting the displaced ligands; and amplifying the displaced ligands.

In a second embodiment, a Ligand-guided-Selection method for screening ligands that are specific to an antigen is provided. The method comprises sequential steps of evolving a library of ligands by exposing a target cell line to an aptamer library and permitting at least some aptamers to bind to the target cell line, thereby forming bound aptamers; removing aptamers that do not bind to the target cell line; eluting the bound aptamers, thereby forming eluted aptamers; amplifying the eluted aptamers that are specific to the cell line, thereby forming the library of ligands. A ligand-cell complex is formed by exposing a culture of target cells to the library of ligands, wherein cells in the culture of target cells each have an antigen; treating the ligand-cell complex with an antibody that is specific to the antigen, the antibody displacing ligands that are bound to the antigen to form displace ligands; eluting the displaced ligands; amplifying the displaced ligands.

In a third embodiment, a method for selecting aptamers using an antibody-capped cell Systematic Evolution of Ligands by EXponential enrichment process is provided. The method comprising steps of exposing an antibody-capped cell to a plurality of different aptamers and permitting at least some aptamers to bind to the antibody-capped cell to form bound aptamers, wherein the antibody-capped cell has been pretreated with an antibody that caps an antigen; eluting unbound aptamers; and amplifying the unbound aptamers.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings are not necessarily to scale, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which:

FIG. 5 is a sequence alignment showing patterns in aptamers identified by LIGS for CD3ε expressed on T lymphocytes compared to select aptamers from the SELEX pool;

FIG. 6A, FIG. 6B and FIG. 6C are flow cytometric competitive binding analysis of J7 without anti-CD3ε (FIG. 6A), with anti-CD3ε (FIG. 6B) and anti-TCRαβ antibody (FIG. 6C);

FIG. 6D, FIG. 6E and FIG. 6F are flow cytometric competitive binding analysis of J4.1 without anti-CD3ε (FIG. 6D), with anti-CD3ε (FIG. 6E) and anti-TCRαβ antibody (FIG. 6F);

FIG. 7 is a sequence alignment showing patterns in aptamers identified by LIGS for IgM expressed on Burkitt's lymphoma cells compared to select aptamers from the SELEX pool;

FIG. 8A, FIG. 8B and FIG. 8C depict the results of flowcytometric competitive binding analysis of R1, R10 and R15, respectively, in the presence of IgM or in the presence of anti-CD20; and FIG. 8D, FIG. 8E and FIG. 8F show anti-IgM and anti-CD20 Ab on the binding of the aptamer for with Ramos cells during competition experiments with R1 (FIG. 8D), R10 (FIG. 8E) and R15 (FIG. 8F);

FIG. 9A is a graph showing an analysis from flow cytometry showing an enrichment of DNA ligands towards Jurkat.E6 cells after 10 rounds of cell-SELEX;

FIG. 9B and FIG. 9C are graphs depicting a specific enrichment of DNA ligands towards Jurkat.E6 cells but not towards BJAB cells after 13 rounds of cell-SELEX;

FIG. 10A, FIG. 10B and FIG. 10C depict the results of an affinity analysis of OKT3, UCHT1 and anti-CD28 antibodies against Jurkat.E6 cells at 25° C. All three mAbs were incubated at 0.04 nM, 0.2 nM, 1 nM, 5 nM 10 nM and 30 nM final concentrations and isotype control (clone MOPC-21) at 30 nM concentration with $2.0 \times 10^5$ cells for 45 min. Secondary antibody staining was performed after washing by using ALEXA FLUOR® 647-conjugated Goat anti-Mouse IgG at a final concentration of 5 μg/mL with an incubation time of 30 min on ice. $K_d$ values were obtained by plotting the specific median fluorescence intensities against each concentration on GraphPad Prism software using one-site specific binding;

FIG. 11A shows an affinity analysis of enriched pool towards Jurkat.E6 cells at round 16 of cell-SELEX in the presence of free ligands, which was found to be 19.55±1.957 nM;

FIG. 11B shows an affinity analysis of enriched pool towards Jurkat.E6 cells at round 16 of cell-SELEX in the absence of free ligands, which was found to be 78.28±14.34 nM;

FIG. 11C shows an analysis of flow cytometry data obtained for LIGS against T-cells isolated from PBMCs.

FIG. 12C illustrates Venn-diagrams summarizing the findings as represented in 3B;

FIG. 12D depicts multiple sequences alignment of the aptamer family, where the exceptional sequences are highlighted in gray. Dissociation constant for each aptamer is given {N.B.=not binding);

DETAILED DESCRIPTION OF THE INVENTION

Figure 1:
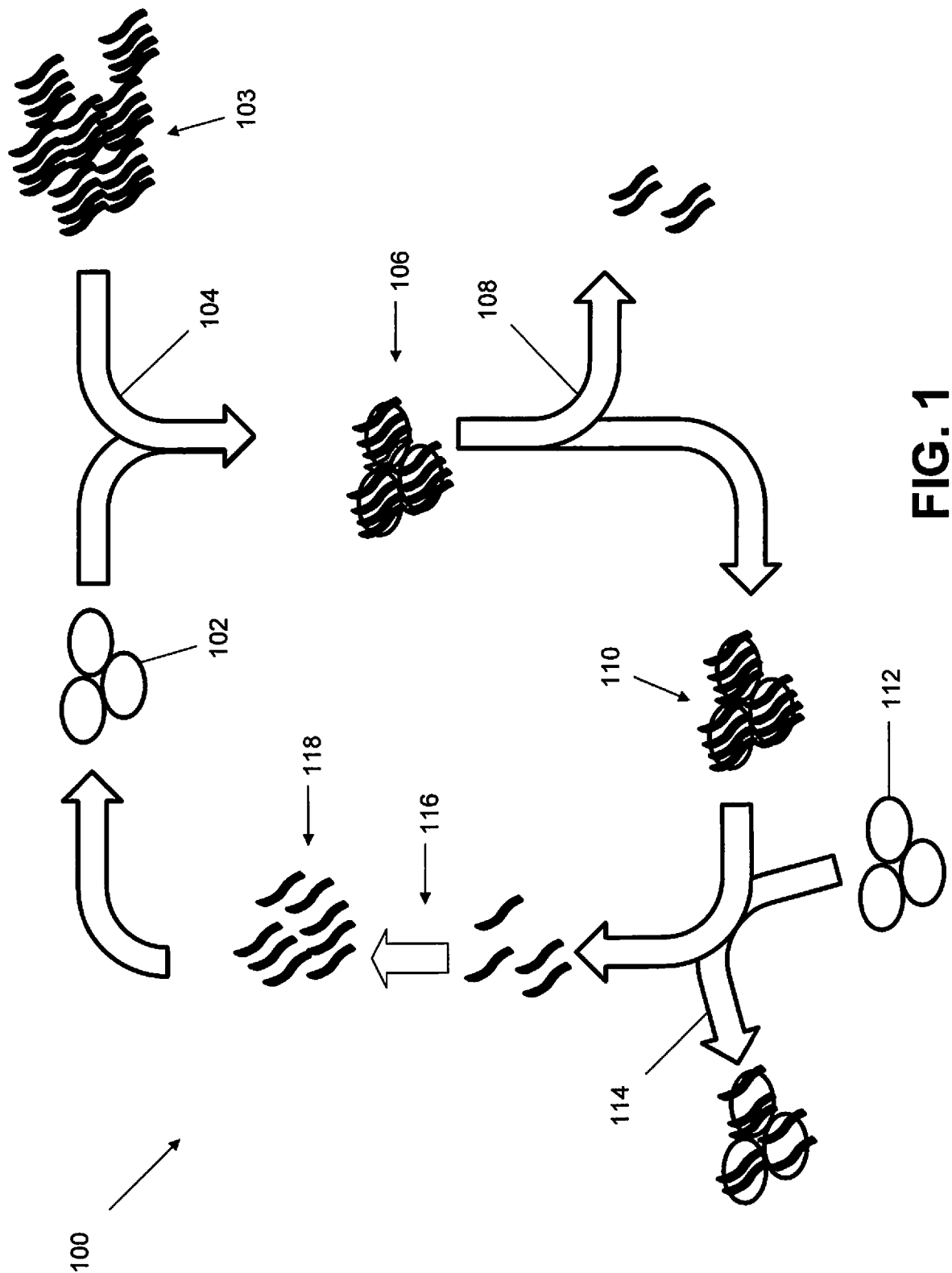
FIG. 1 is a schematic flow diagram of a cell-SELEX method.

Disclosed in this specification is a method referred to as Ligand-guided Selection, (LIGS), which allows identification of aptamers specific for a predetermined antigen expressed on a cell surface. LIGS interrupts the cell-SELEX process at the stage of enrichment of a SELEX library and introduces a secondary, pre-existing ligand (e.g. an antibody) to outcompete and elute aptamers specific for the membrane receptor of the secondary ligand. LIGS introduces a stronger, known high-affinity ligand against the target of interest to achieve two purposes: 1) to directly outcompete and replace aptamers specific towards the antigen of interest and 2) to introduce structural changes on the target protein upon binding of the ligand to outcompete specific aptamers. Based on the specificity of the ligand towards its antigen, the aptamers identified by LIGS show higher specificity towards the antigen than those succeeding as cell-specific binders via cell-SELEX.

The cell-SELEX method allows the selection of aptamers towards membrane receptor targets in their native state at their endogenous levels with no prior requirement for the overexpression of a protein. Nevertheless, proteomic identification of the receptor protein ligand of aptamers generated from cell-SELEX is a challenge. With such limitation, therapeutic and diagnostic applications of aptamers remain challenging. Therefore, to address this challenge, LIGS is introduced as a simple technique to selectively separate aptamers binding to a specific antigen using a ligand specific to the same antigen. From a fundamental point-of-view, LIGS technology pushes separation efficiency to a remarkably high level. That is, the competition strategy allows us to separate out a few aptamer molecules that bind to a specific antigen of a specific receptor molecule in its endogenous state from a complex library evolved against a whole cell. Since the aptamers selected using LIGS are selectively eluted based on the interaction of the ligand with its target antigen at its endogenous state, LIGS-generated aptamers have higher potential in identifying same antigen in a clinical setting. Moreover, apart from selecting aptamers against antigens in a multidomain protein complex, LIGS can be applied to a number of platforms, such as aptamer binding toward active sites of an enzyme, utilizing the enzyme substrate as a guide, or growth factor binding sites, utilizing growth factor interacting with receptor protein as a guide, hormones and signaling molecules that trigger protein conformation e.g. GPCR family of receptors. Aptamers can also be selected toward a small-molecule ligand-binding site, utilizing small-molecule ligand-receptor interaction as a guide. That LIGS can identify aptamers against one single domain of a multidomain system demonstrates the significance of LIGS in generating highly specific nucleic acid ligands toward a broader range of receptor molecules already characterized as surface markers. This approach can be extended to a number of combinatorial screening platforms, including phage-display libraries and small-molecule libraries.

A schematic depiction of a traditional cell-SELEX method 100 is shown in FIG. 1. Cells 102 are subjected to an incubation and selection step 104 wherein the cells 102 are exposed to a SELEX library 103 of aptamers. A select number of these aptamers bind to the cells 102 to form a bound complex 106. Unbound aptamers are removed in washing step 108 to leave a washed, bound complex 110. The washed, bound complex 110 is exposed to cells 112 that are different than the cells 102. Bound aptamers competitively bind to either the cells 102 or the cells 112 such that aptamers with a low binding affinity for the cells 102 can accumulate on the cells 112 and can be removed in step 114. High binding affinity aptamers remain on the cells 102 and are subsequently eluted to provide isolated aptamers 116. PCR may be used to amplify the resulting aptamers and, in this fashion, an evolved cell-SELEX library 118 is constructed. The resulting evolved cell-SELEX library 118 is specific for the cells 102.

Figure 2:
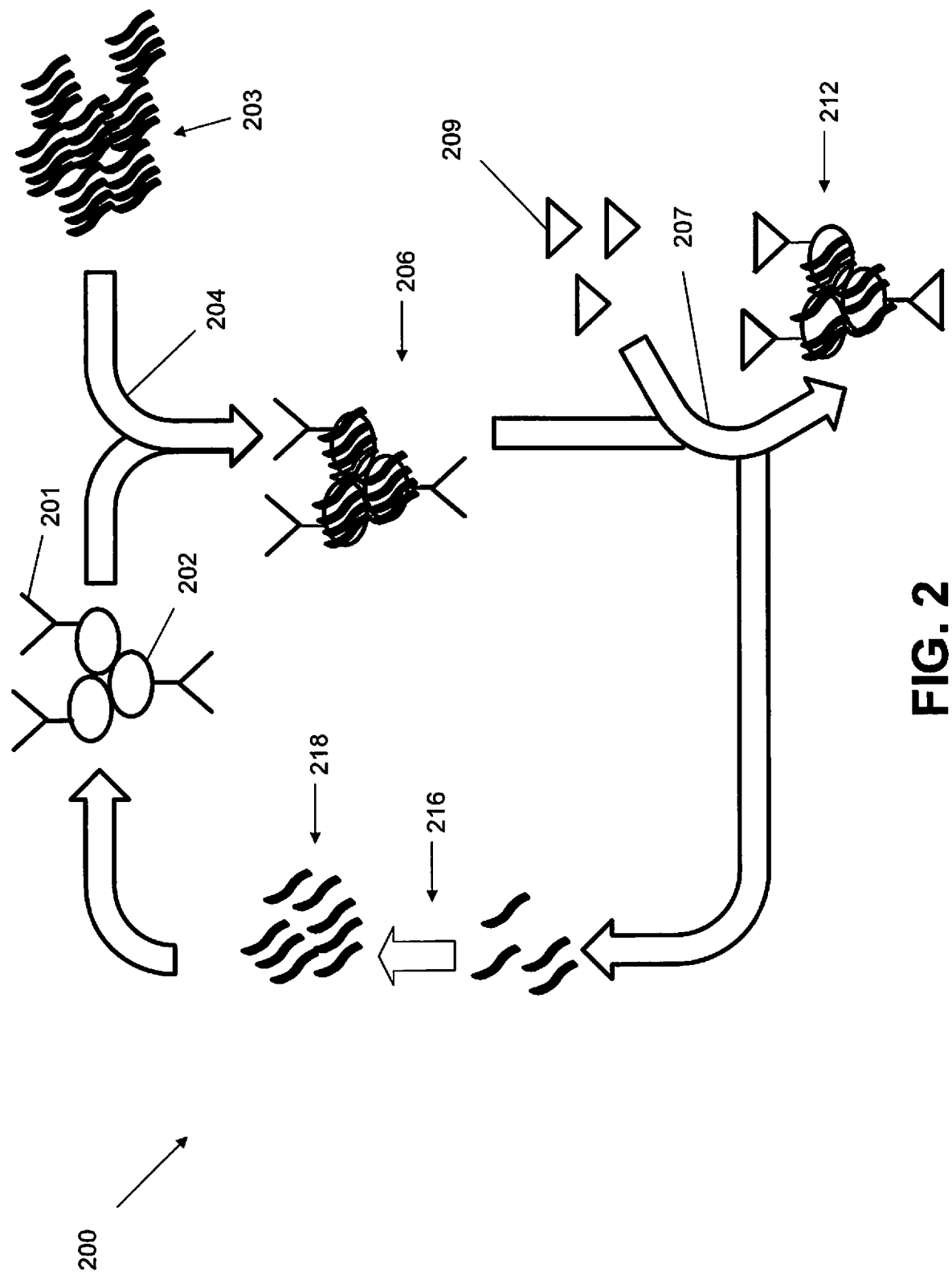
FIG. 2 is a schematic flow diagram of a LIGS method.

A schematic depiction of a LIGS method 200 is shown in FIG. 2. Positive cells 202 that are positive for a target antigen 201 are subjected to an incubation and selection step 204 wherein the positive cells 202 are exposed to a SELEX library 203 of aptamers. In one embodiment, the SELEX library of aptamers has been pre-screened using a conventional SELEX method (e.g. cell-SELEX). A select number of these aptamers bind to the positive cells 202 to form a bound complex 206.

In step 207 the bound complex 206 is exposed to a high affinity ligand 209 that is known to preferentially bind to the target antigen 201 to form a ligand-cell complex 212. Examples of high affinity ligands include antibodies, small organic molecules and ions. In one embodiment, the high-affinity ligand has a molecular weight between 65 kDa and 150 kDa. In one embodiment, the high-affinity ligand has a molecular weight of greater than 150,000 g per mole. In one embodiment, the high-affinity ligand has a molecular weight of greater than 200,000 g per mole. In another embodiment, the high affinity ligand is a small molecule with molecular weight greater than 400 g per mol. In another embodiment, the high affinity ligand is an ion with molecular weight greater than 1 g per mol. This binding displaces high binding affinity aptamers 216 while leaving other aptamers bound to the ligand-cell complex 212. In one embodiment, the displacement occurs through a competitive displacement mechanism where binding occurs at the same epitope of the antigen. In another embodiment, the displacement occurs due to a conformational change in the antigen that is induced by the binding of the high binding affinity aptamers 216 at a location other than the epitope of the antigen. The high binding affinity ligand 209 are added in excess relative to the antigen 201. In one embodiment at least a two-fold molar excess is used. In another embodiment, at least a five-fold excess is used. In yet another embodiment, at least a ten-fold molar excess is used. The high affinity binding aptamers 216 are eluted to separate them from the ligand-cell complex 212 and any aptamers bound thereto.

PCR may be used to amplify the resulting high binding affinity aptamers 216 and, in this fashion, a library 218 is constructed. The library 218 are aptamers that are specific to the target antigen 201 which are subset of the aptamers that are specific to positive cells 202. In one embodiment, the LIGS method 200 is repeated one or more times to further refine the number of aptamers in the resulting library. The resulting aptamers may then be isolated by conventional methods.

Figure 3:
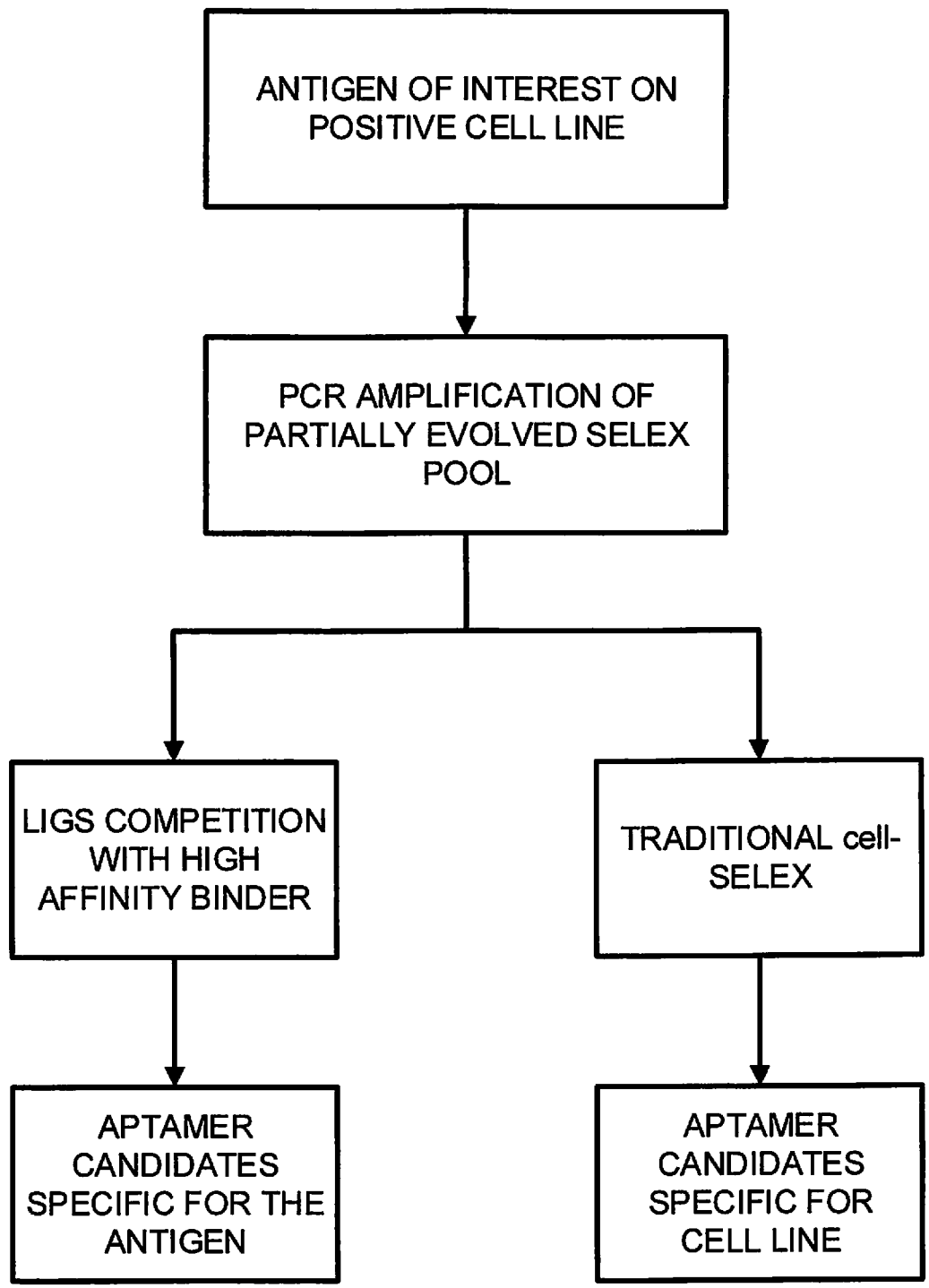
FIG. 3 is a schematic comparison of outputs of cell-SELEX and LIGS.

As graphically depicted in FIG. 3, the traditional cell-SELEX methodology provides aptamers that are specific for a given cell line. In contrast, the disclosed LIGS methodology provides aptamers that are specific for a given antigen.

Figure 4:
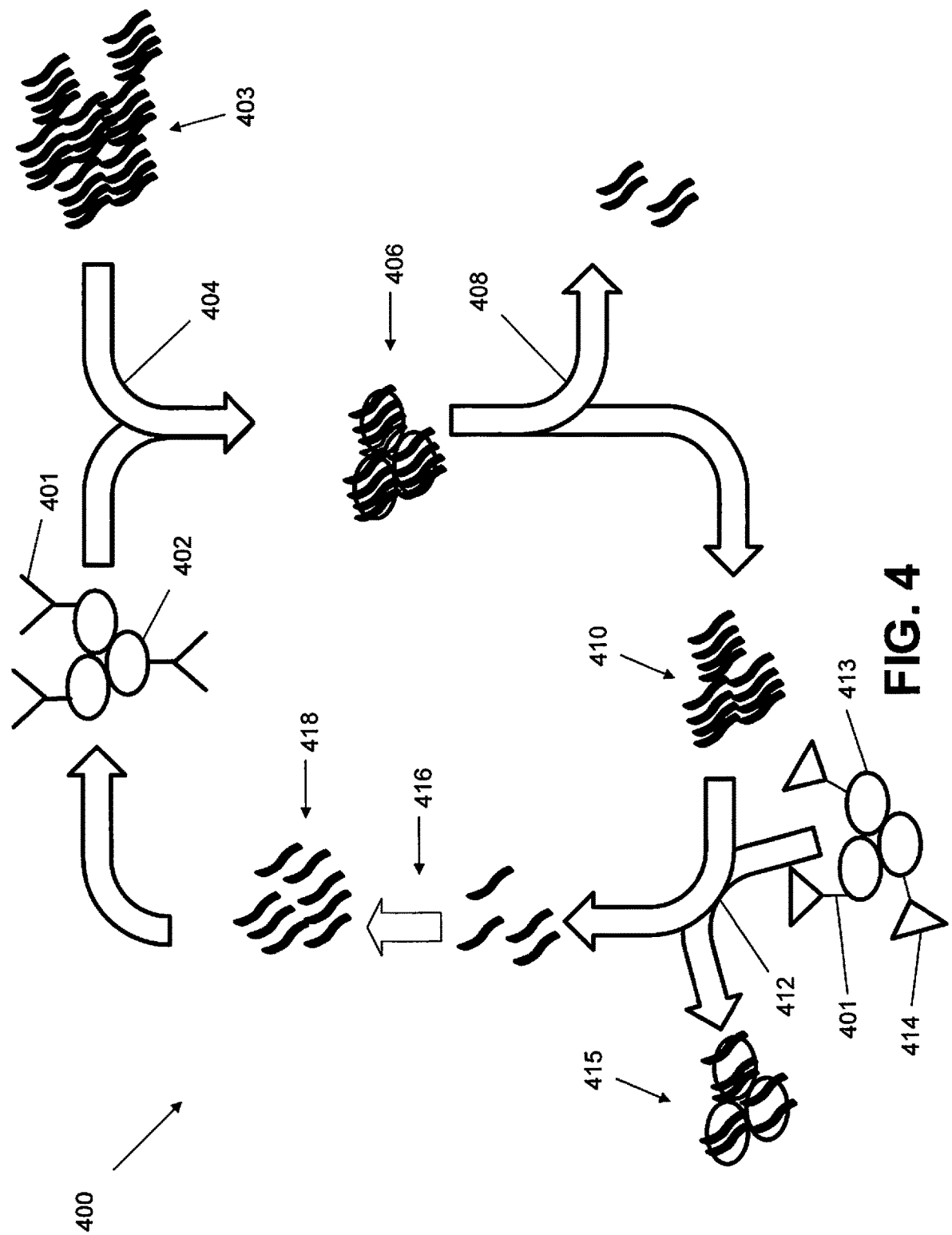
FIG. 4 is a schematic flow diagram of a LIGS method that uses antibody capping.
Figure 6I:
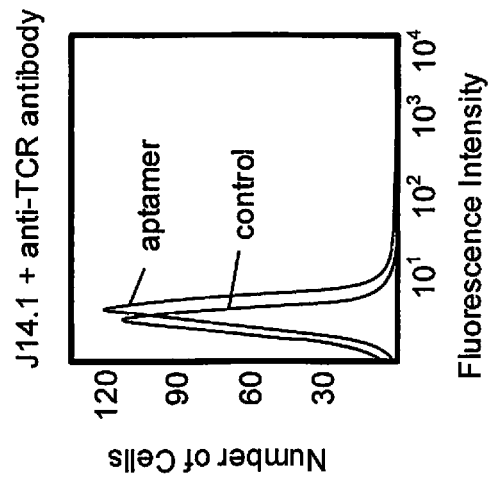
FIG. 6G, FIG. 6H and FIG. 6I are flow cytometric competitive binding analysis of J14.1 without anti-CD3ε (FIG. 6G), with anti-CD3ε (FIG. 6H) and anti-TCRαβ antibody (FIG. 6I)
Figure 6H:
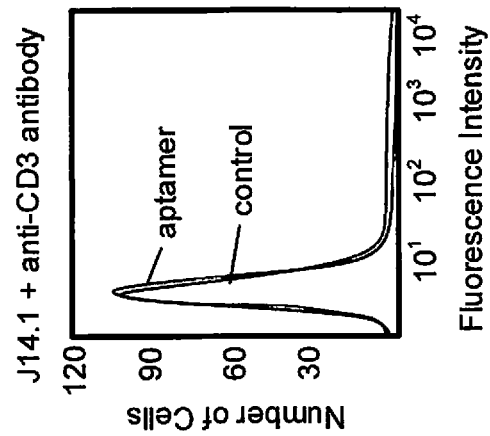
Figure 6G:
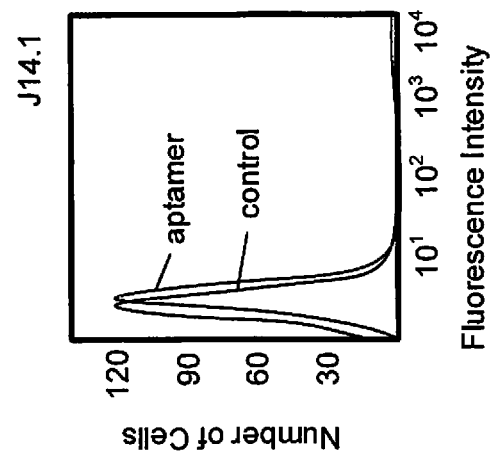

FIG. 4 depicts an antibody capped method 400. Positive cells 402 that are positive for a target antigen 401 are subjected to an incubation and selection step 404 wherein the positive cells 402 are exposed to a SELEX library 403 of aptamers. In one embodiment, the SELEX library of aptamers has been pre-screened using a conventional SELEX method (e.g. cell-SELEX). A select number of these aptamers bind to the positive cells 402 to form a bound complex 406. Unbound aptamers are removed in washing step 408 and bound aptamers are subsequently eluted to produce partially screened aptamers 410.

In step 412 the partially screened aptamers 410 are exposed to cells 413. Cells 413 are positive for antigen 401 but antigen 401 has been capped with antibody 414. Aptamers bind to the cell 413 to form complex 415 and thereby selectively remove aptamers except for aptamers 416 which are prevented from binding due to the presence of antibody 414. PCR may be used to amplify the resulting high binding affinity aptamers 416 and, in this fashion, a library 418 is constructed. The library 418 are aptamers that are specific to the target antigen 401 which are subset of the aptamers that are specific to positive cells 402.

In one embodiment, a sequence alignment strategy is used to identify aptamer sequences that were not identified by LIGS but are (1) structurally similar to aptamers identified by LIGS and (2) were identified by SELEX. Sequences obtained from sequencing cell-SELEX pool and sequences obtained from LIGS pools are aligned to identify aptamer candidates specific for the antigen. This alignment strategy is designed to address/identify aptamers that might not be outcompeted by a secondary ligand but binding to same surface marker. By aligning multiple pools similar aptamer sequences belonging to the same family are shown. If the sequence repeated multiple times in LIGS library this is considered an indication that the repeated sequence may be a desirable aptamer. In one such embodiment, the sequence is repeated at least four times. If a sequence show segments of bases spanning 5 bases to 10 bases from either library that sequence is a hit.

Example 1: CD3ε Expressed on T Lymphocytes

LIGS was used to identify aptamers against CD3ε expressed on T lymphocytes from a partially enriched SELEX library against a whole cell. CD3ε is one of the ectodomains of the T-cell receptor (TCR) complex expressed on T-cells. Using high-affinity anti-CD3 antibody against a specific antigen on the CD3ε chain as the secondary ligand, three specific aptamers against CD3ε domain were successfully identified.

The expression of CD3ε on Jurkat.E6 cells was confirmed by flow cytometry using a fluorescently labeled anti-CD3ε antibody. The selection library had 45 randomized nucleotides flanked by two primers, but with modifications pertaining to the conditions for PCR were further optimized to ensure high PCR efficiency of the library. The first round of cell-SELEX employed approximately 7 million Jurkat.E6 cells to ensure that all potential binders were retained. A total of 5 million cells were then used during the second round of selection, and the number of cells used in cell-SELEX was decreased to 2.5 million cells in subsequent rounds to increase the stringency of the selection. Enrichment at round 16 of cell-SELEX against the Jurkat.E6 cells was observed. At this point, cell-SELEX was stopped, and LIGS was introduced to a fraction of round 16 from cell-SELEX.

For the first step of LIGS, a total of $1 \times 10^5$ Jurkat.E6 cells were prewashed with wash buffer and incubated 40 minutes with 6.25 pmols of round 16 of cell-SELEX. After incubation, cells were washed twice, first with 1 mL wash buffer and then 0.5 mL wash buffer to remove unbound DNA molecules. Next, cells were reconstituted in 50 μL cell binding buffer, and 2.5 μL of anti-CD3ε HIT3 clone were added. Competitive elution of CD3ε-specific aptamers by the antibody was allowed for 40 minutes on ice. Following incubation, cells were spun down, and supernatant containing competitively eluted aptamers was collected.

Cells were analyzed after LIGS to investigate whether the addition of antibody had affected the binding of round 16 of cell-SELEX. The addition of the antibody had, indeed, replaced some aptamers from that round, as indicated by the slight decrease of fluorescence intensity. Interaction of anti-CD3ε HIT3a clone with CD3ε on Jurkat.E6 cells was also confirmed.

Figure 5:
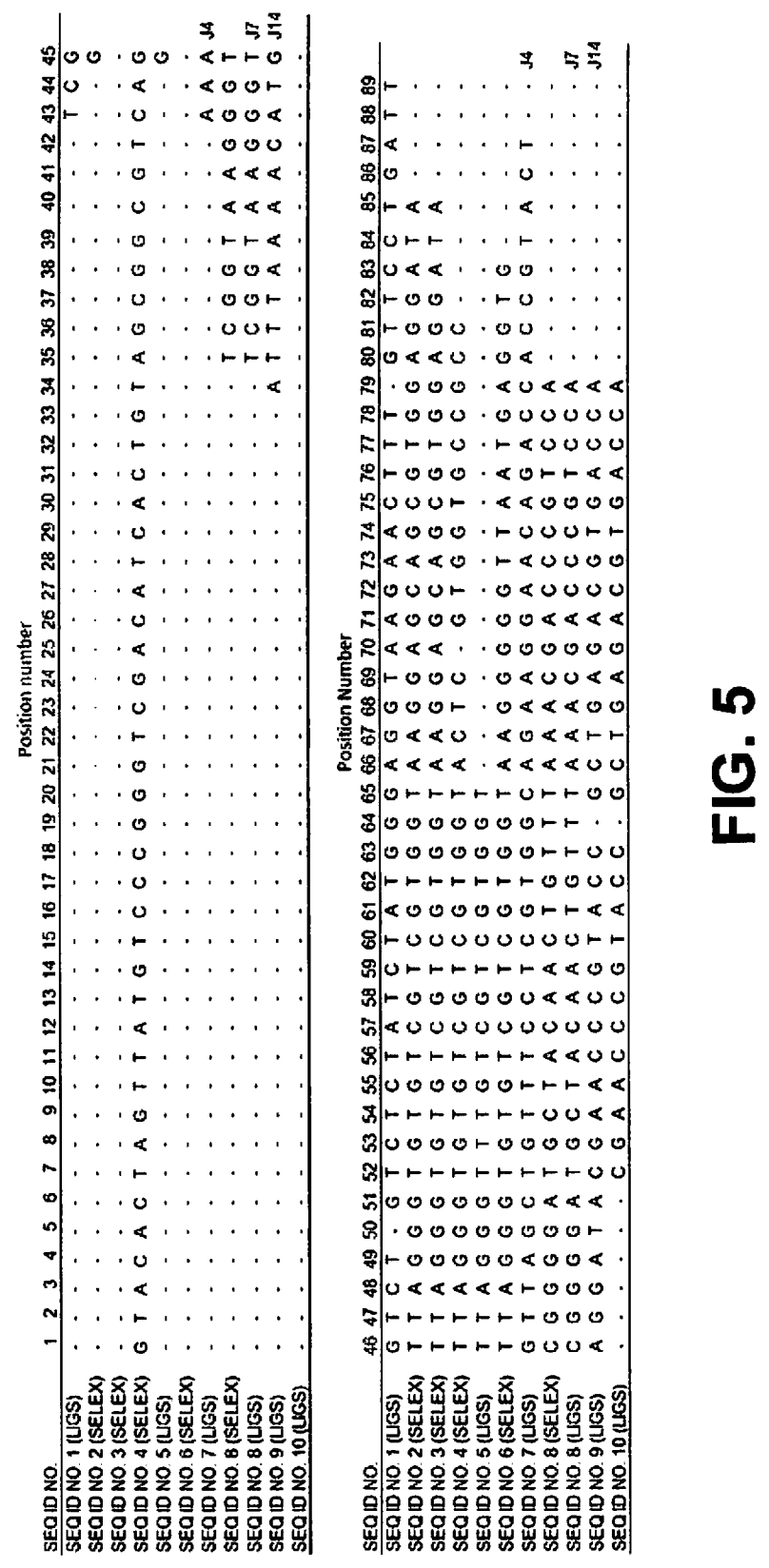

Sequence alignment strategy: The supernatant containing competitively eluted potential DNA molecules from LIGS were then PCR-amplified. To ensure that all copies of competitively eluted potential DNA aptamers were adequately amplified, a two-step PCR process was conducted. Two libraries, including (1) round 16 of cell-SELEX, which had sequences enriched towards the whole cell target, and (2) competitively eluted pool, consisting of sequences specific for CD3ε from LIGS, were cloned into bacterial vector using TOPO TA cloning and subjected to DNA sequencing. Sequences were analyzed using ClustalX.2. Analysis revealed multiple copies of the same sequences, or repeated common shared motifs interrupted by segments of DNA bases unique to each sequence. See FIG. 5. Alignment was performed on the competitively eluted sequences from LIGS and sequences from round 16 of cell-SELEX containing all sequences evolved towards Jurkat.E6 cells. Three homologous patterns were observed between the two libraries: 1) repetition of the same sequences within the pool unique to the respective libraries; 2) repetition of the same sequences in both competitively eluted library and round 16 of cell-SELEX library; and 3) repetition of sequences with common motifs in both libraries. In the case of 3), even though sequences were derived from two different pools, they shared a common motif, differing only by a few bases. Without wishing to be bound to any particular theory, it is believed that specifically enriched sequences towards the Jurkat.E6 cell line would dominate the library and that after subsequent cloning and DNA sequencing steps, these sequences would still predominate such that round 16 of cell-SELEX library would contain all sequences enriched towards Jurkat.E6 cells. Very importantly, however, the sequences obtained from LIGS would favor the selectively eluted sequences by anti-CD3 antibody binding to CD3ε antigen. Therefore, the sequences that repeatedly appeared within a family with common motifs from the two different pools were deemed more significant. Since the objective of this example aimed to select only the aptamers with most binding specificity based on LIGS, only the sequences competitively eluted by anti-CD3ε antibody sharing common motifs within the library or with round 16 of cell-SELEX library were selected for synthesis. Based on the sequence alignment, twenty seven sequences were selected for further study.

Accordingly, a total of twenty seven individual sequences were synthesized with FAM-dT at the 3'-end using standard phosphoramidite solid-state synthesis, followed by reversed phase HPLC purification. Specific binding of the sequences was tested against Jurkat.E6, using Burkitt's lymphoma cell line Ramos as the negative cell line. Burkitt's lymphoma stems from B-cell lineage, which does not express TCR-CD3 complex. A 1 µM solution of respective aptamers against $75-100 \times 10^4$ cells was incubated for 1 hour at 4° C. and subsequently washed twice with wash buffer prior to flow cytometric analysis for binding.

Interestingly, out of the twenty seven tested sequences, three sequences, J4, J7 and J14, (see FIG. 5) showed specificity against Jurkat.E6 cells, but did not bind with control Ramos cells. Twenty-four tested sequences from the competitively eluted library either bound to both Jurkat.E6 cells and Ramos cells or did not bind to either cell line. While sequences not binding to either cell line could be nonspecific sequences from the partially evolved cell-SELEX pool, the sequences binding to both cell lines might be targeting receptors common to both cell lines.

The three positive hits were further analyzed. The full-length aptamers J4, J7 and J14 showed variable binding to the Jurkat.E6 cells. During post-SELEX structure-activity relationship studies, it has been shown that truncation of full-length aptamer is desirable to optimize fold and increase affinity. Therefore, in order to maximize the most favorable fold of the aptamer, the 3' and 5' ends of J4 and J14 were systematically truncated for use in later studies. See the truncated forms of J4.1 and J14.1 in U.S. patent provisional application Ser. No. 62/320,793. All three sequences were analyzed for their binding constant against Jurkat.E6 cells. A considerably high Bmax/2 for J14.1 was observed, suggesting that J14.1 approached high specificity, but not affinity, while J4 and J7 showed comparable binding affinities to aptamers generated from cell-SELEX in other reports, suggesting that aptamers J4 and J7 approached the requirements for both affinity and specificity.

The specificity towards the antigen on CD3ε was invested by utilizing competitive binding experiments against anti-CD3ε antibody, which was used in LIGS. Anti-TCRαβ antibody was employed as a control. 50 pmols of aptamer and equal number of pmols of random sequences were incubated with 75,000 cells for 40 min at 0° C. Then, either anti-CD3ε HIT3a clone or anti-TCRαβ antibody in excess was added to allow competitive binding for an additional 40 minutes. Cells were subsequently washed and analyzed for aptamer binding using flow cytometric assay.

With reference to FIGS. 6A to 6I, flow cytometric competitive binding analysis of J4.1, J7 and J14.1 is shown without anti-CD3ε (FIGS. 6A, 6D and 6G), with anti-CD3□ (FIGS. 6B, 6E and 6H) and anti-TCRαβ antibody (FIGS. 6C, 6F and 6I) for each of J4.1, J7 and J14.1. Each FITC-labeled random control or J4.1, J7 or J14.1 (1 µM) was incubated for 40 minutes on ice with $75 \times 10^3$ Jurkat.E6 cells. Then, binding buffer or anti-CD3ε HIT3a clone or anti-TCRαβ antibody was added and incubated for an additional 40 minutes. The cells were washed with 1.5 mL of wash buffer and the binding of respective aptamer analyzed by flow cytometry. Aptamer fluorescence intensity on X-axis indicates the binding of each aptamer. Thus, increment of fluorescence intensity can be directly compared to baseline random control as an indicator of aptamer binding. Aptamer fluorescence intensity on the X-axis shifted to background when anti-CD3e HIT3a was added to all three aptamers, and binding of J7 and J14.1 was affected when anti-TCRαβ antibody was added. No difference in fluorescence intensity was observed for random control.

Three different patterns of aptamer binding in the presence of either anti-CD3ε or anti-TCRαβ antibody were observed. Aptamer J7 lost binding in the presence of both anti-CD3ε antibody and anti-TCR antibody, possibly because 1) J7 sequence might be binding to a region common to anti-TCR or anti-CD3ε or 2) structural changes were induced by one of the antibodies upon binding to the TCR-CD3 complex resulting a loss of binding of J7. In contrast, aptamer J4.1 only lost its binding when anti-CD3ε antibody was added, suggesting that aptamer J4.1 bound to an antigen unique to anti-CD3ε and that its binding to CD3ε was unaffected by anti-TCRαβ. Aptamer J14.1 showed slightly less binding when anti-CD3ε antibody was present compared to that of anti-TCR antibody. Taken together, all three aptamers showed binding affinity to Jurkat.E6 cells and in the presence of anti-CD3ε lost their binding suggesting, in turn, that these aptamers bound CD3ε or an antigen close to it. This finding proves that LIGS can be utilized to identify aptamers specific to a predetermined antigen from a multiple-domain receptor complex.

Methods for Example 1

Cell lines, Jurkat.E6 (T lymphocyte) and Ramos (Burkitt's lymphoma), were a generous gift from David Scheinberg lab and Jason Huse lab, Memorial Sloan Kettering Cancer Center. All cells were cultured in RPMI 1640 medium supplemented with 100 units/mL penicillin-streptomycin and 10% fetal bovine serum (heat-inactivated; Invitrogen). Cell lines were validated by flowcytometric assays utilizing antibodies against surface markers uniquely expressed on each cell line.

Buffer compositions: Washing buffer composed of 1×DPBS containing 4.5 g Glucose/1 L and 5 ml of 1 M MgCl$_2$/1 L. DNA Binding Buffer (DB) composed of 1×DPBS containing 4.5 g Glucose/1 L, 5 ml of 1M MgCl$_2$/1 L and 100 mg/1 L tRNA. Cell Suspension Buffer (CSB) composed of 1×DPBS containing 4.5 g Glucose/1 L, 5 ml of 1M MgCl$_2$/1 L 100 mg/1 L tRNA and 2 g/1 L BSA.

Phosphoramidites: All of the DNA reagents needed for DNA synthesis were purchased from Glen Research or ChemGenes. All the DNA oligo sequences were chemically synthesized attaching a fluorophore at the 3' end using standard solid phase phosphoramidite chemistry on an ABI394 DNA (Biolytics) synthesizer using a 0.2 µmole scale. Aptamer candidates are synthesized in house using a solid phase DNA synthesizer according to manufacturer's protocol (Applied Biosystems, Inc. Model 394). All DNA synthesis reagents were obtained from Glen Research. The completed DNA sequences were de-protected and purified using HPLC (Waters) equipped with a C-18 reversed phase column (Phenomenex). DNA concentration is determined by a UV-VIS spectrophotometer (Thermo Scientific; Evolution 300) and stored in DNA Binding Buffer (DB) at −20° C.

Cell-SELEX procedure: The PI staining of the cells and flow cytometric analysis of expression of CD3ε utilizing PE labeled anti-CD3ε antibody (BD Pharmingen mouse anti-human) along with an isotype control (mouse IgG1 Biolegend) was performed on a regular basis to maintain high quality cells expressing CD3ε prior to perform each round of SELEX.

The ss-SELEX DNA library DB buffer was heated at 95° C. for 5 minutes and snapped cooled in ice for 30 min prior to selection. Cells were prepared for SELEX experiments by washing three times with the wash buffer; subsequently, re-suspending them in 100 µL of a cell suspension buffer prior to incubation with 100 µL of a ss-DNA library for 40 minutes on ice. The first round of selection was done with $10 \times 10^6$ cells and 100 nmol of ss-DNA SELEX library.

The supernatant was collected as the unbound fraction. The cells bound to the library were washed with wash buffer (12 mL) to remove weak or nonspecifically bound DNA strands. The bound DNA library was eluted by heating at 95° C. for 10 minutes in 200 µL DNAse/RNAse free water. A two-step polymerase chain reaction (PCR) was employed for the optimization of the PCR conditions and a large scale PCR was employed to expand the evolved library as reported elsewhere. A double-stranded PCR amplified DNA-library was made single-stranded using avidin agarose beads (Pierce) and desalted using NAP-10 columns (GE). For subsequent SELEX rounds, 250 nM of the FITC-tagged ss-DNA library was used from round two to round sixteen.

Ligand-Competition: The enriched $16^{th}$ library of FITC-tagged ss-DNA cell-SELEX or control zero cycle ss-DNA library was heated at 95° C. for 5 minutes and cooled on ice for 20 minutes. $10 \times 10^5$ cells were incubated with 250 nM $16^{th}$ cell-SELEX-round ss-DNA of 25 µL for 40 minutes in ice and washed twice 1 mL and 0.5 mL wash buffer. The pre-treated Jurkat.E6 cells with the $16^{th}$ SELEX-pool were suspended in 50 µL of binding buffer and then incubated with (2.5 µL) of APC mouse anti-human CD3 antibody (BD Pharmingen; cat. no. 555342) 40 min on ice to compete and elute the potential aptamer candidates. Following incubation, the eluted $16^{th}$ fraction obtained through competition, which is in the supernatant was collected and amplified by PCR. A two-step PCR was performed. First, the whole fraction resulting from LIGS was amplified using 10-PCR cycles. The, second PCR was employed and number of cycles were optimized to obtain adequate yields necessary for the cloning step. To ensure the presence of CD3ε expressed on Jurkat.E6 cells, $10 \times 10^5$ cells were incubated in parallel with an APC mouse anti-human CD3 antibody (BD Pharmingen; cat. no. 555342) or isotype control (APC mouse IgG1-k, BioLegend; cat. no. 400121). 1 µl antibody/isotype is added per $1 \times 10^5$ cells and incubated at 4° C. for 30 min in cell suspension buffer. After incubation, all the samples washed and the sample analyzed by FACS Calibur flow cytometry (cytek) by counting 10000 events.

Two different SELEX libraries generated from (1) The DNA pool from the SELEX-$16^{th}$ round specifically enriched against Ramos cells, (2) Competitively eluted fraction of the SELEX $16^{th}$ round using ligand competition specific for antigens on the CD3ε, were cloned into bacteria using a TOPO TA cloning kit (Invitrogen) and positive colonies were subsequently sequenced by the DNA sequencing core facility at Albert Einstein College of Medicine.

Specificity assays: The bindings of the aptamer sequences were evaluated by incubating Jurkat.E6 cells or Ramos cells ($75 \times 10^3$) with a series of concentrations of FITC labeled aptamer 100 µL of binding buffer on ice for 45 minutes. The cells were then washed with 1.5 mL of wash buffer at 4° C. and reconstituted in 400 µL of wash buffer. The binding of the constructs was analyzed using flow cytometry by counting 5000 events for each concentration.

Determination of the apparent dissociation constant of aptamers: Six different working concentrations of the aptamer and control library is prepared using binding buffer, a sample set of concentrations are given; 1) 1000 nM 2) 500 nM 3) 250 nM 4) 125 nM 5) 20.8 nM 6) 3.46 nM. Cells are prepared for flow cytometry analysis by washing three times with wash buffer. $75 \times 10^3$ cells are incubated with each aptamer concentration and random library for 40 min on ice. After washing cells with 1.5 ml of wash buffer the cells are analyzed with FACS Calibur flow cytometer by counting 5000 events. FlowJo software is used to determine median fluorescence intensity for each concentration of aptamer sample and random control. Median fluorescence intensity of random control is subtracted from corresponding median fluorescence intensity of each aptamer concentration. The calculation of Bmax/2 was done using the same method as described in Sefah et al.

Competition assay with individual aptamer molecules: Fluorescently labeled 1 µM aptamer (50 µL) was incubated on ice with $75 \times 10^3$ Jurkat.E6 cells for 45 minutes. Then anti-CD3ε HIT3a clone or anti-TCRαβ was added and incubated for additional 45 minutes. At the end of incubation, cells were washed with 1.5 mL of wash buffer, and reconstituted in 300 µL of wash buffer, and binding of aptamer and antibody was analyzed on a flowcytometer.

Example 2: IgM Expressed on Burkitt's Lymphoma Cells

In this example, an antibody against IgM expressed on Burkitt's lymphoma cells (Ab) outcompeted and replaced the aptamer candidates binding to the same target of the Ab. Based on the specificity of Ab towards its target, the aptamers identified by LIGS showed specificity towards Ab's target. The selected aptamers show specificity towards Ramos cells. As expected, identified specific aptamers for mIgM, competes with the cognate Ab binding to its target.

The conventional cell-SELEX method was first employed against Ramos cells that naturally express high-levels of the desired antigen (mIgM). Cell-SELEX was continued until a partial enrichment of the evolved SELEX library against the target cells was observed. Next, the partially enriched library was divided into fractions. The first fraction was PCR-amplified, cloned and sequenced. These sequences are specific towards target cells. An excess of Ab was introduced on the second fraction, which was pre-incubated with Ramos cells subsequently washed to remove non-binding sequences, to selectively outcompete and elute potential aptamers that bind to the cognate antigen less strongly when the anti-IgM Ab is present. The sequences outcompeted by Ab were PCR-amplified, cloned, sequenced. Finally, sequences obtained from DNA sequencing of two fractions of SELEX pool were aligned using the ClustalX.2 program and based on set criteria, specific aptamer candidates against mIgM in target cells were screened and identified.

Cell-SELEX was carried out without incorporating a negative selection on the assumption that potential aptamer candidates could be partially enriched towards the desired antigen, i.e., mIgM, applying an antibody against the aptamer would elute these sequences, despite the existence of unrelated off-target sequences in the partially-evolved pool. The expression of mIgM on Ramos cell lines was evaluated utilizing anti-IgM antibody. Ten million cells and a high concentration of initial DNA library were employed during the first round of selection to increase the probability of capturing potential "binders". A partial enrichment of the evolved pool was detected starting at round 13 of cell-SELEX pool, compared to the unselected pool. The remaining round 13 was used in LIGS. To elute mIgM-specific sequences, an excess amount of Ab (1 µg) was introduced to compete with the aptamer from fraction of round 13 of cell-SELEX pool pre-incubated with Ramos cells followed by a wash to remove non-binding DNA molecules. The supernatant containing sequences out-competed by Ab were then collected.

To confirm that the Ab had indeed interacted with mIgM, and to investigate Ab's effect on aptamer pool 13 fraction-2 binding to Ramos cells, cells after Ab competition were analyzed by flow cytometry. The binding of the anti-IgM Ab to its antigen on Ramos cells replaces the binding of some aptamer sequences enriched in the evolved pool. This observation suggests that at least a few sequences enriched in the round 13 fraction-2 are eluted by anti-mIgM Ab. Based on the PCR of eluted pool at this step, it was observed that a low number of sequences were eluted during this step, mainly because: 1) the DNA pool was only partially evolved, with a low number of aptamer copies, 2) a low number of cells was employed in the LIGS, 3) Ab competition, which is designed to selectively elute specific sequences, only generates a low number of specific sequences for one target antigen.

Figure 7:
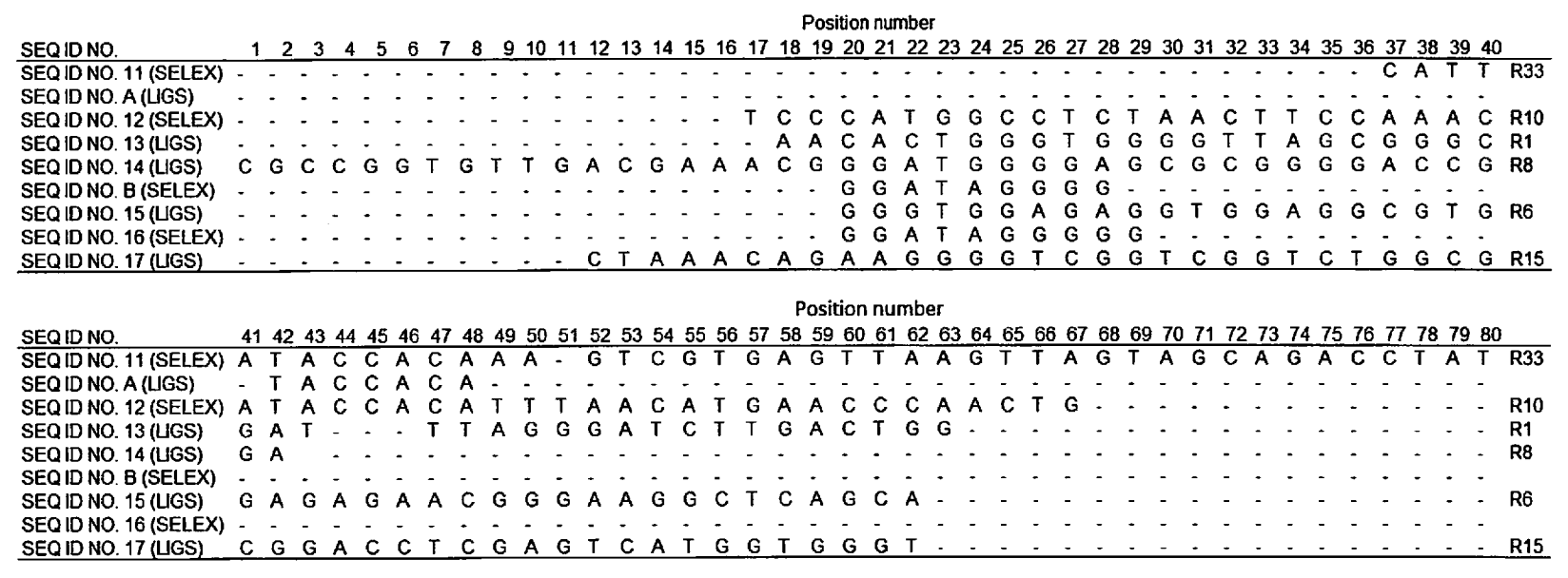

Since the SELEX pool is partially enriched, multiple fractions of round 13 of cell-SELEX pool were cloned, sequenced and competitively eluted fraction of round 13 of cell-SELEX pool. About 500 sequences were obtained from all fractions, which could be categorized into families based on their sequence homology. Without wishing to be bound to any particular theory, it was believed that enriched sequences towards the cell line (Ramos) predominate in the library and have a higher probability in "surviving" the pool. Therefore, the sequences resulting from sequencing of round 13 of cell-SELEX pool would contain all of the sequences that were enriched towards Ramos cells. On the other hand, the sequences obtained from LIGS would favor the set of sequences selectively eluted by the ligand. Analysis of the sequences obtained from sequencing of competitively eluted pool or the cell-SELEX round 13 pool showed two types of sequences: First, sequences share motifs common to sequences in round 13 of cell-SELEX pool and competitively eluted pool; Second, sequences repeated within the competitively eluted library. Both types of sequences that repeatedly appeared within a family with common motifs from both pools or within the competitively eluted pool were selected for further study. For example, as shown in FIG. 7, sequence R10 only appeared on cell-SELEX round 13, however, a shorter version of a common motif was identified to appear in competitively eluted pool. Also, R6, R8 and R1 share a common GGG motif, differing only in few bases within the motif (FIG. 7). The same sequence was observed repeated within the competitively eluted library, and within the main cell-SELEX round 13 pool. Since the scope of this example is to identify sequences specific towards mIgM, even though sequences repeated within the main library might be potential aptamer candidates, the sequences that do not show any common motifs with competitively eluted sequences were not investigated. Based on these criteria thirty three different sequences were synthesized and tested either from competitively eluted library or from the main SELEX-library of round 13. Out of thirty three sequences twenty seven sequences are from competitively eluted library and six sequences share the same motif of that of competitively eluted library but from cell-SELEX round 13 main pool.

Since the LIGS is predominantly aimed at increasing specificity, individual chemically synthesized sequences based on set criteria of sequence selection, were first tested for specificity. Target Ramos cells were used which expresses high levels of mIgM and non-target Jurkat.E6 cells. Since Jurkat.E6 cells are human T-cell leukemia mainly designed to investigate T-cell receptor complex, by definition these cells do not express mIgM, thus, Jurkat.E6 cells are comparable to a cell line that do not express the antigen validates its use as a non-specific cell line. All specificity assays were done using FITC-labeled aptamers, and a randomized DNA sequence used as a control. Interestingly, three types of binding patterns were observed within tested 33 sequences: 1. Sequences do not bind to either Ramos cells or Jurkat.E6 cells, which might be non-specific amplicons in the library, 2. Sequences bind to both Ramos and Jurkat.E6 cells, these sequences might be binding to commonly present Fcγ receptors present in both types cells eluted by the Ab competition, 3. Sequences bind to only Ramos cells but not to Jurkat.E6 cells, which might be specific sequences towards Ramos cells. This suggests that pool resulted from competitive elution does not necessarily contain only specific sequences, and screening of individual aptamer candidates for specificity is desired to identify antigen-specific aptamer candidates. Out of the tested thirty-three sequences three unique sequences (R1, R10 and R15) were identified that show specificity towards Ramos cells.

The sequences that showed specificity towards mIgM-positive Ramos cells were further investigated for binding affinity. Bmax/2 was evaluated for the sequences that showed specific binding. The calculated Bmax/2 for R1, R10 and R15 are in the sub-micro molar range against Ramos cells, suggesting that sequences generated using LIGS show lower affinities. The issue of lower affinities of the identified aptamers could be predominantly because LIGS was applied to a partially evolved SELEX pool, and evolution of sequences was interrupted. Therefore, a partially evolved SELEX pool might contain sequences with lower to moderate affinities. However, the affinity of these aptamers could be further enhanced given their high specificity by post-SELEX modification followed by linear multimerization approaches as described before.

The identified specific aptamer candidates were investigated to determine if each competes with an anti-IgM Ab for the binding site. The validation of the target using competition against the corresponding antibody has been used before. A competition was performed by first pre-incubating Ramos cells with anti-IgM Ab or anti-CD20 Ab for 30 min and subsequent wash. CD20 is uniquely expressed in mature normal B cells, on early developmental stages. CD20 positive B cells are the source of a variety of B-cell neoplasms, including Ramos cells, which is a B-cell Non Hodgkin's Lymphoma. Therefore, anti-CD20 antibody was used as a control to investigate the antigen specificity to further confirm the specificity of the aptamers towards mIgM. Ramos cells pretreated with Ab were then incubated with individual aptamer sequences. Following wash, binding of each aptamer was analyzed using flow cytometry.

FIGS. 8A to 8C depict the results of flowcytometric competitive binding analysis of R1, R10 and R15 in the presence of IgM. Each FITC labeled library (0.4 µM for R1 (FIG. 8A), 0.5 µM for R10 (FIG. 8B) and R15 (FIG. 8C))

was incubated for 60 min on ice with $1\times10^5$ Ramos cells pre-incubated with either anti-IgM (line 812 FIGS. 8D-F)) or anti-CD20 (line 810 FIGS. 8D-F) followed by washing with 3 mL of wash buffer, and subsequently analyzed by flowcytometry. Area 800 illustrates data points for random plus anti-IGHM while line 802 illustrates data points for random plus anti-CD20. Aptamer fluorescence intensity on x-axis is indicative of binding of each aptamer. Thus, increment of fluorescence intensity directly translates into aptamer binding to pre-treated Ramos cells. When the cells are pre-incubated with anti-CD20 (line 806) all three-aptamer show, an increase in fluorescence intensity. However, when the anti-IgM was introduced aptamer binding is diminished (line 804).

As shown in FIG. 8A to 8C, the introduction of anti-IgM Ab diminished the binding of the aptamer for R1 (FIG. 8A), R10 (FIG. 8B) and R15 (FIG. 8C) showed a slight decrease indicated by diminished binding of each aptamer in the presence of anti-IgM but not when anti-CD20 is present in the corresponding histograms. When the cells are pre-incubated with anti-CD20 all three-aptamers show, an increase in fluorescence intensity (line 810) indicating antibody is binding to the cells. Also when anti-IgM antibody binds to cells indicated by increase in fluorescence intensity (line 812)

R1 and R10 showed a substantial competition with anti-IgM based on the diminished aptamer fluorescence intensity compared (FIGS. 8A-C, line 804) Ramos cells pre-incubated with anti-CD20 antibody (FIGS. 8A-C line 806), R15 does not show substantial competition suggesting that binding of R15 might be stabilized by a secondary antigen specific for Ramos cells. The competition with only anti-IgM not with anti-CD20 is a clear indication that R10 and R1 are specific for mIgM.

Each aptamer was also investigated for its ability to block the binding of the anti-IgM. Post-SELEX modification of aptamers is desirable to increase the homogenous fold and to obtain better yields in chemical synthesis. Therefore, in order to further optimize the structure R1 and R 10 were systematically truncated. A truncated version of R1.1 and R10.T1 were used for blocking experiments. Interestingly R1.1 blocked at lower concentrations of anti-IgM, but no significant blockage of the binding of the anti-IgM to Ramos cells was observed at higher concentration of anti-IgM. Also, no significant difference in the binding of anti-IgM was observed when R10.T1 present compared to randomized control. This could be because R10.T1 unable to block the antibody due to its high off rates resulting from lower affinity. Antibodies are bivalent in nature, therefore, the "on" rate of an antibody binding to its antigen is higher and the "off" rate is lower compared to monovalent aptamers. While these kinetic parameters are key factors, the further evaluation of binding kinetics of Ab and its effect on either aptamer displacement or binding to its antigen in biochemical understanding of LIGS.

Similar patterns of molecular recognition of R10 and R1 were observed. These two aptamers investigated to determine if they compete to bind to the same antigen. Unlabeled R1.1 was incubated with excess to fluorescently labeled R10 with Ramos cells. Washing of unbound aptamer followed by flowcytometric analysis revealed that both R1.1 replaces R10 suggesting that both aptamers binding to the same antigen. This evidence further confirms that the aptamers identified utilizing antigen LIGS binding to the same antigen on Ramos cells.

Theoretically, aptamer interactions are specific towards one target; therefore, the set of aptamers generated in the end of the cell-based selection are expected to correlate to the altered levels of molecules in the positive cell line. Using this approach, a number of aptamers had been selected. Aptamers selected using cell-SELEX compete with the cognate antibody for binding to its target antigen. For example, the aptamer TD05, selected using the cell-SELEX method targeting Burkitt's lymphoma, binds to the heavy chain of membrane bound IgM (mIgM) and competes with the anti-IgM antibody, permitting the bound aptamer from the target to be eluted into the solution. Similarly, an RNA aptamer selected against CD71 expressing cells using the hybrid-SELEX method, competes with anti-transferrin antibody. A cell-SELEX selected aptamer against myeloid leukemia, binds to the sialic acid-binding Ig-like lectin protein and competes with its respective antibody. These reported observations suggest that the aptamers can bind to a region of the receptor close to an Ab binding-site. The decrease in aptamer binding when the respective cognate ligand is present can be due to steric hindrance resulting from the large size or high affinity of the ligand, eluting the aptamer; or the structural changes in the receptor protein induced by ligand (Ab) binding. Also, an antibody is bivalent so the affinity is higher than the monovalent aptamers. High affinity of an antibody leads to lower $K_{off}$ and high $K_{on}$ and kinetically favors the competition by the antibody. It has been already shown that aptamers usually bind to ligand binding sites on receptors or active sites of proteins. Therefore, a partially evolved cell-SELEX aptamer library can also be utilized to identify antigen specific aptamers, by simply using a ligand against the desired target to elute the respective aptamer sequences.

In this example aptamers against mIgM were selected. The mIgM molecule is considered as the hallmark of B-cells, plays a major role in B-cell development and is a major player in transformation of B-cell into malignant B-cells. Also, mIgM pays a major role in autoimmune disorders and 95% of human lymphomas originate from B-cells. There is evidence of activated protein kinase stimulated downstream of BCR demonstrating the significance of developing therapeutics against BCR. Currently, there are no successful targeting agents available against mIgM. Three different aptamer candidates with specificity towards mIgM were identified.

Methods of Example 2

Cell culture: All cells were cultured in RPMI 1640 medium supplemented with 100 units/mL penicillin-streptomycin and 10% fetal bovine serum (heat-inactivated; Invitrogen).

Phosphoramidites: All of the DNA reagents needed for DNA synthesis were purchased from Glen Research or ChemGenes. All the DNA oligo sequences were chemically synthesized attaching a fluorophore at the 3' end using standard solid phase phosphoramidite chemistry on an ABI394 DNA (Biolytics) synthesizer using a 0.2 µmole scale. The completed DNA sequences were de-protected and purified using HPLC (Waters) equipped with a C-18 reversed phase column (Phenomenex). All in vitro experiments were performed using a binding buffer composed of DPBS and 4.5 g/L glucose (Sigma-Aldrich) and 5 mM $MgCl_2$, 100 mg/L, tRNA (Sigma-Aldrich), 1 g/L BSA (Sigma-Aldrich). The wash buffer was composed of DPBS with 5 mM $MgCl_2$ and 4.5 g/L glucose (Sigma-Aldrich).

SELEX Primers and Library: Primers and SELEX library was obtained from Sefah K, D Shangguan, X Xiong, M B O'Donoghue and W Tan. (2010). Development of DNA aptamers using Cell-SELEX. Nat Protoc 5:1169-1185. The SELEX library consisting of primers flanked by a 45 nucleotide-randomized region was purchased from IDT DNA Technologies.

Cell-SELEX procedure: The PI staining of the cells and flow cytometric analysis of expression of mIgM utilizing FITC labeled anti-IgM antibody (1 µg, Goat anti human, life technologies) along with an isotype control (1 µg, Goat anti mouse IgG2a, Biolegend) was performed on a regular basis to maintain high quality cells expressing mIgM prior to perform each round of SELEX.

The ss-SELEX DNA library binding buffer was heated at 95° C. for 5 minutes and snapped cooled in ice for 30 min prior to selection. Cells were prepared for SELEX experiments by washing three times with the wash buffer; subsequently, re-suspending them in 100 µL of a cell suspension buffer (cell binding buffer with 2 g/L BSA) prior to incubation with 100 µL of a ss-DNA library for 40 minutes on ice. The first round of selection was done with $10 \times 10^6$ cells and 100 nmol of ss-DNA SELEX library.

The supernatant was collected as the unbound fraction. The cells bound to the library were washed with wash buffer (10 mL) to remove weak or nonspecifically bound DNA strands. The bound DNA library was eluted by heating at 95° C. for 10 minutes in 200 µL DNAse/RNAse free water. A two-step polymerase chain reaction (PCR) was employed for the optimization of the PCR conditions and a large scale PCR was employed to expand the evolved library. A double-stranded PCR amplified DNA-library was made single-stranded using avidin agarose beads (Pierce) and desalted using NAP-10 columns (GE) as described by Sefah K, D Shangguan, X Xiong, M B O'Donoghue and W Tan. (2010). Development of DNA aptamers using Cell-SELEX. Nat Protoc 5:1169-1185. For subsequent SELEX rounds, 250 nM of the FITC-tagged ss-DNA library was used from round two to round thirteen.

Flow cytometric Analysis: The progress of the selection was evaluated utilizing flow cytometric analysis. The PCR amplified DNA library is labeled with fluorescence tag FITC at the 5' end, analyzed by a flow cytometric assay. A 250 nM FITC-tagged ss-DNA library (25 µL) was incubated with $2.5 \times 10^5$ Ramos cells in binding buffer for 40 minutes on ice. After washing twice with wash buffer (3 mL), cells were suspended in 500 µL wash buffer and was analyzed by a FACS Calibur flow cytometer (Cytek) by counting 10000 events.

Cell binding assays: The affinities of the aptamer sequences were evaluated by incubating Ramos cells ($2.0 \times 10^5$) with a series of concentrations of FITC labeled aptamer 200 µL of binding buffer on ice for 60 minutes. The cells were then washed twice with 1 mL of wash buffer at 4° C. and reconstituted in 400 µL of wash buffer. The binding of the constructs was analyzed using flow cytometry by counting 5000 events for each concentration. The calculation of Bmax/2 was done using the same method as described in Sefah K, D Shangguan, X Xiong, M B O'Donoghue and W Tan. (2010). Development of DNA aptamers using Cell-SELEX. Nat Protoc 5:1169-1185.

The specific binding of each aptamer was evaluated by incubating Ramos cells (0.5 or $1.0 \times 10^5$) and Jurkat.E6 cells (0.5 or $1.0 \times 10^5$) with FITC labeled aptamers of concentrations of 0.5 or 1 µM in a 100 µL of cell suspension buffer on ice for 60 minutes. The cells were then washed twice with 1 mL of wash buffer at 4° C. and reconstituted in 250 µL of wash buffer. Aptamer binding was analyzed using flow cytometry by counting 5000 events for each concentration. As a positive control, a similar assay was performed using an ALEXA FLUOR 647 labeled anti-IgM antibody (1 µg, Goat anti human µ-chain, Life Technologies) along with an isotype control (1 µs, Goat anti human, Biolegend).

Ligand-guided cell-Selection Protocol: Ligand-Competition: The enriched $13^{th}$ pool FITC-tagged ss-DNA pool or control zero cycle ss-DNA pool was heated at 95° C. for 5 minutes and cooled on ice for 20 minutes. $2.5 \times 10^5$ cells were incubated with 250 nM $13^{th}$ SELEX-pool ss-DNA pool of 25 µL for 40 minutes in ice and washed once with 3 mL wash buffer. The pre-treated Ramos cells with the $13^{th}$ SELEX-pool were suspended in 504 of binding buffer and then incubated with an ALEXA FLUOR 647 goat anti-human IgM antibody (1 µg) 30 min on ice to compete and elute the potential aptamer candidates. Following incubation, the eluted $13^{th}$ pool obtained through competition, which in the supernatant was collected and amplified by PCR. To ensure the presence of mIgM expressed on Ramos cells, $2.5 \times 10^5$ cells were incubated in parallel with an ALEXA FLUOR® 647 goat anti-human IgM or ALEXA FLUOR® 647 goat IgG Isotype antibody for 30 minutes. After incubation, all the samples were washed and the sample analyzed by FACS Calibur flow cytometry (cytek) by counting 10000 events.

Two different SELEX libraries generated from (1) The DNA pool from the SELEX-$13^{th}$ round specifically enriched against Ramos cells, (2) Competitively eluted fraction of the SELEX $13^{th}$ round using antibody competition specific for antigens on the mIgM, were cloned into bacteria using a TOPO TA cloning kit (Invitrogen) and positive colonies were subsequently sequenced by the DNA sequencing core facility at Albert Einstein College of Medicine.

Antigen specificity: Antigen specificity is determined by competition of anti-IgM antibody with aptamers. In order to investigate the competition between anti-IgM (mu) antibody and aptamer, first 0.5 µg/mL of APC anti-human CD20 antibody and 0.25 µg/mL of ALEXA FLUOR® 647 goat anti-human IgM antibody were incubated with $4 \times 10^5$ Ramos cells on ice for 30 min. Then the free antibody was washed with 3 mL of wash buffer, and cells were reconstituted with 400 µl of cell suspension buffer. A final concentration of 0.4-0.5 µM of FITC labeled aptamer or corresponding random control are incubated 125 µL of cell suspension buffer for another 60 min on ice. Then the cells were washed with 1 mL wash buffer and binding events were monitored in FL1 for the aptamer and FL4 for the antibody counting 5000 events using flowcytometry.

Blocking experiments were also conducted with aptamers pre-incubated with antibody. A $10 \times 10^3$ of Ramos cells first incubated with 1 µM of corresponding aptamer or random control on ice for 45 min. Then the pre-incubated cells with the aptamer or random were added to serially diluted concentrations from 20 ng/µL to 0.2 ng/µL of anti-IgM solution and allowed free competition for additional 35 min on ice. Then the cells were washed twice with 1 mL and 0.5 mL wash buffer and re-suspended in 300 µL wash buffer and analyzed the antibody binding with flow cytometry.

To provide proof of principle a method was designed that targeted two receptor proteins. B-cell receptor (BCR) and a T-cell receptor (TCR). To prove the concept a cell line was identified that naturally expresses the membrane receptor of interest as the target cells.

LIGS exploits the inherent evolutionary step of competition between weak and strong binders in a combinatorial library and can be used to evolve functional nucleic acid (NA) ligands against the multi-component cell-surface receptor T-cell receptor (TCR)-CD3 complex expressed in cultured and primary cells. Using two monoclonal antibodies (mAbs), OKT3 and UCHT1, as competing ligands, a total of five aptamer candidates were identified. All five aptamers and mAbs compete for the same binding site in TCR-CD3 complex. Two of the aptamers show specific recognition of isolated primary T-cells from healthy donors. LIGS shows that, by exploiting the selection step in a combinatorial library and known ligand-receptor interactions, multiple ligands against a multi-component receptor protein in its native state can be identified.

Empirical evidence generated over five decades demonstrates that cells undergo structural changes at the molecular level in response to environmental cues that change the cell-surface landscape and cell-receptor interactions with their ligands, leading to a modified cell state. Thus, in response to environmental cues, the expression levels of cell-surface protein receptors change, in turn affecting the behavior of signaling pathways. For this reason, membrane proteins remain most attractive targets in developing molecular tools. Indeed, researchers and clinicians have studied patterns of protein receptor overexpression to better understand the onset and progression of disease, as well as to identify therapeutic targets. However, when cell membrane proteins are purified, their resultant conformation can be very different from that in their native state, thus making cell surface proteins challenging as targets for the development of artificial ligands, drugs or diagnostics. One third of the human genome encodes membrane receptors compared to soluble proteins. Yet, the atomic structures of membrane proteins are limited, and the paucity of structural data, in turn, hinders the rational design of small-molecule drugs using computational modeling. It is difficult to establish experimental conditions that preserve the native conformation of a protein in isolation. Moreover, membrane proteins are known to act together, forming transient systems across the entire cell membrane surface in response ligand binding. Such complexes are difficult, or even impossible to purify and identify while maintaining their native functional state. Essentially, this means that the identification of functional ligands against membrane proteins in purified state may not lead to molecules that can recognize the same protein, whether single receptor or multi-component receptor, by its native expression levels on the cell membrane. One way to address these challenges is to use cells as the whole target in high-throughput screening technologies, such as phage-display or SELEX (Systematic Evolution of Ligands by Exponential Enrichment), to discover functional ligands based on peptide or nucleic acid aptamers. Cell-based SELEX, for example, is designed to evolve and enrich a library of DNA aptamers against a whole cell without modifying the biological state of the cell. After successive selection iteration in cell-SELEX, nucleic acid (NA) ligands are enriched against multiple receptor proteins expressed in their native state. The in vitro use of combinatorial libraries of NA ligands in the laboratory to discover nucleic acid ligands against proteins was introduced in the 1990s. Generally, SELEX technology subjects a combinatorial library of NA ligands to iterative cycles of molecular evolution to identify functional NA ligands, also known as aptamers. In vitro selection of Nucleic Acid Aptamers (NAAs) is experiencing a renaissance by expanding the repertoire of nucleic acids and by integrating NGS during the SELEX process. LIGS exploits the inherent evolutionary step of competition between weak and strong binders in a SELEX library to discover specific DNA ligands. This method allows the identification of highly specific DNA ligands against precise sites of cell surface receptors in their native state guided by an external competitor, such as a monoclonal antibody (mAb). LIGS is a particularly attractive technology in identifying functional ligands against multi-component membrane receptors. One such complex protein is TCR-CD3 expressed on T-cells. This is a multi-domain transmembrane protein, consisting of a heterodimer, $\alpha\beta$, and two ectodomains, CD3$\epsilon\gamma$ and CD3$\epsilon\delta$. The main $\alpha\beta$ heterodimer consists of a variable and a constant domain, while the CD3$\epsilon$ domain is conserved and non-glycosylated, making CD3$\epsilon$ a suitable target for ligand development. The TCR-CD3 complex regulates cellular interactions of the immune system, also making it an attractive target for the development of synthetic immunomodulators. The structure of this complex and its interaction with its two antibodies, OKT3 and UCHT1, has been well documented. Two mAbs, OKT3 and UCHT1, were utilized to discover functional DNA ligands against TCR-CD3 complex in its native state expressed in cultured T-cell leukemia (Jurkat.E6) cells and primary human T-cells using LIGS. The unique ability of LIGS to select aptamers towards well-known protein receptor targets in their native conformation using pre-existing ligand-receptor interactions allows the streamlining of the SELEX process toward the identification of multiple aptamers against a cell-surface receptor. Combining this with the use of the FASTAptamer, a toolkit designed to address the primary sequence analysis requirements from high-throughput sequencing of combinatorial selection populations, and the GALAXY platform, a web-based platform for accessible, reproducible, and transparent computational biomedical research, a total of five aptamer candidates, varying in affinity from 3.06±0.485 nM to 325±62.7 nM towards TCR-CD3$\epsilon$ were identified. The aptamer family was validated utilizing multiple strategies, including competitive binding analysis with respective antibodies used in LIGS, as well as a double-knockout Jurkat cell line generated by CRISPR targeting of the TRAC gene that encodes the T-cell receptor alpha constant chain and CD3$\epsilon$ gene that encodes CD3-epsilon polypeptide knockout cells. Additional cross-competition experiments using labeled and unlabeled aptamers reveal that all five aptamers compete for the same binding site. The highest-affinity aptamer and the aptamer identified using LIGS against primary T-cells show specific recognition of isolated primary T-cells. Exploiting the inherent competition between weak and strong binders in a combinatorial library and existing ligand-receptor interactions, combined with bioinformatics, leads to identification of multiple high affinity DNA ligands against a multi-component receptor protein in its native state without manipulating the cell-surface landscape.

Methods and Materials

Cell lines: Jurkat (Clone E6, acute T-cell leukemia) and BJAB (Human Burkitt's lymphoma B-cell line) were a generous gift from the Huse Lab and David Scheinberg Lab at Memorial Sloan Kettering Cancer Center, New York, N.Y. MOLT-3 (acute lymphoblastic leukemia) and Toledo (non-Hodgkin's B-cell lymphoma) were purchased from American Type Culture Collection (ATCC) Manassas, Va. Double knockout (CRISPR-Cas9 targeting CD3$\epsilon$ and TRAC genes) Jurkat cells were purchased from Synthego Corp, Redwood City, Calif. All cell cultures were maintained in RPMI 1640 medium (25 mM HEPES, L-Glutamine, HyClone) supplemented with either 10% or 20% fetal bovine serum (FBS), 100 Units/mL penicillin-streptomycin and 1% non-essential amino acids.

Preparation of primary T-cells: All experiments using primary cells were conducted at Memorial Sloan Kettering Cancer Center using IRB-approved protocols. Peripheral blood mononuclear cells (PBMCs) were isolated from whole blood of two different healthy donors using Ficoll-Paque PLUS (GE Healthcare, Chicago, Ill.). B-cells were separated from PBMCs by using human CD19 microbeads, according to the manufacturer's manual (Miltenyi Biotec, Bergisch Gladbach, Germany). The B-cell-depleted PBMCs were then subjected to FACS sorting using a FACSAria (BD Biosciences, San Jose, Calif.) high-speed cell sorter to obtain CD5+ cells. These cells were then sorted to collect CD4+ and CD8+ T-cell populations that were subsequently pooled together to be used in experiments.

SELEX library and primers: SELEX library and primers consisted of 37 nucleotide (nt) long sequences ($N_{37}$) in the randomized region flanked by two constant primer annealing regions at each end: (5'-ATC GTC TGC TCC GTC CAA TA-$N_{37}$-TTT GGT GTG AGG TCG TGC-3', SEQ ID NO: 18). A FITC-labeled forward primer (5'-FITC-ATC GTC TGC TCC GTC CAA TA-3', SEQ ID NO: 19) and a biotinylated reverse primer (5'-biotin-GCACGACCT-CACACCAAA-3', SEQ ID NO: 20) were used. SELEX library and primers were purchased from Integrated DNA Technologies Inc. (IDT), Coralville, Iowa.

Buffer formulations: The selection was performed using cell suspension buffer (CSB) consisting of RPMI-1640 medium containing 200 mg/L tRNA and 2 g/L BSA. tRNA and BSA were added to block nonspecific binding sites on the cell surface. For the selection containing primary T-cells, the wash buffer was formulated by adding 200 mg/L salmon sperm DNA to the RPMI-1640 medium.

Antibodies" In vivo anti-CD3 monoclonal antibodies UCHT1 (mouse anti-human, isotype IgG1, Catalog#: BE0231), OKT3 (mouse anti-human, isotype IgG2a, Catalog#: BE0001-2), anti-CD28 monoclonal antibody (mouse anti-human, isotype IgG2a, Clone 9.3, Catalog#: BE0248) and In vivo mouse IgG1 isotype control, (Clone MOPC-21 Catalog#: BE0083) were obtained from BioXCell, West Lebanon, N.H. and used for LIGS experiments. ALEXA FLUOR® 647-conjugated Goat anti-Mouse IgG (Catalog#: 115-605-062) was obtained from Jackson ImmunoResearch Laboratories, Inc. West Grove, Pa. APC-conjugated monoclonal antibodies, Mouse anti-Human TCRαβ (BD PHARMINGEN®, 563826), Mouse anti-Human CD3 (clone UCHT1, BD PHARMINGEN®, 555335), Mouse anti-Human CD3 (clone OKT3, EBIOSCIENCE®, 17-0037-41), and Mouse anti-Human CD28 (EBIOSCIENCE®, 17-0289-41) were used for routine flow cytometry analysis.

Cell-SELEX: Target Jurkat.E6 cells were analyzed for the expression of TCR-CD3ε by utilizing respective antibodies via flow cytometry. Each round of SELEX was performed using cells at log-phase growth ($6.0 \times 10^5$ to $8.0 \times 10^5$ cells/mL), and flow cytometric analysis was performed to confirm the presence of a single homogeneous cell population. First round of SELEX was performed by incubating 10.8 nmoles of denatured HPLC-purified single-stranded DNA (ssDNA) library with $1.0 \times 10^7$ cells in a final volume of 500 μL. The DNA library suspended in 250 μL of RPMI was denatured by heating at 95° C. for 5 min, followed by folding for 45 min at 25° C. in order to allow formation of proper secondary structures. Cells were washed three times with wash buffer and resuspended in CSB to obtain $1.0 \times 10^7$ cells in 250 μL of CSB. The incubation was performed at 25° C. for 1 hr by gently shaking at 450 rpm. After 1 hr, cells were washed with 9 mL of RPMI to remove unbound sequences. The cells were reconstituted in 300 μL of DNAse-free water, and the bound sequences were eluted by heating at 95° C. for 10 min, followed by centrifugation for 10 min at 14,800 rpm. Collected supernatant was amplified with 5 PCR cycles, and the resulting library was converted to ssDNA to obtain FITC-labeled sense strand. Starting from second round of SELEX, the number of PCR cycles were optimized for each round and scaled-up accordingly. When necessary, a two-step PCR was utilized in which product of the first PCR was used as a template for the second PCR for the optimization of number of cycles. The process was repeated until the SELEX library was enriched with survivors. In order to increase the stringency of the selection, the total number of cells was gradually decreased to $5.0 \times 10^6$ for round 2 and to $2.5 \times 10^6$ for subsequent rounds of SELEX. 250 nM of final library were used, starting at round 2 onwards. The washes were increased to 2×3 mL washes at round 2 and then 3×3 mL washes for the subsequent rounds. UV-VIS spectroscopy was used to determine final yield of the amplified library after conversion to ssDNA, starting at round 2. One round of negative selection was employed against BJAB cells for which the ssDNA library eluted from Jurkat.E6 cells was divided into two equal fractions and incubated with $1.0 \times 10^6$ BJAB cells separately. The selection was concluded after 16 rounds of cell-SELEX.

Monitoring selection progress: Progress of the selection was monitored at three-round intervals, starting from round 7, by incubating $2.0 \times 10^5$ Jurkat.E6 cells with FITC-labeled ssDNA of unselected control library, and the pools after rounds 7, 10, 13 and 16 at a final concentration of 250 nM in 50 μL total volume. After one hour of incubation at 25° C., cells were washed twice using 1 mL RPMI and reconstituted in 250 μL RPMI. Binding events were analyzed using flow cytometry (BD FACScan).

Cell-SELEX against primary T-cells: One round of selection was performed against isolated primary T-cells by incubating $5.0 \times 10^5$ cells with 27.25 pmoles of the library after 14 rounds of enrichment against Jurkat.E6 cells at a final library concentration of 250 nM. Prior to incubation, the cells were prepared by washing twice with RPMI containing 200 mg/L salmon sperm DNA. The library was prepared using the same protocol as that for initial rounds, and the incubation was performed at 25° C. for 1 hr of shaking at 300 rpm. The cells were washed twice with 2 mL of RPMI, and bound sequences were recovered by using 250 μL of DNAse-free water. A two-step PCR procedure was employed for amplification of the eluted sequences. PCR cycle optimization was carried out to determine an optimum number of cycles for the second PCR, and optimized conditions were used in preparative PCR.

Ligand-Guided Selection

LIGS against primary T-cells: The enriched, FITC-labeled ssDNA library after 1 round of selection against primary T-cells (R15T) and unselected control ssDNA library was heated at 95° C. for 5 min and equilibrated at 25° C. for 45 min. 60 μL of ssDNA were incubated with an equal volume of $5.0 \times 10^4$ primary T cells at a final library concentration of 250 nM for 50 min at 25° C., and this step was performed in four individual tubes. After incubation, the cells were washed twice with 2 mL of RPMI, and cells were resuspended in 100 μL of CSB containing one of the following: CSB only, CSB supplemented with OKT3 antibody, CSB supplemented with UCHT1 antibody, or CSB supplemented with anti-CD28 antibody. Each mAb was used at a final concentration of 15 nM. All four samples were incubated for an additional 40 min at 25° C. to promote competitive elution of target-specific aptamer candidates. After incubation, the supernatant containing competitively eluted sequences was collected, and the eluted sequences were preserved for PCR amplification, followed by NGS library preparation. The cells were then incubated with ALEXA FLUOR® 647-conjugated goat anti-mouse IgG at 5 μg/mL final concentration and analyzed by flow cytometry to evaluate the binding of mAbs.

LIGS against Jurkat.E6 cells: Before performing LIGS against Jurkat.E6 cells, the dissociation constant ($K_d$) of the library was determined, utilizing the evolved $16^{th}$ round of cell-SELEX library against target cells with and without washing free ligands. The affinity curves were generated by performing serial dilution of the $16^{th}$ round cell-SELEX library and the unselected control library to achieve 250 nM, 125 nM, 50 nM, 25 nM, 10 nM and 2 nM concentrations.

Library affinity determination and LIGS without washing free ligands: Cells were prepared by washing with RPMI containing 200 mg/L salmon sperm DNA. 25 µL of each concentration of both libraries were incubated with 25 µL of $7.5×10^4$ Jurkat.E6 cells for 1 hr with gentle shaking. After incubation, cells were centrifuged at 7000×g for 1 min, and 45 µL of supernatant were removed. The cells were then reconstituted in 300 µL of RPMI, and binding was analyzed by flow cytometry. LIGS was performed by adding 20 µL of $7.5×10^4$ Jurkat.E6 cells, 5 µL of monoclonal antibodies and 25 µL of $16^{th}$ round ssDNA pool and then allowing competitive binding by incubation for 1 hr with gentle shaking. After incubation, supernatant containing eluted sequences was collected, kept on crushed ice, and immediately PCR-amplified for NGS preparation. An additional LIGS was performed by pre-incubating Jurkat.E6 cells with monoclonal antibodies at 66.6 nM concentrations for 30 min and washing-off the unbound mAbs by adding 3 mL RPMI. The cells were than reconstituted in CSB buffer to obtain $7.5×10^4$ Jurkat.E6 cells in 25 µL volume and 25 µL 16th round ssDNA pool was added into pre-mAb treated cells. After 45 min incubation, supernatant containing non-binding sequences was collected, kept on crushed ice, and immediately PCR-amplified for NGS preparation.

Library affinity determination and LIGS involving washing step: LIGS with the washing step was performed in a manner similar to that mentioned above, except that incubation was performed with $3.0×10^5$ cells for 45 min, followed by a washing step using 3 mL RPMI. After removing the supernatant, cells were reconstituted in 300 µL of CSB. 50 µL of resulting cell mixture were removed and analyzed by flow cytometry in order to mimic conditions for LIGS. During LIGS, 50 µL CSB containing $5.0×10^4$ cells were incubated with 5 µL of mAbs for 30 min at 25° C. At the end of this second incubation, cells were pelleted by centrifugation, and the supernatant was kept on crushed ice for PCR amplification and NGS preparation.

For all LIGS conditions (except when pre-mAb treated cells are utilized), a final mAb concentration of 33.3 nM, 30.6 nM, 27.3 nM and 33.3 nM was used for isotype control, anti-CD3 clone OKT3, anti-CD3 clone UCHT1, and anti-CD28 antibodies, respectively. Antibody binding was analyzed by secondary staining, utilizing ALEXA FLUOR® 647-conjugated Goat anti-Mouse IgG secondary antibody at a final concentration of 5 µg/mL.

Preparation of samples for NGS: Eluted molecules obtained from LIGS and enriched cell-SELEX libraries were prepared for Illumina sequencing using 16S metagenomic sequencing library protocol. Amplicon primers were ordered from IDT. The primer sequences are as follows: Forward amplicon: 5'-TCGTCGGCAGCGTCAGATGTGTATA AG AGACAG-ATCGTCTGCTCCGTCCAATA (SEQ ID NO: 21) Reverse amplicon: 5'-GTCTCGTGGGCTCGGAG ATGTGTATAAGAGACAGGCACGACCTCACACCAAA (SEQ ID NO: 22). The amplicon PCR was performed using 6 or 8 PCR cycles, and the PCR product was purified using magnetic beads (Agencourt AMPure XP). Illumina sequencing adapters and multiplexing indices were added by performing a second PCR using the Nextera XT Index Kit (Illumina, FC-131-1001), using 7 PCR cycles. The product obtained from amplicon PCR was used as a template for index PCR. The PCR product was purified and characterized by agarose gel electrophoresis and later submitted to the Genomics and Epigenomics Core Facility at Weill-Cornell Medicine for Illumina sequencing. Sequencing of samples was performed after further characterizing the product using Bioanalyzer (Agilent 2100 Bioanalyzer System). A maximum of ten samples were pooled together and sequenced by the Illumina HiSeq4000 instrument, using single-read clustering and 100 cycles.

Bioinformatics analysis: Initial analysis of the sequencing data was performed by the Computational Genomics Core at Albert Einstein College of Medicine. Preprocessing of NGS data was performed using cutadapt and a local copy of the FASTX-Toolkit. After trimming 5' and 3' constant regions and eliminating sequences without the constant regions, sequences that were not between 30 and 44 bases long were removed. The remaining sequences were then filtered to keep only high-quality reads by discarding any read that had a Phred quality score of less than 20 at a single position. Pre-processed data was further analyzed by using the FASTAptamer toolkit v1.0.11. First, FASTAptamer-Count for each library was performed, and the results were used as input for FASTAptamer-Compare and FASTAptamer-Enrich. FASTAptamer-Enrich was run for each LIGS condition, and three input files were defined as x=final enriched cell-SELEX library (i.e., Round 16), y=LIGS pool from isotype control antibody, and z=the specific monoclonal antibody (anti-CD3 or anti-CD28). (See Table 1 for a complete list of all files generated.)

TABLE 2

List showing 18 files obtained by FASTAptamer-Enrich that were further analyzed using GALAXY platform to identify specific aptamer ligands.

| File Name | # unique reads | # reads ≥ 1 RPM(x) | # of Reads ≥ 4 RPM(z)/RPM(y) |
|---|---|---|---|
| R16-J_vs_10-iso_vs_10-OKT3 | 2117980 | 65085 | 675 |
| R16-J_vs_10-iso_vs_10-UCHT1 | 1888849 | 65085 | 558 |
| R16-J_vs_10-iso_vs_10-CD28 | 1609903 | 65085 | 791 |
| R16-J_vs_20-iso_vs_20-OKT3 | 3007195 | 65085 | 180 |
| R16-J_vs_20-iso_vs_20-UCHT1 | 2806662 | 65085 | 231 |
| R16-J_vs_20-iso_vs_20-CD28 | 3446074 | 65085 | 189 |
| R16-J_vs_40-iso_vs_40-OKT3 | 2461688 | 65085 | 277 |
| R16-J_vs_40-iso_vs_40-UCHT1 | 1104291 | 65085 | 433 |
| R16-J_vs_40-iso_vs_40-CD28 | 1372050 | 65085 | 260 |
| R16-J_vs_80-iso_vs_80-OKT3 | 1565887 | 65085 | 309 |
| R16-J_vs_80-iso_vs_80-UCHT1 | 1501662 | 65085 | 337 |

TABLE 2-continued

List showing 18 files obtained by FASTAptamer-Enrich that were further
analyzed using GALAXY platform to identify specific aptamer ligands.

| File Name | # unique reads | # reads ≥ 1 RPM(x) | # of Reads ≥ 4 RPM(z)/RPM(y) |
| --- | --- | --- | --- |
| R16-J_vs_80-iso_vs_80-CD28 | 2749145 | 65085 | 238 |
| R16-J_vs_cap-iso_vs_cap-OKT3 | 2157541 | 65085 | 151 |
| R16-J_vs_cap-iso_vs_cap-UCHT1 | 2558769 | 65085 | 1366 |
| R16-J_vs_cap-iso_vs_cap-CD28 | 2280739 | 65085 | 590 |
| R15-T-SLX_vs_T-R15-Lib_vs_T-OKT3 | 1633305 | 42182 | 130 |
| R15-T-SLX_vs_T-R15-Lib_vs_T-UCHT1 | 1381965 | 42182 | 81 |
| R15-T-SLX_vs_T-R15-Lib_vs_T-CD28 | 1351403 | 42182 | 110 |

The data from FASTAptamer-Enrich were further analyzed by using the public GALAXY server to identify competitively eluted sequences by anti-CD3 and anti-CD28 antibodies. The filter tool was used to remove sequences with low copy numbers and RPM value less than 1 in the final selection library (Round 16 with Jurkat.E6 cells and Round 15 with Primary T-cells). Remaining sequences were further filtered to identify sequences that showed at least 4-fold enrichment (enrichment z/y≥4) in anti-CD3 pools (OKT3 and UCHT1) against isotype control. Sequences that showed any enrichment towards CD28 against isotype control (enrichment z/y>1) were also identified. The compare tool was used to find non-matching rows between the datasets obtained from anti-CD3 and anti-CD28 analyses to identify CD3 and CD28 specific sequences. The ClustalW (multiple sequence alignment program) on GALAXY.

Aptamer candidate screening and specificity analyses: Initial aptamer screening was performed by incubating 500 nM of fluorophore-labeled aptamer candidates or random ssDNA molecules with $2.0 \times 10^5$ Jurkat.E6 (T-cell leukemia) and MOLT-3 (acute lymphoblastic leukemia, TCR−/CD3−, CD28+) separately in a total volume of 100 μL at 25° C. for 1 hr. After washing twice with 3 mL of RPMI, cells were reconstituted in 250 μL of RPMI, and binding events were analyzed using flow cytometry (BD FACScan). Potential aptamer candidates with binding above 25% when normalized against random control towards TCR-CD3ε expressing Jurkat.E6 cells were further screened utilizing two additional negative cell lines: BJAB (Burkitt's lymphoma) and Toledo (non-Hodgkin's B-cell lymphoma).

Binding affinity determination: Binding affinities of selected aptamers against Jurkat.E6 cells were determined by incubating a range of aptamer concentrations (1 nM to 250 nM) with $2.0 \times 10^5$ cells at 25° C. for 1 hr. Cells were then washed once using 3 mL of RPMI, and binding events were analyzed by flow cytometry. $K_d$ values were obtained by plotting the specific median fluorescence intensities (Aptamer Fluorescence Intensity—Random DNA Fluorescence Intensity) against each concentration on GraphPad Prism software, as previously described.

Cross competition: 3' Biotin-TEG-modified ZUCH-1 (highest affinity aptamer) was purchased from IDT and used for competitive binding experiments. The concentrations of fluorescently (5'FAM)-labeled aptamers were chosen based on their binding affinities against Jurkat.E6 cells. 100 nM ZOKT-2, 200 nM ZUCH-3, 300 nM ZUCH-4 and 500 nM for ZUCH-5 were used. An excess concentration of 1 μM of the competitor was used against each (5'FAM)-labeled aptamer. $2.0 \times 10^5$ Jurkat.E6 cells were incubated with fluorescently labeled aptamers in the presence of the competitor, or CSB, as control in a total volume of 100 μL at 25° C. for 1 hr. Cells were then washed once using 3 mL of RPMI, and binding events were analyzed by flow cytometry.

Specificity assay against TCR/CD3ε CRISPR knockout Jurkat.E6 cells: In order to evaluate target specificity of the selected aptamers against TCR-CD3ε, a specificity assay was conducted with TCR/CD3ε double knockout Jurkat cells obtained from Synthego. Jurkat.E6 cells used in Cell-SELEX (gift from the Huse Lab, MSKCC) as well as Synthego's wild-type Jurkat cells, were used as positive cell lines. 250 nM of the highest affinity aptamer, ZUCH-1, was incubated with $1.5 \times 10^5$ cells in a total volume of 150 μL at 25° C. for 1 hr. Cells were washed twice with 2 mL of RPMI at the end of incubation and reconstituted in 250 μL of RPMI. Binding events were analyzed using flow cytometry. CSB used for this experiment consisted of 200 mg/L tRNA, 200 mg/L salmon sperm DNA and 2 g/L BSA formulated in RPMI-1640 medium.

Determination of antigen specificity by aptamer/anti-CD3 antibody competition: To further validate specificity of the selected aptamers against CD3e, competitive binding experiments were performed using both anti-CD3 antibodies (OKT3 and UCHT1 clones) and anti-CD28 antibody as positive control. First, $8.0 \times 10^5$ Jurkat.E6 cells were incubated with 300 nM final concentration of each mAb at 25° C. for 30 min. The cells were then washed once with 3 mL of RPMI and reconstituted in 300 μL of CSB. Then, 50 μL of CSB, containing $1.0 \times 10^5$ mAb-bound cells, was incubated with 50 μL of either ZUCH-5 or random ssDNA for an additional 30 min at 25° C. The cells were washed once with 3 mL of RPMI and analyzed using flow cytometry. Secondary staining was also performed to analyze binding of the mAbs using ALEXA FLUOR® 647-conjugated Goat anti-Mouse IgG secondary antibody for a final concentration of 5 μg/mL, and this was followed by flow cytometry analysis.

Results

Evolution of DNA ligands against TCR-CD3ε-positive cells: LIGS integrates antibody antigen interactions or receptor ligand-interaction and in vitro evolution to robustly identify functional nucleic acid ligands against predetermined cellular receptors. The variation of LIGS described here is significantly different from the previously introduced LIGS method. Bioinformatics analysis was added and, for the first time, incorporated primary samples to SELEX and expanded the number of mAbs to streamline the ligand discovery process. The modified LIGS method is outlined in FIG. 8G.

Figure 8G:
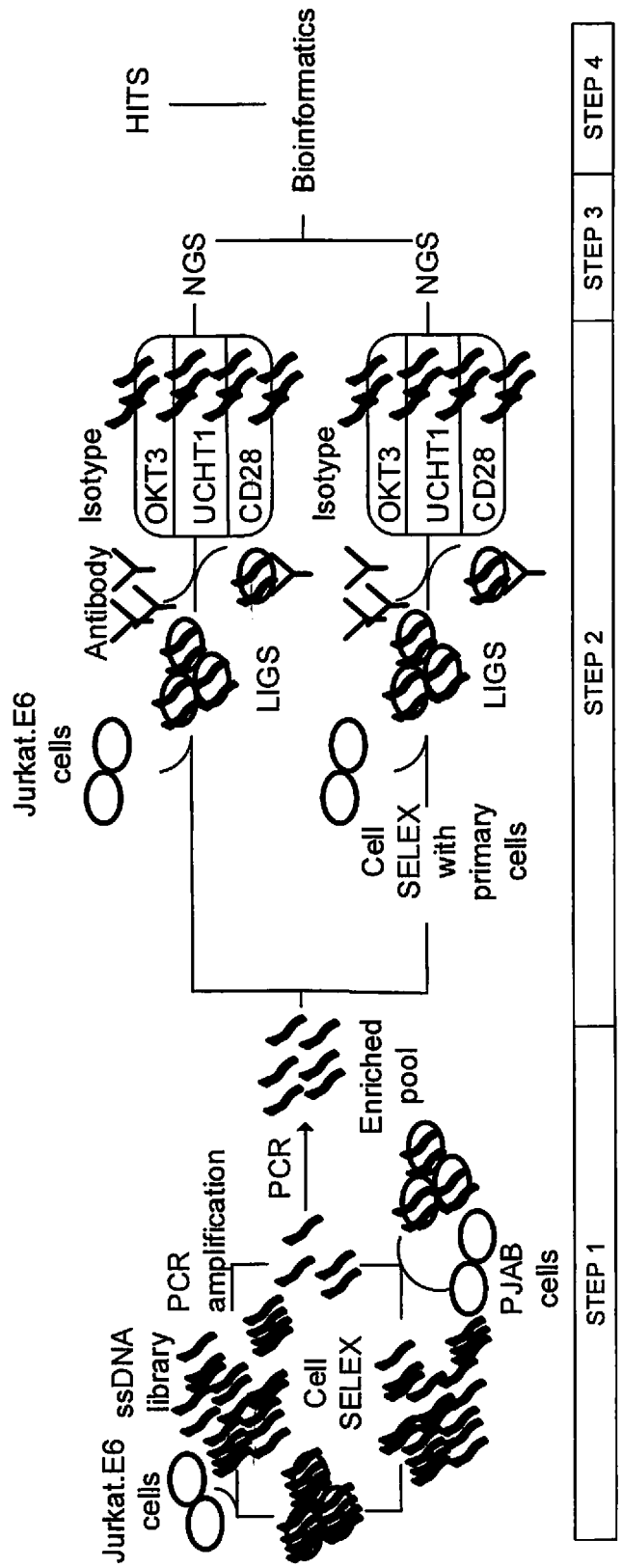
FIG. 8G depicts the overall workflow of Ligand-guided Selection (LIGS)

FIG. 8G depicts the overall workflow of Ligand-guided Selection (LIGS). Prior to cell-SELEX, the target Jurkat.E6 cells were prepared by routine monitoring of CD3ε and TCR expression levels, using respective OKT3 and UCHT1 mAbs and anti-human TCRαβ, by flow cytometry. Next, cell-SELEX was carried out to evolve potential DNA ligands against Jurkat.E6 cells. After ten rounds of cell-SELEX, an enrichment of DNA ligands towards Jurkat.E6 cells was observed using flow cytometry (FIG. 9A). To remove nonspecific binders potentially enriched in the cell-SELEX pool, a negative SELEX step was introduced utilizing BJAB (Burkitt's lymphoma) cells at round 12. BJAB cells were used because these cells express variants of immunoglobulins (Igs), but they do not express the TCR-CD3 complex itself. Also, it is known that B-cells interact with oligonucleotides containing CpG motifs through the BCR receptor. Therefore, the DNA sequences enriched in the cell-SELEX pool that interact with the Igs could be removed by this negative selection step, while enriching DNA ligands with affinity for the desired TCR-CD3ε.

Figure 9D:
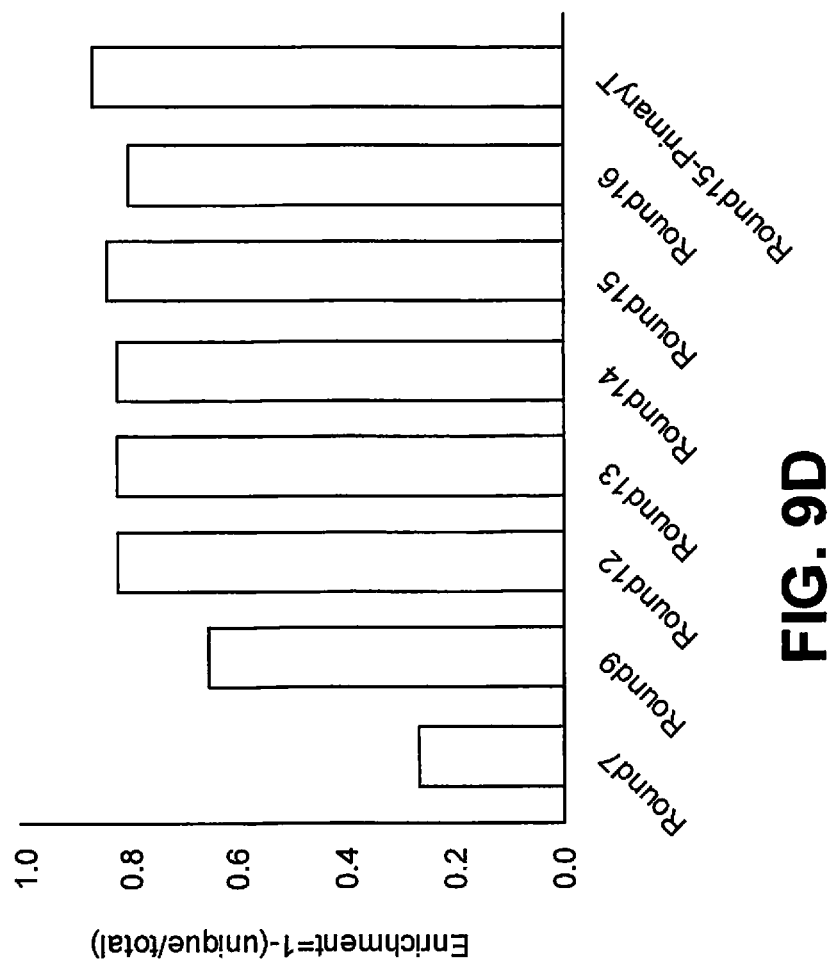
FIG. 9D is a bioinformatics analysis on the sequencing data obtained for each round of cell-SELEX showing significant enrichment at round 13 of cell-SELEX. Enrichment on y-axis is defined as $$1 - \frac{\text{number of unique sequences}}{\text{total number of sequences}};$$
Figure 9E:
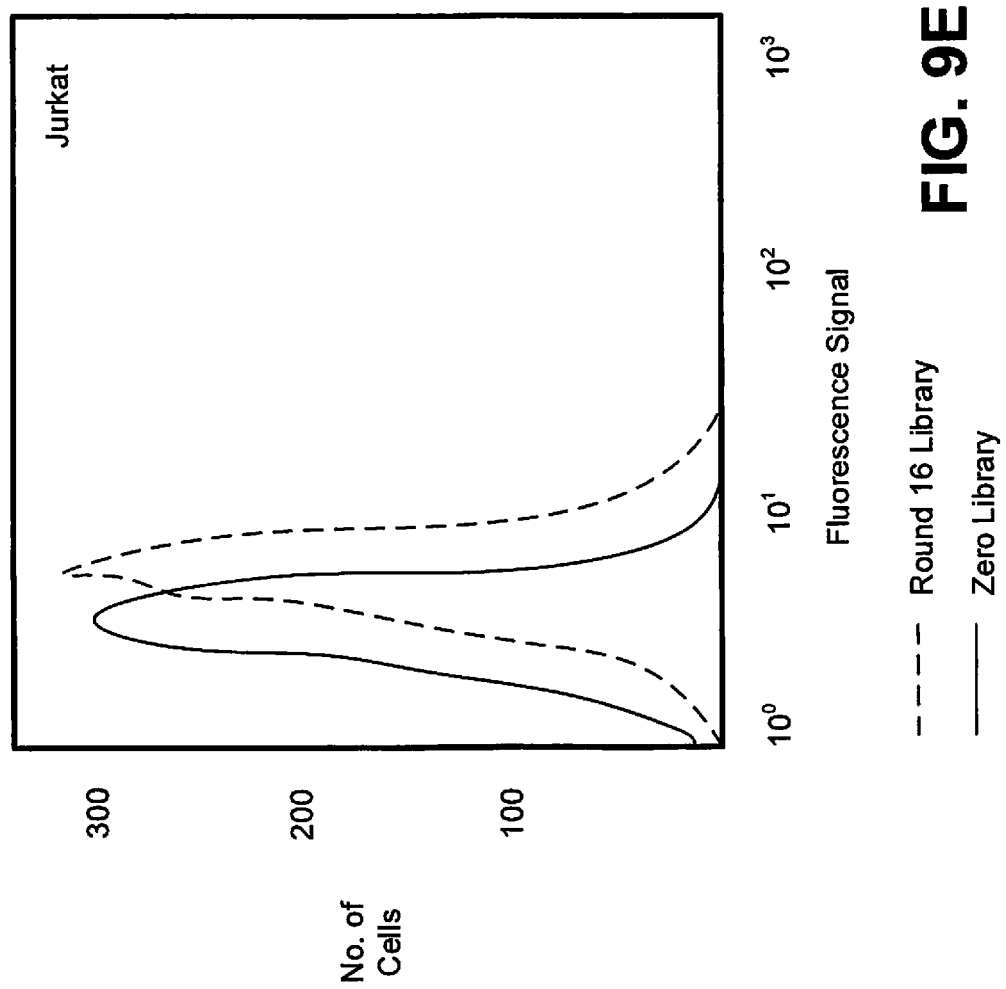
FIG. 9E is a flow cytometry analysis of binding of cell-SELEX library to Jurkat.E6 cells at round 16.

Following the negative selection, one more round of positive selection was conducted. A specific enrichment of DNA ligands towards Jurkat.E6 cells, but not BJAB cells, was observed at the 13th round of cell-SELEX (FIG. 9B and FIG. 9C). To investigate the evolution of individual sequences, the evolved cell-SELEX pools from multiple rounds were sequenced and analyzed, using the FASTAptamer toolkit and the GALAXY platform. Flow cytometry analysis provided qualitative evidence suggesting enrichment of a cell-SELEX library towards Jurkat.E6 cells. Since the nature of enrichment of specific sequences as a function of SELEX can be evaluated by sequencing individual cell-SELEX pools, individual pools of cell-SELEX were sequenced and the enrichment of the cell-SELEX pool was analyzed. The analyses from flow cytometry and Illumina data using the FASTAptamer toolkit and the GALAXY platform, showed significant enrichment of cell-SELEX at round 13 of cell-SELEX (FIG. 9D). At this point, three additional cell-SELEX cycles were performed to ensure full evolution of the cell-SELEX pool against Jurkat.E6 cells, ending it at round 16 (FIG. 9E).

However, at round 15 of cell-SELEX, one fraction of the cell-SELEX pool was utilized in one round of SELEX against TCR-CD3ε-positive primary T-cells isolated from PBMCs of healthy donors. This step was introduced to remove DNA ligand bias towards cultured cells. The resulting two pools of DNA aptamer ligands from round 16 against Jurkat.E6 cells and round 15 utilizing primary T-cells were PCR-amplified and utilized in LIGS.

Ligand-guided Selection to elute CD3ε-specific ligands: LIGS assumes that an evolved cell-SELEX pool against cultured Jurkat.E6 and human T-cells contains specific DNA ligands against TCR-CD3£ and that the concentration of each DNA ligand in the evolved cell-SELEX pool is below its $K_d$. Since this method is rooted in differences in $K_d$ of ligand-receptor interactions, the affinity constant for each antibody and affinity constant of evolved DNA pool towards Jurkat.E6 cells were determined prior to performing LIGS.

Figure 11D:
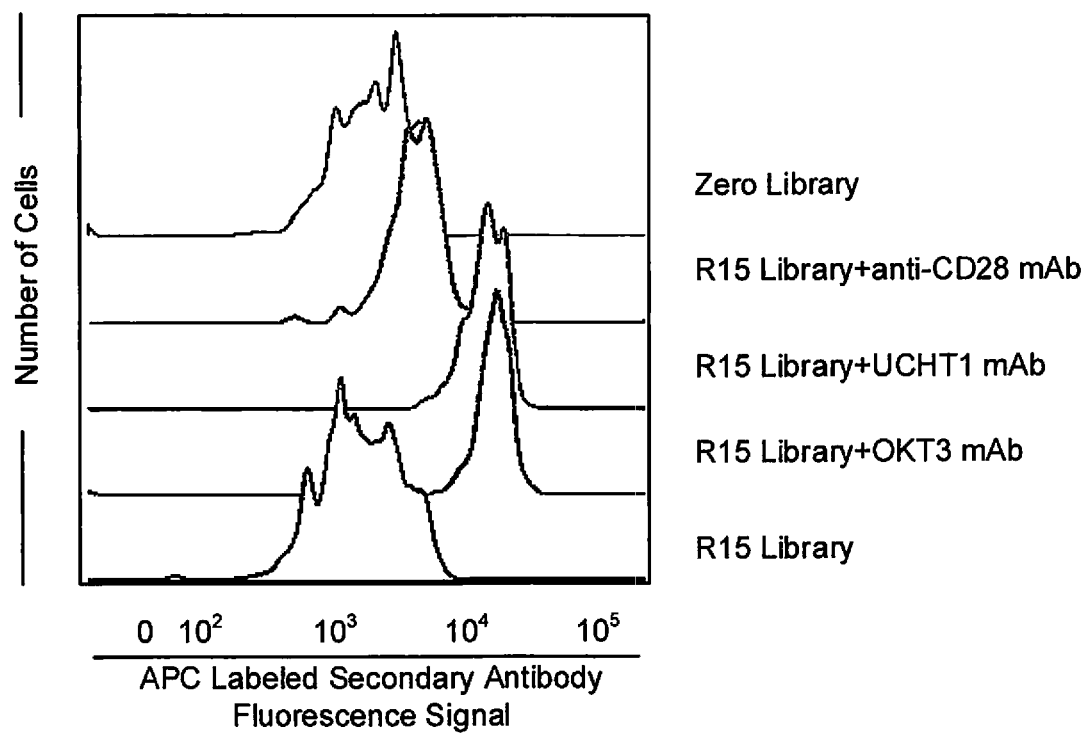
FIG. 11D depicts corresponding secondary-antibody staining that corresponds to the analysis of FIG. 11C. The graph depicts the analysis of flow cytometry data obtained for secondary staining of the Primary T-cells used during LIGS.

The calculated affinities are 1.5±0.27 nM for anti-CD3 clone OKT3, 1.4±0.36 nM for anti-CD3 clone UCHT1, and 1.6±0.22 nM for anti-CD28 antibody (affinity curves are in FIG. 10A, FIG. 10B and FIG. 10C). The affinity of the enriched pool containing DNA ligands against Jurkat.E6 cells was measured by considering two scenarios. First, the affinity of the enriched pool towards Jurkat.E6 cells was determined in the presence of free ligands, which was found to be 19.5±1.96 nM (FIG. 11A). Second, the affinity of the enriched cell-SELEX pool was determined in the absence of free ligands, which was 78.3±14.3 nM (FIG. 11B). LIGS tends to show bias towards the elution of low-affinity aptamers, which, therefore, requires an extra step of post-SELEX modification to enhance affinity. This challenge was addressed by manipulating the concentration of evolved cell-SELEX library used in LIGS. Thus, LIGS was performed using concentrations equal to half the $K_d$ of the enriched DNA pool, which was calculated based on the affinity curves constructed for each condition, as outlined above. Using this strategy, LIGS was performed at 10 nM (equal to half the KO and 20 nM (equal to the $K_d$) in the presence of free DNA ligands, as well as at 40 nM (equal to half the $K_d$) and 80 nM (equal to the $K_d$) in the absence of free DNA ligands. Several antibodies were used in LIGS. First, LIGS was performed using an isotype control antibody to account for the high off-rate of DNA ligands, which might potentially be contaminating LIGS pools. Second, two mAbs against CD3ε receptor clones (OKT3 and UCHT1) were used to competitively elute specific DNA ligands against the desired receptor.

Third, anti-CD28 mAb targeting a different receptor expressed on the target cells was used. The third control was used to investigate off-target sequences eluted by mAb interacting with cell-surface receptor, rather than true competition. All mAbs were used in concentrations above their respective $K_d$s to promote complete formation of antibody-antigen complex. The supernatant from each condition containing eluted DNA ligands was PCR-amplified and sequenced by Illumina; all the sequencing pools obtained are listed in Table 2. In a third scenario, the competing mAb was washed post-incubation, and free ligands were retained in the cell-SELEX pool, again at concentration equal to half the $K_d$ to elute all ligands competing for the same antigen. Finally, to identify sequences specific to TCR-CD3ε in primary T-cells, an additional LIGS was performed against T-cells isolated from PBMCs (FIG. 11C). Because the affinity of the evolved cell-SELEX pool against human T-cells was not investigated, 250 nM was used as the final concentration of evolved cell-SELEX pool against T-cells. Similarly, to elute specific sequences, all four antibodies were used. The supernatant containing competitively eluted sequences was collected and PCR-amplified for Illumina sequencing.

TABLE 2

List of all sequencing library pools showing sample names and descriptions.

| Sample Name | Description |
| --- | --- |
| R7-J | Library pool obtained after 7 rounds of cell-SELEX against Jurkat cells |
| R9-J | Library pool obtained after 9 rounds of cell-SELEX against Jurkat cells |
| R12-J | Library pool obtained after 12 rounds of cell-SELEX against Jurkat cells |
| R13-J | Library pool obtained after 13 rounds of cell-SELEX against Jurkat cells |
| R14-J | Library pool obtained after 14 rounds of cell-SELEX against Jurkat cells |
| R15-J | Library pool obtained after 15 rounds of cell-SELEX against Jurkat cells |
| R15-T | Library pool obtained after 14 rounds of cell-SELEX against Jurkat cells and 1 round against human T-cells |

TABLE 2-continued

List of all sequencing library pools showing sample names and descriptions.

| Sample Name | Description |
|---|---|
| R16-J | Library pool obtained after 16 rounds of cell-SELEX against Jurkat cells |
| 10-iso | Supernatant from LIGS: 10 nM of $16^{th}$ round library with isotype control antibody |
| 10-OKT3 | Supernatant from LIGS: 10 nM of $16^{th}$ round library with anti-CD3 (clone OKT3) antibody |
| 10-UCHT1 | Supernatant from LIGS: 10 nM of $16^{th}$ round library with antiCD3 (clone UGHT1) antibody |
| 10-CD28 | Supernatant from LIGS: 10 nM of $16^{th}$ round library anti-CD28 antibody |
| 20-ISO | Supernatant from LIGS: 20 nM of $16^{th}$ round library with isotype control antibody |
| 20-OKT3 | Supernatant from LIGS: 20 nM of $16^{th}$ round library with anti-CD3 (clone UGHT1) antibody |
| 20-UGHT1 | Supernatant from LIGS: 20 nM of $16^{th}$ round library with anti-CD3 (clone UGHT1) antibody |
| 20-CD28 | Supernatant from LIGS: 20 nM of $16^{th}$ round library with anti-CD28 antibody |
| 40-iso | Supernatant from LIGS: 40 nM of $16^{th}$ round library with isotype control antibody |
| 40OKT3 | Supernatant from LIGS: 40 nM of $16^{th}$ round library with anti-CD3 (clone OKt3) antibody |
| 40-UGHT1 | Supernatant from LIGS: 40 nM of $16^{th}$ round library with anti-CD3 (clone UGHT1) antibody |
| 40-CD28 | Supernatant from LIGS: 40 nM of $16^{th}$ round library with anti-CD28 antibody |
| 80-iso | Supernatant from LIGS: 80 nM of $16^{th}$ round library isotype control antibody |
| 80-OKT3 | Supernatant from LIGS: 80 nM of $16^{th}$ round library with anti-CD3 (clone OKT3) antibody |
| 80-UCHT1 | Supernatant from LIGS: 80 nM of $16^{th}$ round library with anti-CD3 (clone UGHT1) antibody |
| 80-CD28 | Supernatant from LIGS: 80 nM of $16^{th}$ round library with anti-CD28 antibody |
| cap-iso | Supernatant from LIGS: isotype control antibody, removed free mAb and 10 nM of $16^{th}$ round library |
| cap-OKT3 | Supernatant from LIGS: anti-CD3 (clone OKT3) antibody, removed free mAb, 10 nM of $16^{th}$ round library |
| Cap-UGHT1 | Supernatant from LIGS: anti-CD3 (clone) UCHT1) antibody, removed free mAb, 10 nM of $16^{th}$ round library |
| Cap-CD28 | Supernatant from LIGS: anti-CD28 antibody, removed free mAb, 10 nM of $16^{th}$ round library |
| T-R15-Lib | Supernatant from LIGS: 250 nM of $15^{th}$ round library from T-cell selection only |
| T-OKT3 | Supernatant from LIGS: 250 nM of $15^{th}$ round library from T-cell selection with anti-CD3 (clone OKT3) mAb |
| T-UCHT1 | Supernatant from LIGS: 250 nM of $15^{th}$ round library from T-cell selection with anti-CD3 (clone UCHT1) mAb |
| T-CD28 | Supernatant from LIGS: 250 nM of $15^{th}$ round library from T-cell selection with anti-CD28 mAb |

Figure 12A:
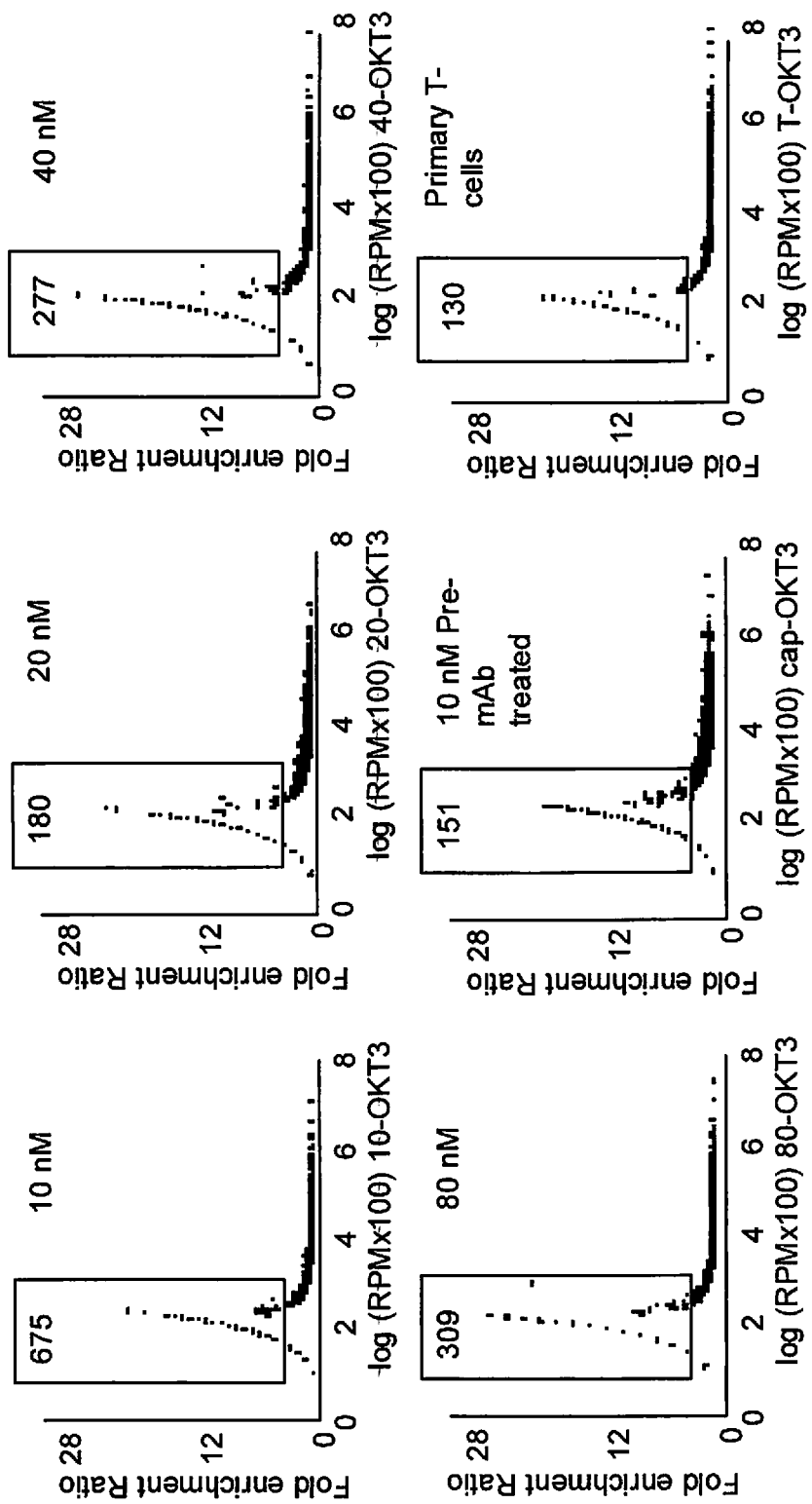
FIG. 12A shows FASTAptamer-Enrich data with fold enrichment ratio ($RPM_x/RPM_y$) plotted as a function of the abundance in OKT3 mAb eluted pools, showing the number of sequences specific to OKT3 mAb used in each LIGS condition.
Figure 12B:
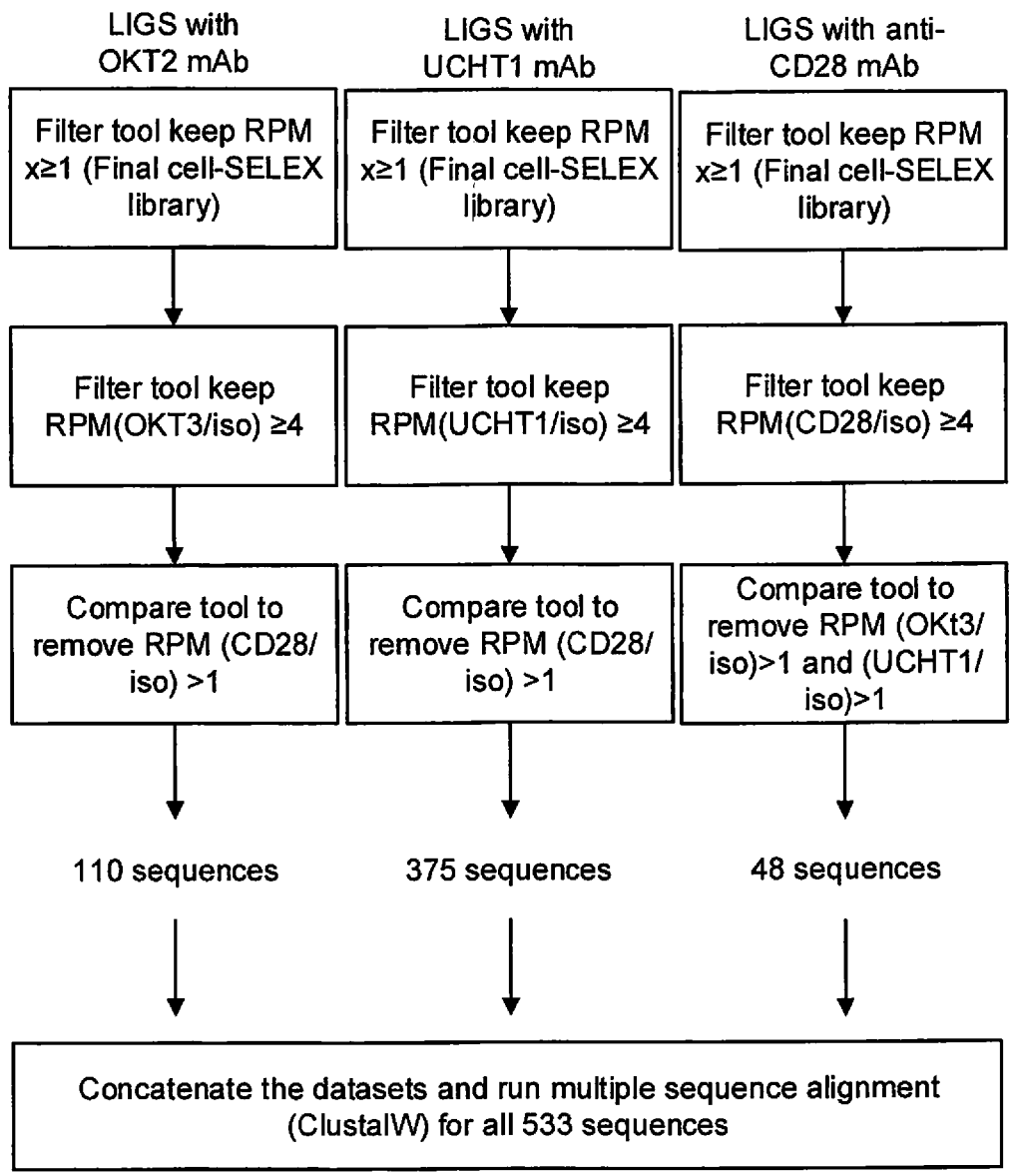
FIG. 12B depicts a schematic diagram summarizing the downstream analysis on FASTAptamer-Enrich data performed using GALAXY platform.

Bioinformatics analysis of LIGS sequencing data to identify CD3ε-specific sequences: A previously reported bioinformatics toolkit, FASTAptamer, was used to analyze sequences resulting from Illumina sequencing. Using FASTAptamer, the read counts of every unique sequence within each sequencing pool were normalized against the total number of sequences obtained by Illumina sequencing as reads per million (RPM). The sequencing data were then compared between LIGS pools for fold-enrichment ratios: $RPM_y/RPM_x$, $RPM_z/RPM_y$, or $RPM_z/RPM_x$ where x=total number of enriched sequences resulting from the final round of cell-SELEX, y=sequences nonspecifically eluted when isotype antibody was used, and z=specifically eluted sequences by mAbs and tabulated using the FASTAptamer-Enrich tool. Data processed by FASTAptamer were further subjected to downstream analysis to identify target-specific sequences using the public GALAXY server. The fold-enrichment values ($RPM_z/RPM_y$) were plotted as a function of the abundance in mAb-eluted pools (FIG. 12A for OKT3 mAb), which showed the number of sequences specific to each mAb used in each LIGS condition. Fold enrichment values were plotted for all mAbs used in LIGS and observed the same correlation. Based on these findings, a set criterion was defined as $RPM_z/RPM_y \geq 4$ to filter off-target sequences and identify sequences potentially outcompeted by each specific mAb (FIG. 12B). Interestingly, the abundance of sequences did not correlate with specificity. The filtering of sequences, as a function of experimental conditions used in LIGS was performed in the order as outlined in FIG. 12B. First, sequences were eliminated using filter cut-off at 1 RPM for parameter X against sequence files corresponding to the final round of cell-SELEX, which removed any contaminating sequences from sample preparation and sequencing. Second, the predicted cut-off value of 4 for $RPM_{mAb}=z/RPM_{Iso}=y$ was used to remove nonspecifically eluted sequences. The third step was implemented to eliminate off-target sequences potentially contaminating the LIGS pool. Thus, any sequence with $RPM_{CD28}/RPM_{Iso}>1$ was removed from the sequences obtained at step two. At the end of step three, a total of 485 (452 unique sequences and 33 common to both OKT3 and UCHT1 mAbs) sequences were obtained specific for CD3ε and 48 sequences were obtained against CD28, as shown in the Venn diagram (FIG. 12C). At the fourth and final step, all analyzed sequences were aligned using ClustalW to determine individual aptamer families. Despite the three steps employed to remove off-target sequences, some sequences with mutations resulting from anti-CD28 competition appeared among the families from 485 sequences identified against CD3ε. This result could be attributed to the compare tool on GALAXY platform, which does not eliminate sequences with one or more point mutations as identical hits. The aligned sequences were further categorized into individual sequence families, and sequences that showed homology were synthesized to identify aptamer sequences. One family of sequences appeared with five out of six conditions of LIGS using either OKT3 or UCHT1, and these were synthesized first (FIG. 12D).

Figure 13A:
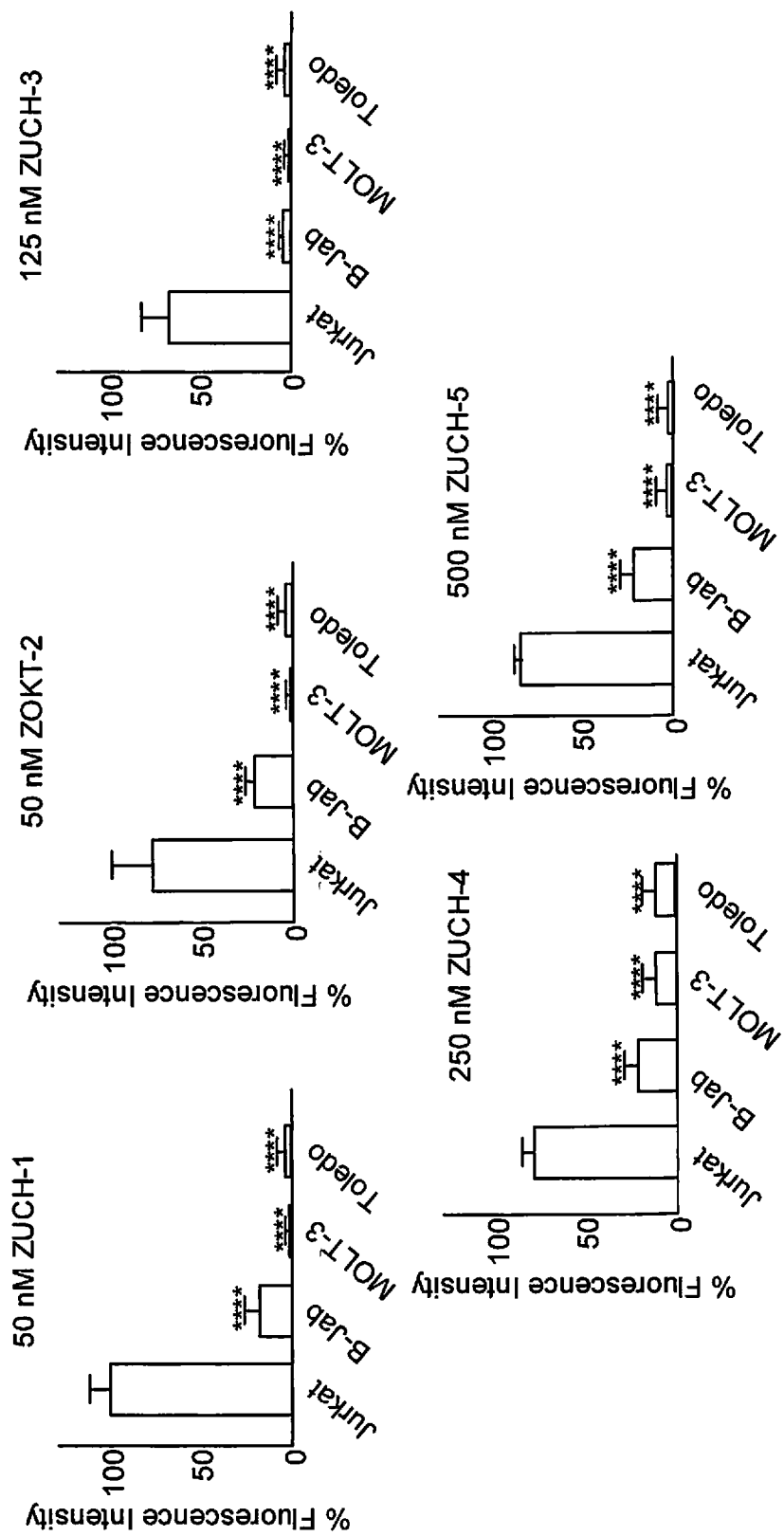
FIG. 13A shows fluorescence graphs from three independent specificity analyses of ZUCH-1, ZOKT-2, ZUCH-3, ZUCH-4 and ZUCH-5 against Jurkat.E6, B-Jab, MOLT-3 and Toledo, (One-way ANOVA using Tukey's multiple comparisons test performed on GraphPad Prism ****: p≤0.0001)
Figure 13B:
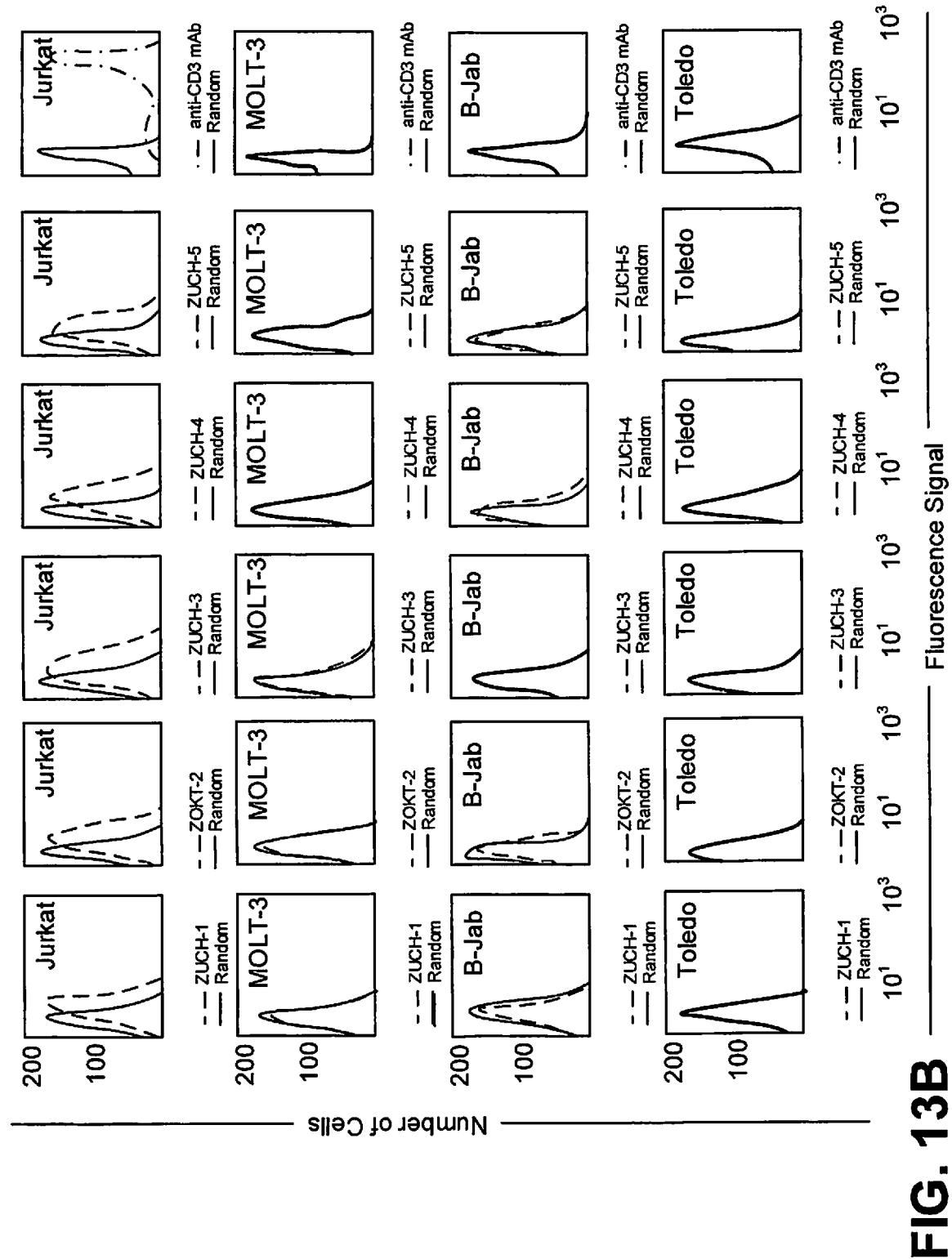
FIG. 13B depicts the results of binding ZUCH-1, ZOKT-2, ZUCH-3, ZUCH-4 and ZUCH-5 with Jurkat.E6, B-Jab, MOLT-3 and Toledo cells and data for anti-CD3 mAb staining of each cell line.
Figure 13C:
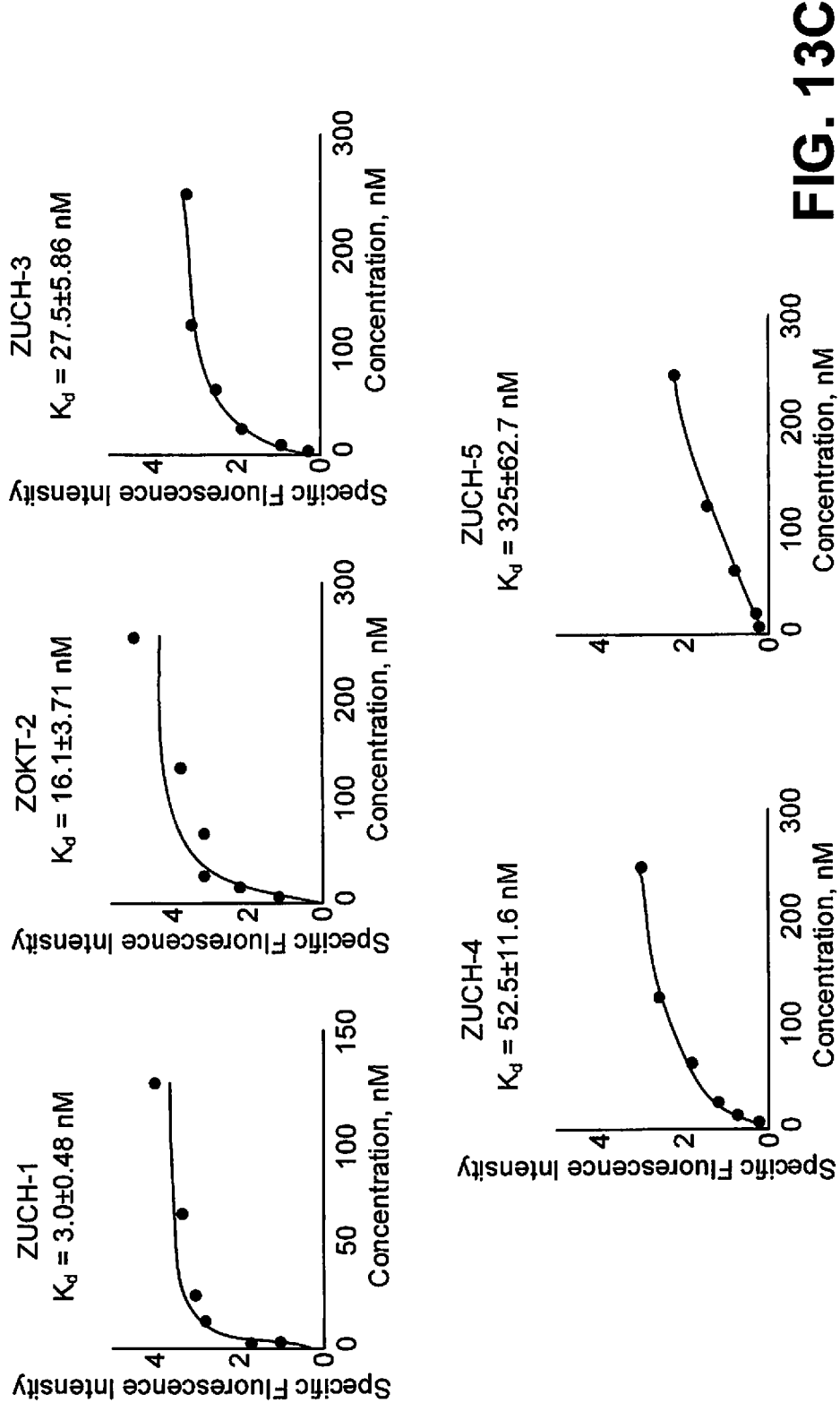
FIG. 13C depicts the results of an affinity analysis of ZUCH-1, ZOKT-2, ZUCH-3, ZUCH-4 and ZUCH-5 against Jurkat.E6 cells at 25° C. $K_d$ values were obtained by plotting the specific median fluorescence intensities against each concentration on GraphPad Prism software using one-site specific binding.

Characterization of aptamer candidates: Eight aptamer candidates were identified by bioinformatics analysis, all of which were tested against TCR-CD3ε-expressing Jurkat.E6 cells, as well as three negative cell lines that do not express TCR-CD3ε. Out of the eight aptamers tested, five aptamers were found to be specific towards Jurkat.E6 cells. The criteria for positivity was defined as $$\frac{\text{aptamer} - \text{random}}{\text{random}} \times 100 > 25\%$$

compared to random sequence against positive cells (FIG. 13A and histograms are in FIG. 13B). The affinity of the five positive aptamers was tested against Jurkat.E6 cells. As expected, the affinities correlated to the LIGS conditions used to elute each aptamer, suggesting that the manipulation of concentration during LIGS leads to elution of higher-affinity aptamers. Aptamer ZUCH-1 shows a $K_d$ of 3.0±0.48 nM (affinity curve in FIG. 13C, the highest affinity among all five aptamers. This aptamer was eluted by UCHT1 in the absence of free ligand at Bmax/2 concentration of cell-SELEX pool in LIGS.

Figure 13D:
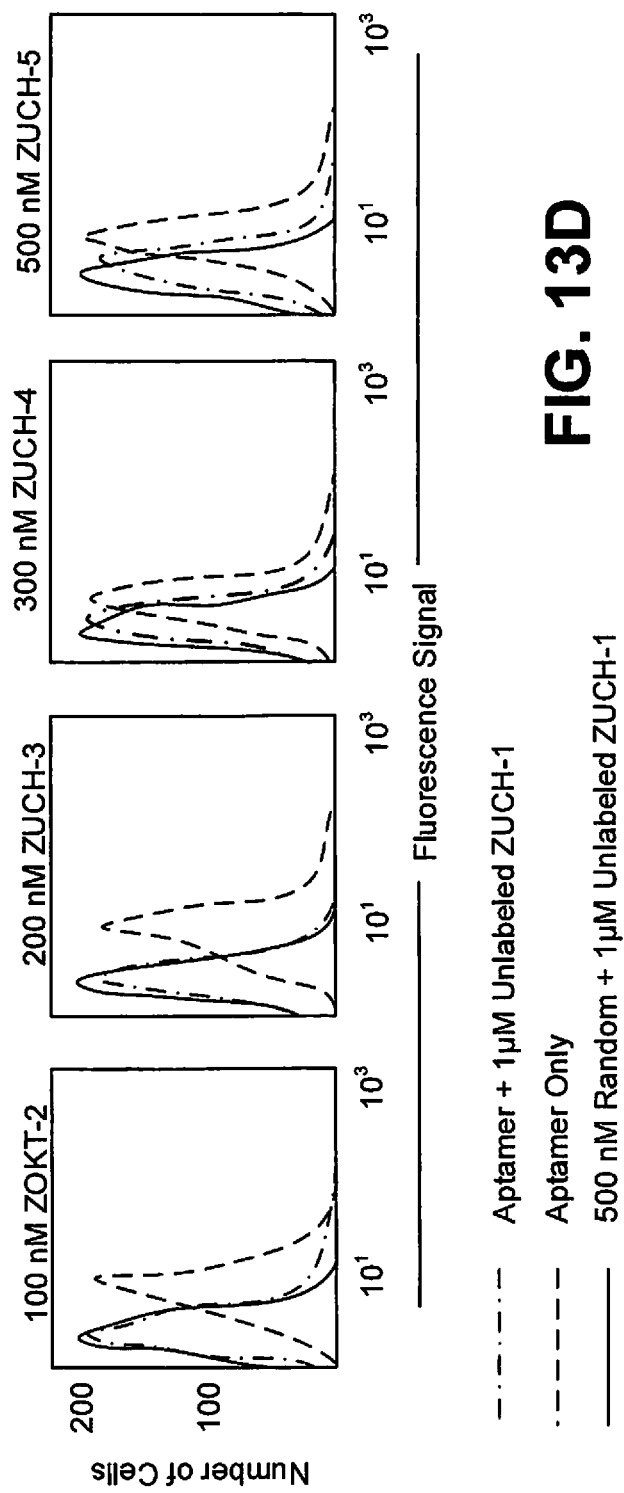
FIG. 13D depicts fluorescence graphs of the binding of ZOKT-2, ZUCH-3, ZUCH-4 and ZUCH-5 with Jurkat.E6 cells in the presence of unlabeled labeled ZUCH-1 as a competitor.
Figure 13E:
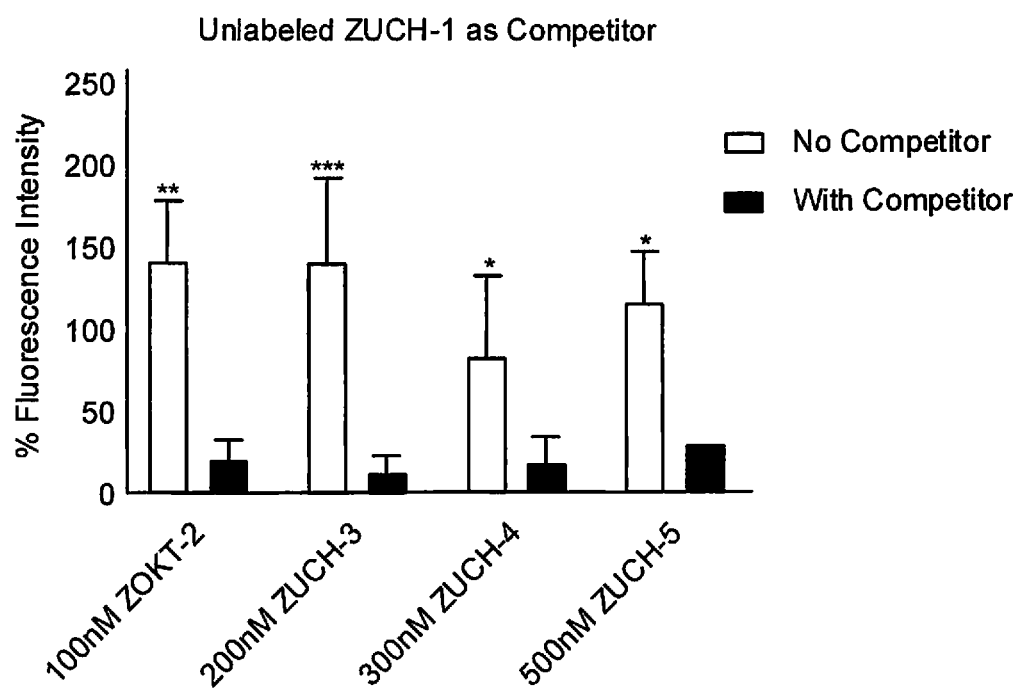
FIG. 13E illustrates graphs showing the overall conclusion from three independent analyses for FIG. 13D. (Two-way ANOVA and Holm-Sidak's multiple comparisons test performed on GraphPad Prism *: 0.0001≤p≤0.001, : 0.001≤p≤0.01 and *: 0.01≤p≤0.05)

Aptamer ZUCH-5 showed an affinity of 325±62.7 nM (affinity curve FIG. 13C), which correlated to masking of the epitope by a mAb prior to incubation with the enriched pool. The LIGS experiment performed in the presence of free ligands at 10 nM cell-SELEX pool with OKT3 yielded aptamer ZOKT-2 with $K_d$ of 16.1±3.71 nM (affinity curve FIG. 13C) and aptamer ZUCH-4 with $K_d$ of 52.5±11.6 nM (affinity curve FIG. S3), which was eluted when 20 nM cell-SELEX pool was used in the presence of free ligand in LIGS. One aptamer, ZUCH-3, was identified as T-cell-specific with $K_d$ of 27.5±5.86 nM (affinity curve FIG. 13C). Typically, SELEX against single proteins leads to a family of sequences with variable mutations. Since the five aptamers were identified by LIGS as specific with high sequence homology, all five aptamers might be binding to the same region of TCR-CD3ε. A cross-competition of the higher-affinity ZUCH-1 was performed against all four lower-affinity aptamers carrying FAM labels. The cross-competition experiment showed that all four low-affinity aptamers competed with ZUCH-1 for the same epitope, suggesting that all five aptamers had evolved against the same epitope of the TCR-CD3ε complex in Jurkat.E6 cells (FIG. 13D and FIG. 13E).

Figures 14A, 14B, 14C:
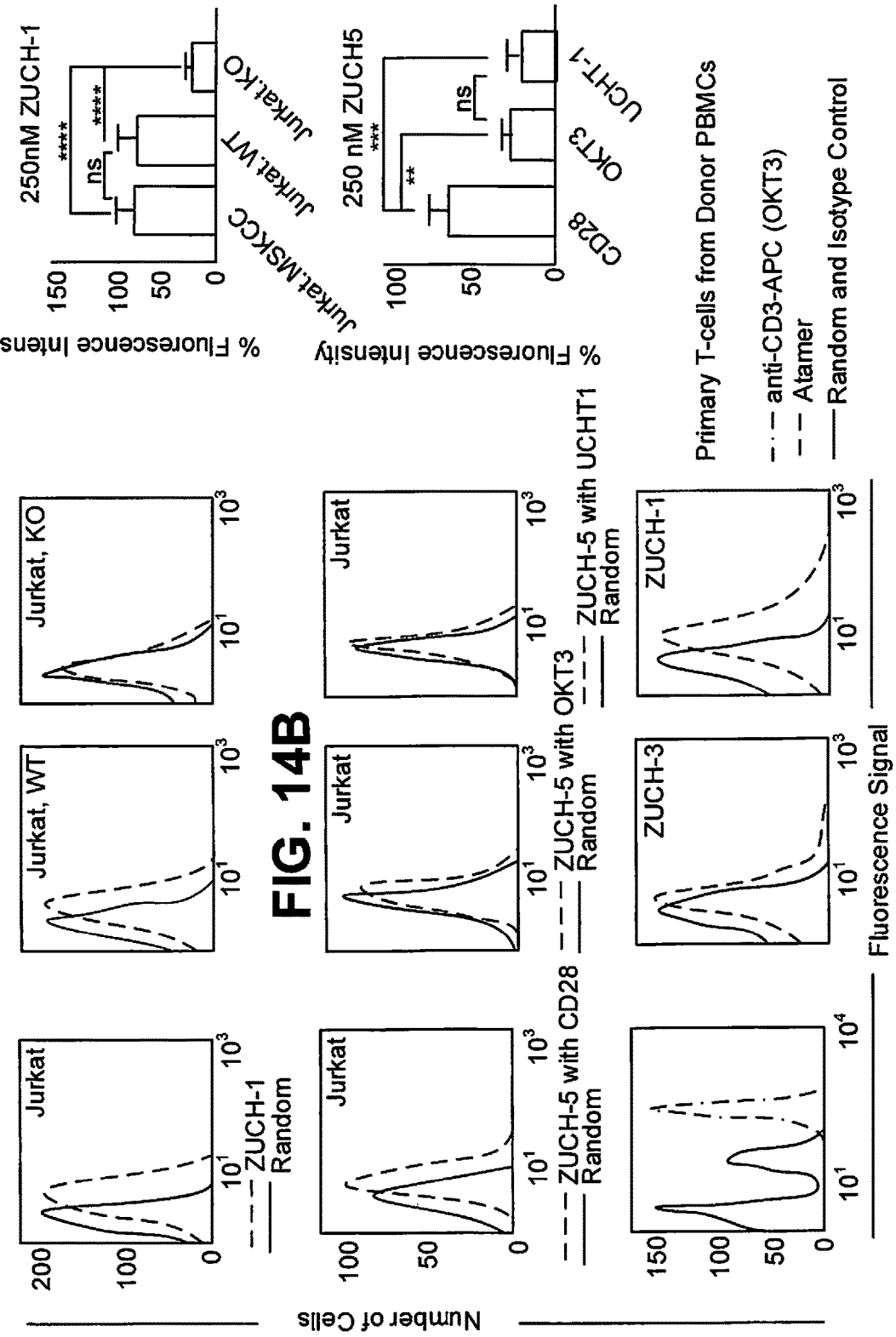
FIG. 14A depicts the binding of highest affinity aptamer ZUCH-1 against Jurkat.E6 cells used for cell-SELEX, wild-type Jurkat cells obtained from Synthego, and double knockout Jurkat cells from Synthego and conclusion from six independent specificity analyses.
FIG. 14B depicts the competitive binding of lowest affinity aptamer ZUCH-5 with Jurkat.E6 cells in the presence of anti-CD28, OKT3 and UCHT1 antibodies and overall conclusion from three independent analyses (Ordinary One-way ANOVA using Tukey's multiple comparisons test performed on GraphPad Prism ****: $p \leq 0.0001$)
FIG. 14C depicts the binding of ZUCH-1 and ZUCH-3 against human T-cells isolated from donor PBMCs. (Ordinary One-way ANOVA using Tukey's multiple comparisons test performed on GraphPad Prism *: $0.0001 \leq p \leq 0.001$ and : $0.001 \leq p \leq 0.01$). See FIG. 16 for corresponding secondary-antibody staining.
Figure 15:
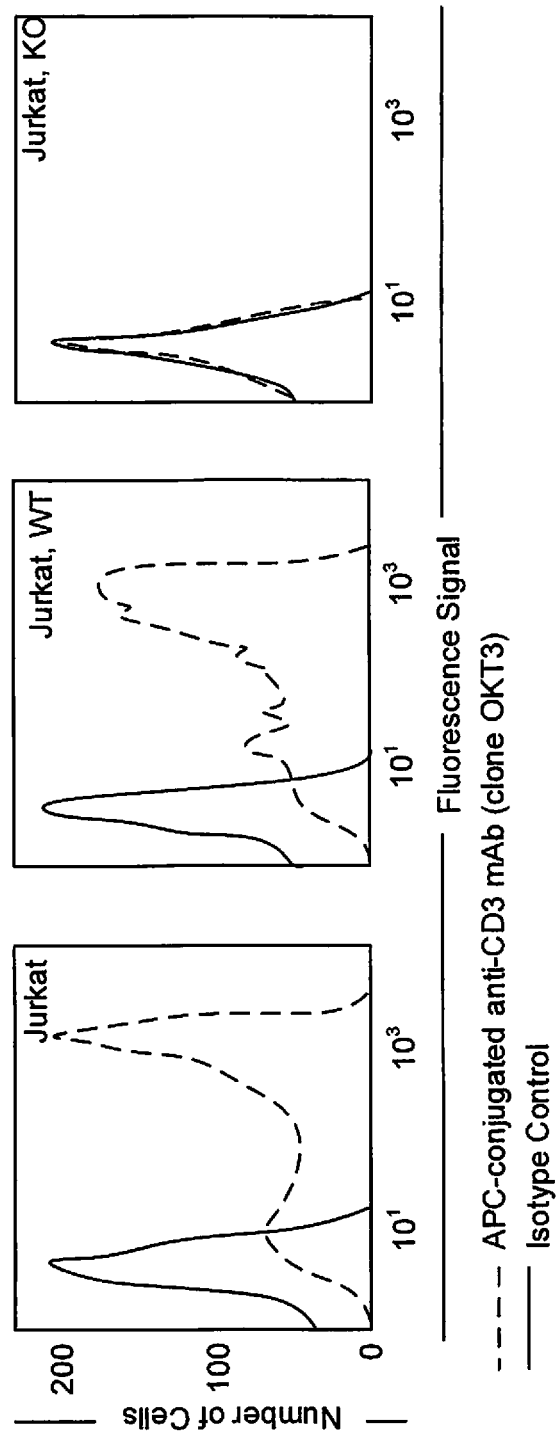
FIG. 15 depicts graphs resulting from a flow cytometry analysis showing that wild-type Jurkat cells obtained from Synthego are positive for TCR-CD3 complex while the double knockout Jurkat cells obtained from Synthego do not express TCR-CD3 complex. APC-conjugated anti-CD3 mAb (clone OKT3) was used for the analysis.
Figure 16:
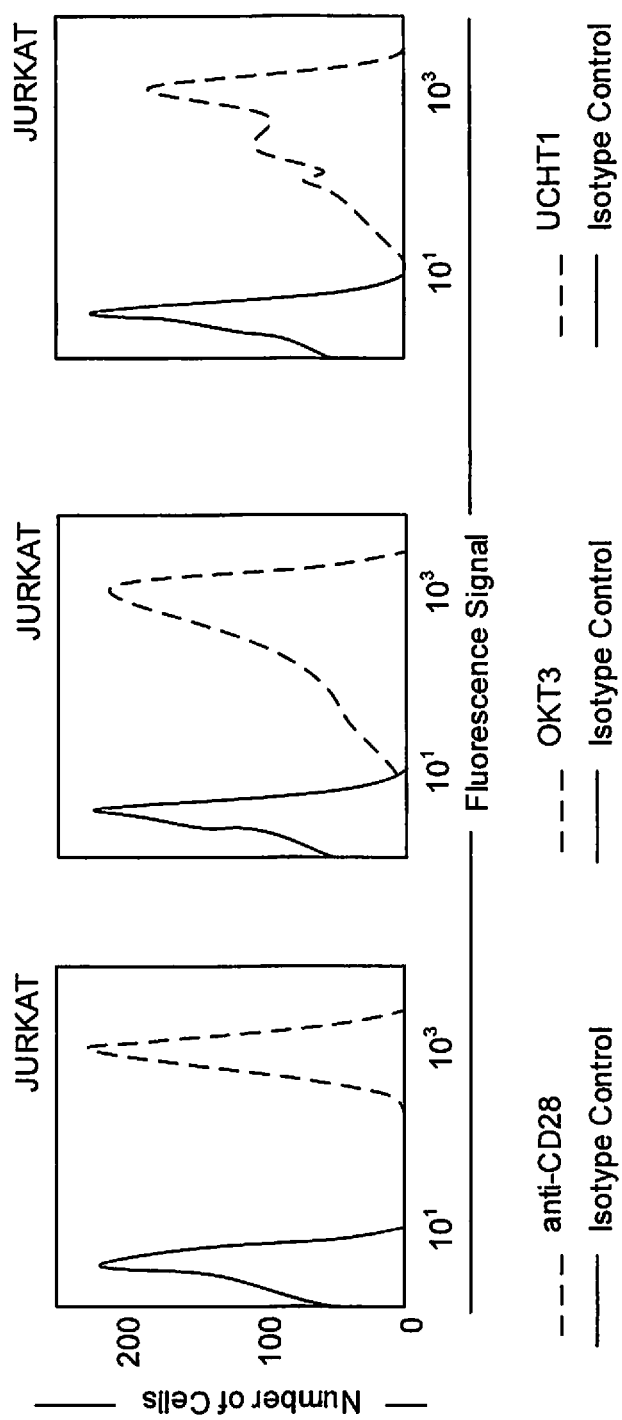
FIG. 16 are graphs resulting from secondary staining of Jurkat.E6 cells used for mAb competition assay, showing binding of all three antibodies (anti-CD28, OKT3 and UCHT1) with Jurkat.E6 cells.

Aptamer specificity against TCR-CD3ε: The bioinformatics analysis based on LIGS experiments and the initial specificity and cross-competition results all suggest that the identified aptamers bind to TCR-CD3 receptor complex. However, TCR-CD3ε specificity was further validated using two different approaches. First, a double-knockout Jurkat cell line that was generated by CRISPR targeting of the TRAC gene that encodes the alpha constant chain of T-cell receptor and the CD3ε gene that encodes the CD3-epsilon polypeptide was used. The binding of ZUCH-1 aptamer was then tested against wild-type Jurkat.E6 cells and double knockout cells used as negative control. Aptamer ZUCH-1 did not show binding towards the knockout cells, confirming specificity against TCR-CD3ε (FIG. 14A and antibody binding in FIG. 15). Second, epitope specificity was confirmed by competitive binding experiments with the mAbs used in LIGS: OKT3, UCHT1 and anti-CQ28 antibody. Here, since competitive elution correlates with affinity, the aptamer with the lowest affinity of all five, aptamer ZUCH-5, was selected.

A significant reduction in aptamer binding was observed in the presence of anti-CD3 mAbs compared to the control anti-CD28 antibody (FIG. 14B). Since aptamer ZUCH-5 was identified using LIGS in the presence of the UCHT1 antibody, the competition by UCHT1 antibody was slightly higher than that of the OKT3 antibody. Since UCHT1 and OKT3 antibodies target overlapping epitopes present in CD3-ε/δ and CD3-ε/γ heterodimers, outcompetition of ZUCH-5 by OKT3 mAb was expected.

Next, ZUCH-1, the aptamer with highest affinity, and ZUCH-3, the only aptamer that originated from LIGS against primary T-cells with isolated T-cells, were tested. Both aptamers showed binding with human T-cells, suggesting that these two aptamers are specific to TCR-CD3ε in both cultured and primary cells (FIG. 14C). As expected, the shift observed on the x-axis was higher for ZUCH-1, but 64% lower for ZUCH-3, indicating, again, that specific binding correlates with affinity.

Discussion: SELEX is based op the principles governing combinatorial screening and in vitro evolution. Using three interconnected steps, which include incubation, separation and amplification, SELEX evolves nucleic acid aptamers (NAAs) against a desired target. The basis of SELEX is mainly rooted in the survival of high-affinity binders, while eliminating low-affinity binders that recognize a uniform, folded state of target proteins. This is usually straightforward when soluble proteins are used. However, when the target protein is a membrane-bound protein, solubilizing the receptor proteins while mimicking native folded state is challenging. This is because cell-surface receptor proteins rely on lipid rafts and the lipid bilayer to stabilize and maintain their structural integrity. Despite these challenges, the identification of NAAs against cell-specific receptors has progressed rapidly in the last decade owing to key advancements. For example, if the epitope remained unchanged, Morris and coworkers demonstrated that aptamers could be identified against isolated membranes and that the diversity of a SELEX library is sufficient to enrich aptamers against multiple targets. The next key contribution was the introduction of cell-SELEX in which whole cells are used as the target. The advantage of cell-SELEX is the capacity to discover a panel of aptamers against whole cells where target cell receptors are in their native environment, as well as the ability to incorporate negative selection into the process to remove aptamers of undesired targets. Furthermore, the recent application of next-generation sequencing (NGS) in SELEX has enabled unprecedented depth analysis into the sequence enrichment process in SELEX.

A novel method with unparalleled applicability in identifying specific ligands without changing the native environment of the cell-surface receptor is introduced. By combining ligand-receptor interactions, in vitro evolution, and Illumina sequencing followed by bioinformatics analysis in LIGS, this disclosure demonstrates how to streamline the identification of aptamer hits against known cell-surface receptors in their native functional state, while still utilizing an enriched cell-SELEX pool against a whole cell. In addition, the assimilation of LIGS in primary T-cells demonstrates the feasibility and simplicity of this system in expanding the repertoire of targets. LIGS is designed to interrupt selection by introducing a strong bivalent competing ligand, such as a mAb. Two mAbs, OKT3 and UCHT1, were used against two binding regions of the TCR-CD3ε complex. The mAbs are large 150 kDa molecules that are the most likely to trigger a conformational switch as they bind antigens, thus eluting specific aptamers by destabilizing the aptamer-protein complex. Also introducing steric hindrance, owing to the large size of mAbs, can elute aptamers.

In this disclosure LIGS is combined with NGS Illumina sequencing, followed by bioinformatics analysis to identify functional nucleic acid ligands against TCR-CD3 complex from an enriched combinatorial library. First, using the FASTAptamer toolkit and the GALAXY platform, sequenced pools were analyzed to determine the nature of sequences in the evolved pools from round 7 to 16 in the cell-SELEX process. Interestingly, analysis of library enrichment with flow cytometry correlates with bioinformatics analysis, suggesting that the cell-SELEX pool was substantially enriched against target cell line Jurkat.E6.

To obtain highly specific aptamers with high affinity, the LIGS conditions were optimized. Thus, while taking advantage of the interaction between a mAb and its antigen, concentrations of both secondary competing mAb ligands were manipulated and the enriched cell-SELEX library to facilitate elution of highly specific and high-affinity aptamers against TCR-CD3ε. First, the concentrations of secondary competing mAb ligands were used at twenty times higher than the $K_d$ of each mAb toward its epitope. At the same time, the concentrations of the enriched cell-SELEX pools were manipulated based on predefined conditions to ensure that the concentration of outcompeted high-affinity aptamer ligand in a cell-SELEX pool would be below its $K_d$. At any given concentration, the individual concentration of DNA ligands in a SELEX pool is substantially low in the partial enrichment stage; however, in an enriched library, high-affinity aptamers can potentially be present in a high number of copies, contesting the out-competition by a secondary ligand. Taking this fact into account, three scenarios were defined to ensure the out-competition of high-affinity aptamers during LIGS. In scenario one, the displacement of the bound aptamer at equilibrium was permitted by adding excess of the competing secondary mAb against a cell-SELEX pool with free ligands in solution. In scenario two, equilibrium displacements were permitted by using a competing mAb in excess against a cell-SELEX pool with no free ligand in solution. With these predefined scenarios, the $K_d$ and maximum binding ($B_{max}$) concentration of cell-SELEX pool towards Jurkat.E6 in each scenario were evaluated.

During the first two scenarios, the concentration of the cell-SELEX pool was kept at half that of the $K_d$, which led to a reduction in the individual concentration of high-affinity ligands, thus favoring the out-competition of those ligands. In addition to this, the concentration of the cell-SELEX pool was kept equal to the $K_d$ for both scenarios, which allowed any aptamer ligand competing with the secondary competitor to be eluted irrespective of its affinity. Similar conditions were utilized when free ligands were washed, which involves disruption of the equilibrium between aptamer and target. In the second scenario, however, only high-affinity aptamers would be expected to be bound to their corresponding epitope, while low-affinity aptamers would be dissociated from their bound state and released into solution without a secondary competitor. In scenario three, the competing mAb was washed post-incubation, and the cell-SELEX pool was kept with free ligands, again at a concentration equal to half that of the $K_d$. All pools were collected from LIGS conditions discussed above and sequenced using Illumina.

Considering the complexity of sequences generated by sequencing each LIGS pool, multiple controls were utilized to address potential off-target sequences in the eluted pools, potentially leading to false-positive hits. Despite the availability of sophisticated bioinformatics tools, a higher number of copies of off-target hits than specific hits was postulated, which would hinder the successful identification of high-affinity, high-specificity sequences. Therefore, an isotype control was first used in each LIGS condition in the three scenarios described above to identify DNA sequences with high off-rates, and these sequences were subtracted from specific pools using the GALAXY platform during bioinformatics analysis. Next, a positive control (anti-CD28 mAb) was used in each LIGS experiment to identify potential sequences eluted by disruption of membrane integrity by mAbs binding to an off-target. The sequencing data resulting from these libraries were also subtracted from sequences eluted by specific mAbs during bioinformatics analysis.

Combining NGS with evaluation of nucleic acids eluted as a function of related molecular interactions in LIGS led to a greater understanding of the nature of outcompeted ligands. 65,085 specific sequences for round 16 of cell-SELEX and 42,182 sequences in round 15 for primary T-cells were initially obtained, as the total number of sequences enriched against whole cells. The resulting sequences obtained from sequencing the supernatant of isotype control were used to eliminate high off-rate sequences out of the total number of sequences from the specific pool of sequences. Changes to membrane structure were considered, which might trigger release of off-target aptamers, such as an antibody binding to a non-target receptor. Thus, sequencing data from positive control mAb anti-CD28 were used to eliminate off-target, cell-specific sequences, which were also subtracted from the total number of sequences. This step resulted in 485 sequences with the potential of high specificity. Next, two specific mAbs were used against the desired target with multiple concentrations of the cell-SELEX pool, which allowed the identification of hits for specific aptamer sequences outcompeted by mAbs. Out of 485 sequences, a family of eight sequences with consensus sequence homology were observed. Typically, when single proteins are used in SELEX, these types of consensus sequence families are identified. Thus, when whole cells are used as the target, the evolution of sequence families was speculated to have originated from a single sequence in the initial library is taking place. However, a detailed investigation of this concept is yet to be conducted. Out of the eight sequences identified, five sequences showed specificity against TCR-CD3ε expressed on Jurkat.E6 cells.

Interestingly, the affinity of the aptamers identified in each LIGS experiment correlates with the concentration of the enriched cell-SELEX pool used in elution. First, when the competing mAb was added and the aptamer-target binding equilibrium was disrupted by washing away free ligand, as described in scenario two, the highest-affinity aptamer eluted was ZUCH-1 with a $K_d$ of 3 nM. Here, use of control mAbs allowed the identification of the high off-rate sequences, which were then removed during sequence analysis using the bioinformatics step. Next, aptamer ZOKT-2 with a $K_d$ of 16.1 nM was identified, ten-fold lower in affinity compared to the outcompeting secondary ligand OKT3 ($K_d$=1.5 nM). Here, the concentration of cell-SELEX pool was kept at half the $K_d$, permitting the presence of free aptamers during LIGS. Next, aptamer ZUCH-4 with affinity of 52.5 nM was also discovered using scenario one when the concentration of the cell-SELEX pool was kept equal to its $K_d$ during LIGS. Both aptamers show substantial affinity; however, aptamer ZOKT-2 shows substantially higher affinity compared to aptamer ZUCH-4, suggesting that applying very high selection pressure towards the cell-SELEX pool during LIGS elutes higher-affinity aptamers. Finally, the aptamer with lowest affinity ZUCH-5, was discovered when the secondary competing mAb was not in excess (scenario three), and the cell-SELEX pool was at equilibrium with free ligands. Here, selection pressure towards the library was at its minimum, and limiting the concentration of the secondary mAb competitor allowed the free binding of the enriched pool with whole cells. Interestingly, aptamer ZUCH-3 with a $K_d$ of 27 nM was discovered when LIGS was utilized against primary T-cells using scenario two during LIGS with human T-cells, leading to an aptamer able to recognize TCR-CD3ε expressed in both primary and cultured T-cells.

It is widely accepted that high specificity can be obtained with aptamers with higher affinity. Aptamers with increased affinity by dimerization lead to universal binding towards their target moiety. Therefore, despite the fact that aptamer ZUCH-1 was selected with LIGS using cultured T cells, this aptamer successfully identified TCR-CD3ε in human T-cells. It is noteworthy that the binding against human T cells was higher with aptamer ZUCH-1. In conclusion, this disclosure has demonstrated a method that combines molecular interactions, combinatorial screening, in vitro evolution and next-generation sequencing to identify functional nucleic acid ligands against a multi-component cell-surface receptor expressed on the cell membrane. The disclosure also demonstrated that the incorporation of primary T-cells during cell-SELEX followed by LIGS allowed identification of an aptamer against TCR-CD3ε expressed in primary T-cells, suggesting that the repertoire of targets can be expanded in LIGS. While affinity can vary based on LIGS conditions, such as order of incubation and concentration of enrich pool utilized or order of incubation and concentration of competing ligands, the unprecedented specificity of all five aptamers confirms the significance of LIGS in generating specific aptamers. Finally, the disclosure showed that the use of existing receptor and a ligand interaction can be utilized to identify highly specific, high-affinity aptamers from an enriched cell-SELEX pool against a target protein receptor. LIGS technology was further improved in this study by incorporating NGS, followed by bioinformatics analysis using the FASTAptamer toolkit and GALAXY. The convenience of NGS allowed the use of multiple controls to eliminate off-target sequences, further strengthening the ability of LIGS technology to identify highly specific, high-affinity aptamers against multi-component cell-surface receptors. Here, the disclosure targeted the TCR-CD3 complex (T-cell Surface Glycoprotein CD3 Epsilon), which is a type I transmembrane protein that belongs to the Ig (Immunoglobulin) superfamily and a key receptor expressed in T-cells that governs immune responses. All five aptamers selected are potentially applicable in the development of DNA-based immunomodulators, potentially leading to DNA-based immunotherapeutic agents.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A Ligand-guided-Selection method for screening ligands that are specific to a predetermined antigen, the method comprising sequential steps of:
   forming a ligand-cell complex by exposing a culture of target cells to a library of ligands that is at least partially enriched, wherein cells in the culture of target cells each have the predetermined antigen;
   treating the ligand-cell complex with a predetermined ligand that is specific to the predetermined antigen, the predetermined ligand displacing ligands that are bound to the predetermined antigen to form displace ligands, the step of treating leaving non-displaced ligands bound to the ligand-cell complex, wherein the predetermined ligand is an antibody;
   eluting the displaced ligands; and
   amplifying the displaced ligands; wherein the step of amplifying the displaced ligands comprises a polymerase chain reaction (PCR).

2. The method as recited in claim 1, wherein the antibody has a molecular weight between 65 kDa and 150 kDa.

3. The method as recited in claim 1, further comprising treating the ligand-cell complex with an off-target antibody that binds at an antigen other than the predetermined antigen.

4. The method as recited in claim 1, wherein the culture of target cells is washed to remove free ligands prior to the step of forming and the antibody is present in a molar excess relative to the predetermined antigen.

5. The method as recited in claim 1, wherein the culture of target cells is not washed prior to the step of forming, thus leaving free ligands present during the step of forming and the antibody is present in a molar excess relative to the predetermined antigen.

6. The method as recited in claim 1, wherein free ligands are present during the step of forming.

7. The method as recited in claim 1, further comprising a step of removing free ligands by washing prior to the step of forming.

8. The method as recited in claim 1, wherein the library of ligands has a plurality of aptamers, each having a dissociation constant ($K_d$), wherein the step of forming uses a concentration of each aptamer equal to or below its dissociation constant ($K_d$).

9. The method as recited in claim 1, wherein the library of ligands has a plurality of aptamers, each having a dissociation constant ($K_d$), wherein the step of forming uses a concentration of each aptamer equal to or below half of its dissociation constant ($K_d$).

10. The method as recited in claim 1, wherein the antibody has a molecular weight greater than 150,000 g per mole.

11. The method as recited in claim 1, wherein the antibody is present in at least a five-fold molar excess relative to the predetermined antigen.

12. The method as recited in claim 1, wherein the antibody is present in at least a ten-fold molar excess relative to the predetermined antigen.

13. A Ligand-guided-Selection method for screening ligands that are specific to a predetermined antigen, the method comprising sequential steps of:
constructing a library of ligands that is at least partially enriched by:
exposing a target cell line to an aptamer library and permitting at least some aptamers to bind to the target cell line, thereby forming bound aptamers;
removing aptamers that do not bind to the target cell line;
eluting the bound aptamers, thereby forming eluted aptamers;
amplifying the eluted aptamers that are specific to the cell line, thereby forming the library of ligands;
forming a ligand-cell complex by exposing a culture of target cells to the library of ligands, wherein cells in the culture of target cells each have the predetermined antigen;
treating the ligand-cell complex with an antibody that is specific to the predetermined antigen, the antibody displacing ligands that are bound to the predetermined antigen to form displace ligands, the step of treating leaving non-displaced ligands bound to the ligand-cell complex;
eluting the displaced ligands;
amplifying the displaced ligands using polymerase chain reaction (PCR).

14. The method as recited in claim 13, further comprising:
performing a sequence alignment on first ligands from the library of ligands and second ligands from the displaced ligands;
identifying, based on the sequence alignment, a common sequence of nucleotides.

15. The method as recited in claim 14 wherein the step of identifying identifies the common sequence of nucleotides by finding at least four repeats of the common sequence within the first ligands from the library of ligands and second ligands from the displaced ligands.

16. A method for selecting aptamers using an antibody-capped cell Systematic Evolution of Ligands by EXponential enrichment process, the method comprising steps of:
exposing an antibody-capped cell to a plurality of different aptamers and permitting at least some aptamers to bind to the antibody-capped cell to form bound aptamers, wherein the antibody-capped cell has been pre-treated with a predetermined antibody that caps an antigen;
eluting unbound aptamers; and
amplifying the unbound aptamers.

17. The method as recited in claim 16, wherein the plurality of different aptamers are produced by:
exposing a target cell to an aptamer library;
permitting at least some aptamers in the aptamer library to bind to the target cell to form bound aptamers;
eluting unbound aptamers;
eluting the bound aptamers from the target cell to produce the plurality of different aptamers.

* * * * *